United States Patent
Rueger et al.

(10) Patent No.: US 6,723,698 B2
(45) Date of Patent: *Apr. 20, 2004

(54) METHODS AND COMPOSITIONS FOR THE TREATMENT OF MOTOR NEURON INJURY AND NEUROPATHY

(75) Inventors: David C. Rueger, Southborough, MA (US); Kuber T. Sampath, Holliston, MA (US); Hermann Oppermann, Medway, MA (US); Roy H. L. Pang, Etna, NH (US); Charles M. Cohen, Weston, MA (US)

(73) Assignee: Curis, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/937,755

(22) Filed: Sep. 25, 1997

(65) Prior Publication Data

US 2002/0049159 A1 Apr. 25, 2002

Related U.S. Application Data

(63) Continuation-in-part of application No. 08/260,675, filed on Jun. 16, 1994, which is a continuation of application No. 08/126,100, filed on Sep. 23, 1993, now abandoned, which is a continuation of application No. 07/922,813, filed on Jul. 31, 1992, now abandoned, which is a continuation-in-part of application No. 07/752,764, filed on Aug. 30, 1991, now abandoned, which is a continuation-in-part of application No. 07/753,059, filed on Aug. 30, 1991, now abandoned, which is a continuation-in-part of application No. 07/667,274, filed on Mar. 11, 1991, now abandoned.

(51) Int. Cl.[7] .............................................. A61K 38/00

(52) U.S. Cl. ........................................ 514/12; 530/351

(58) Field of Search ............................. 514/12; 530/351

(56) References Cited

U.S. PATENT DOCUMENTS 5,108,989 A    4/1992  Amento et al.

FOREIGN PATENT DOCUMENTS

| WO | WO 84/01106 | 3/1984 |
| WO | WO 92/15323 | 9/1992 |
| WO | WO 94/03200 | 2/1994 |
| WO | WO 95/05846 | 3/1995 |
| WO | WO 95/06656 | 3/1995 |
| WO | WO 95/10611 | 4/1995 |

OTHER PUBLICATIONS

Rudinger, Peptide Hormones, ed.Parsons, Univ.Park Press, p. 1–7, 1978.*
Varley et al, Developmental Dynamics 203:434–447, 1995.*
The Merck Manual of Diagnosis and Therapy, 18th ed., (editor–in–chief Berkow), p. 1512–1513, 1992.*
Aebischer, et al. (1989), "Basic Fibroblast Growth Factor Released From Synthetic Guidance Channels Facilitating Peripheral Nerve Regeneration Across Long Nerve Gaps," 23 *J. Neurosci. Res.* 282–289.
Barde (1989), "Trophic Factors And Neuronal Survival," 2 *Neuron* 1525–1534.
Basler, et al., (1993) "Control of Cell Pattern in the Neural Tube: Regulation of Cell Differentiation by dorsalin–1, a Novel TGFβ Family Member", 73 *Cell*, 687–702.
Carswell (1993), "The Potential for Treating Neurodegenerative Disorders with NGF–Inducing Compounds," *Exp. Neurol.* 36.
de Koninck, et al. (1993), "NGF Induced Neonatal Rat Sensory Neurons to Extend Dendrites in Culture After Removal of Satellite Cells," 13 *J. Neurosci.* 577–585.
Deininger, et al. (1995), "Detection of Two Transforming Growth Factor–β–Related Morphogens, Bone Morphogenetic Proteins –4 and –5, in RNA of Multiple Sclerosis and Creutzfeldt–Jakob Disease Lesions," 90 *Acta Neuropathol.* 76–79.
Dedhar, et al. (1993), "Differential Regulation of Expression of Specific Integrin Receptors by Nerve Growth Factor and Transforming Growth Factor β1 During Differentiation of Human Neuroblastoma Cells", 1 (1): *Molecular and Cellular Differentiation*, 1–20.
Ebendal (1992), "Function and Evolution in the NGF Family and Its Receptors," 32 *J. Neurosci. Res.* 461.
Ebendal et al. (1991) "Human Nerve Growth Factor: Biological and Immunological Activities, and Clinical Possibilities in the Neurodegenerative Disease," *Plasticity and Regeneration of the Nervous System* 207–225 (Timeras, et al., eds., Plenum Press N.Y.).

(List continued on next page.)

*Primary Examiner*—Gary Kunz
*Assistant Examiner*—Sharon Turner
(74) *Attorney, Agent, or Firm*—Ropes & Gray LLP

(57) ABSTRACT

Disclosed are therapeutic treatment methods, compositions and devices for maintaining neural pathways in a mammal, including enhancing survival of neurons at risk of dying, inducing cellular repair of damaged neurons and neural pathways, and stimulating neurons to maintain their differentiated phenotype. In one embodiment, the invention provides means for stimulating CAM expression in neurons. The invention also provides means for evaluating the status of nerve tissue, including means for detecting and monitoring neuropathies in a mammal. The methods, devices and compositions include a morphogen or morphogen-stimulating agent provided to the mammal in a therapeutically effective concentration.

16 Claims, 15 Drawing Sheets

OTHER PUBLICATIONS

Friedlander, et al. (1986), "Nerve Growth Factor Enhances Expression of Neuron–Glia Cell Adhesion Molecule in PC12 Cells," 102 *J.C.B.* 413–419.

Gash, et al. (1996), "Functional Recovery in Parkinsonian Monkeys Treated with GDNF," 380 *Nature* 252–255.

Gross, et al. (1993), "Transforming Growth Factor–β1 Reduces Infarct Size After Experimental Cerebral Ischemia in a Rabbit Model," 24 *Stroke* 558–562.

Hefti, et al. (1993), "Pharmacology of Nerve Growth Factor in the Brain," 24 *Adv. in Pharmacol.* 239–273.

Jackowski, et al. (1995), "Neural Injury Repair: Hope For The Future As Barrier To Effective CNS Regeneration Become Clearer," 9 *Brit. J. Neurosurgery*, 303–317.

Jones, et al. (1991), "Involvement of Bone Morphogenetic Proteins . . . " 111 *Development* 2:531–542.

Lee (1991), "Expression of Growth/Differentiation Factor 1 in the Nervous System: Conservation of a Bicistronic Structure," 88 *Proc. Natl. Acad. Sci. USA*, 4250–4254.

Lefer, et al. (1992), "Anti–Ischaemic and Endothelial Protective Actions of Recombinant Human Osteogenic Protein (hOP–1)," *J. Mol. Cell. Card* 24:585–593.

Lein, et al. (1995), "Osteogenic Protein–1 Induces Dendritic Growth in Rat Sympathetic Neurons in Vitro," 15 *Neuron* 597–605.

Lein, et al. (1989), "Laminin and a Basement Membrane Extract Have Different Effects on Axonal and Dendritic Outgrowth From Embryonic Rat Sympathetic Neurons in Vitro," 136 *Dev. Biol.* 330–345.

LeRoux, et al. (1994), "Regional Differences in Glial–Derived Factors That Promote Dendritic Outgrowth From Mouse Cortical Neurons In Vitro," 14 *J. Neurosci.* 8:4639–4655.

Lundborg (1987), "Nerve Regeneration and Repair," 58 *Acta. Orthop. Scand.* 145–169.

Perides, et al. (1995), "Neuroprotective Effect of Human Osteogenic Protein 1 in a Rat Model of Cerebral Hypoxia/Ischemia," 187 *Neurosci. Lett.* 21–24.

Purves, et al. (1988), "Trophic Regulation of Nerve Cell Morphology and Innervation in the Autonomic Nervous System," 336 *Nature* 123–128.

Reissmann, et al. (1996), "Involvement of Bone Morphogenic Protein–4 and Bone Morphogenic Protein–7 In The Differentiation of the Adrenergic Phenotype In Developing Sympathetic Neurons," 122 *Development* 2079–2088.

Roubin, et al. (1990), "Modulation of NCAM Expression by Transforming Growth Factor–Beta, Serum, and Autocrine Factors," 111 *J. Cell Biol.* 673–684.

Sadd, et al. (1991),"Astrocyte–Derived TGF–B2 and NGF Differentially Regulate Neural Recognition Molecule Expression by Cultured Astrocytes, "*J. Cell Biol.* 2473–484.

Sasai, et al. (1995),"Regulation of Neural Induction by the Chd and Bmp–4 Antagonistic Patterning Signals in Xenopus", *Nature 367*: 333–336.

Schubert, et al., (1990) "Activin is a Nerve Cell Survival Molecule", *Nature*, 344:868–870.

Shah, et al. (1995), "Alternative Neural Crest Cell Fates Are Instructively Promoted by TGF–β Superfamily Members," 85 *Cell* 331–343.

Snider (1988), "Nerve Growth Factor Enhances Dendritic Arborization of Sympathetic Ganglion Cells in Developing Mammals," 8 *J. Neurosci.* 2628–2634.

Stromberg, et al. (1993), "Glial Cell Line–Derived Neurotrophic Factors is Expressed in the Developing but Not Adult Striatum and Stimulates Developing Dopamine Neurons in vivo," 124 *Exp. Neurol.* 401–412.

Tomac, et al. (1995), "Protection and Repair of the Nigrostriatal Dopaminergic System by GDNF in vivo," 373 *Nature* 335–346.

Wilson, et al. (1995), "Induction of Epidermis and Inhibition of Neural Fate by Bmp–4," 376 *Nature* 331–333.

Withers, et al. (1996), "Receptivity of Osteogenic Protein–1 (OP–1)—Induced Dendrites to Axonal Innervation," *Society for Neuroscience*, meeting abstract.

Withers, et al. (1995), "Osteogenic Protein–1 (OP–1) Induces Dendritic Growth and Branching in Cultured Hippocampal Neurons", *Society for Neuroscience*, meeting abstract.

* cited by examiner

% SEQUENCE SIMILARITY TO HUMAN OP-1 SEVEN-CYSTEINE DOMAIN

| SEQUENCE | % SIMILARITY | % NON CONSERVATIVE |
|---|---|---|
| hOP-1 | 100 | 0 |
| mOP-1 | 100 | 0 |
| hOP-2 | 97 | 3 |
| mOP-2 | 97 | 3 |
| BMP-5 | 97 | 3 |
| BMP-6 | 96 | 4 |
| Vgr-1(PT) | 94 | 6 |
| OP-3 | 91 | 9 |
| 60A | 90 | 10 |
| BMP-4 | 90 | 10 |
| BMP-2 | 89 | 11 |
| dpp | 87 | 13 |
| UNIVIN | 87 | 13 |
| dpp(PT) | 86 | 14 |
| Vg-1 | 86 | 14 |
| CDMP-1 | 85 | 15 |
| CDMP-3 | 83 | 17 |
| GDF-3 | 83 | 17 |
| CDMP-2 | 82 | 18 |
| DORSALIN | 79 | 21 |
| CDF-1(PT) | 78 | 22 |
| GDF-10 | 78 | 22 |
| BMP-3b | 78 | 22 |
| BMP-10 | 78 | 23 |
| BMP-3 | 78 | 23 |
| SCREW | 77 | 23 |
| ADMP | 77 | 24 |
| TGF-β2 | 73 | 27 |
| GDF-1 | 73 | 28 |
| BMP-9 | 73 | 28 |
| NODAL | 71 | 29 |
| InhibinβA | 71 | 29 |
| BMP-15 | 71 | 29 |
| TGF-β3 | 69 | 31 |
| InhibinβB | 69 | 31 |
| InhibinβC | 69 | 31 |
| TGF-β5 | 67 | 33 |
| TGF-β1 | 67 | 33 |
| GDF-12 | 67 | 33 |
| GDF-11 | 66 | 34 |
| TGF-β4 | 66 | 34 |
| GDF-9 | 66 | 34 |
| GDF-8 | 64 | 36 |
| BMP-11 | 60 | 40 |
| GDNF | 49 | 51 |

Fig. 1

VEHICLE   OP-1

VEHICLE     OP-1

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1822 base pairs
      (B) TYPE: nucleic acid
      (C) STRANDEDNESS: single
      (D) TOPOLOGY: linear (ii) MOLECULE TYPE: cDNA (vi) ORIGINAL SOURCE:

-continued

```
     (A) ORGANISM: HOMO SAPIENS
     (F) TISSUE TYPE: HIPPOCAMPUS (ix) FEATURE:
     (A) NAME/KEY: CDS
     (B) LOCATION: 49..1341
     (C) IDENTIFICATION METHOD: experimental
     (D) OTHER INFORMATION: /function= "OSTEOGENIC PROTEIN"
         /product= "OP1"
         /evidence= EXPERIMENTAL
         /standard_name= "OP1"

(xi) SEQUENCE DESCRIPTION: SEQ ID NO:1:
```

| | | | | | | | | | | | | | | | | |
|---|---|---|---|---|---|---|---|---|---|---|---|---|---|---|---|---|
| GGTGCGGGCC | CGGAGCCCGG | AGCCCGGGTA | GCGCGTAGAG | CCGGCGCG | ATG | CAC | GTG | | | | | | | | | 57 |
| | | | | | Met | His | Val | | | | | | | | | |
| | | | | | 1 | | | | | | | | | | | |

| CGC | TCA | CTG | CGA | GCT | GCG | GCG | CCG | CAC | AGC | TTC | GTG | GCG | CTC | TGG | GCA | 105 |
|---|---|---|---|---|---|---|---|---|---|---|---|---|---|---|---|---|
| Arg | Ser | Leu | Arg | Ala | Ala | Ala | Pro | His | Ser | Phe | Val | Ala | Leu | Trp | Ala | |
| | 5 | | | | 10 | | | | 15 | | | | | | | |

| CCC | CTG | TTC | CTG | CTG | CGC | TCC | GCC | CTG | GCC | GAC | TTC | AGC | CTG | GAC | AAC | 153 |
|---|---|---|---|---|---|---|---|---|---|---|---|---|---|---|---|---|
| Pro | Leu | Phe | Leu | Leu | Arg | Ser | Ala | Leu | Ala | Asp | Phe | Ser | Leu | Asp | Asn | |
| 20 | | | | | 25 | | | | 30 | | | | | | 35 | |

| GAG | GTG | CAC | TCG | AGC | TTC | ATC | CAC | CGG | CGC | CTC | CGC | AGC | CAG | GAG | CGG | 201 |
|---|---|---|---|---|---|---|---|---|---|---|---|---|---|---|---|---|
| Glu | Val | His | Ser | Ser | Phe | Ile | His | Arg | Arg | Leu | Arg | Ser | Gln | Glu | Arg | |
| | | | | 40 | | | | | 45 | | | | | 50 | | |

| CGG | GAG | ATG | CAG | CGC | GAG | ATC | CTC | TCC | ATT | TTG | GGC | TTG | CCC | CAC | CGC | 249 |
|---|---|---|---|---|---|---|---|---|---|---|---|---|---|---|---|---|
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |

| CCG | CGC | CCG | CAC | CTC | CAG | GGC | AAG | CAC | AAC | TCG | GCA | CCC | ATG | TTC | ATG | 297 |
|---|---|---|---|---|---|---|---|---|---|---|---|---|---|---|---|---|
| Pro | Arg | Pro | His | Leu | Gln | Gly | Lys | His | Asn | Ser | Ala | Pro | Met | Phe | Met | |
| | | 70 | | | | | 75 | | | | | 80 | | | | |

| CTG | GAC | CTG | TAC | AAC | GCC | ATG | GCG | GTG | GAG | GAG | GGC | GGC | GGG | CCC | GGC | 345 |
|---|---|---|---|---|---|---|---|---|---|---|---|---|---|---|---|---|
| Leu | Asp | Leu | Tyr | Asn | Ala | Met | Ala | Val | Glu | Glu | Gly | Gly | Gly | Pro | Gly | |
| 85 | | | | | 90 | | | | | 95 | | | | | | |

| GGC | CAG | GGC | TTC | TCC | TAC | CCC | TAC | AAG | GCC | GTC | TTC | AGT | ACC | CAG | GGC | 393 |
|---|---|---|---|---|---|---|---|---|---|---|---|---|---|---|---|---|
| Gly | Gln | Gly | Phe | Ser | Tyr | Pro | Tyr | Lys | Ala | Val | Phe | Ser | Thr | Gln | Gly | |
| 100 | | | | | 105 | | | | | 110 | | | | | 115 | |

| CCC | CCT | CTG | GCC | AGC | CTG | CAA | GAT | AGC | CAT | TTC | CTC | ACC | GAC | GCC | GAC | 441 |
|---|---|---|---|---|---|---|---|---|---|---|---|---|---|---|---|---|
| Pro | Pro | Leu | Ala | Ser | Leu | Gln | Asp | Ser | His | Phe | Leu | Thr | Asp | Ala | Asp | |
| | | | | 120 | | | | | 125 | | | | | 130 | | |

| ATG | GTC | ATG | AGC | TTC | GTC | AAC | CTC | GTG | GAA | CAT | GAC | AAG | GAA | TTC | TTC | 489 |
|---|---|---|---|---|---|---|---|---|---|---|---|---|---|---|---|---|
| Met | Val | Met | Ser | Phe | Val | Asn | Leu | Val | Glu | His | Asp | Lys | Glu | Phe | Phe | |
| | | | 135 | | | | | 140 | | | | | 145 | | | |

| CAC | CCA | CGC | TAC | CAC | CAT | CGA | GAG | TTC | CGG | TTT | GAT | CTT | TCC | AAG | ATC | 537 |
|---|---|---|---|---|---|---|---|---|---|---|---|---|---|---|---|---|
| His | Pro | Arg | Tyr | His | His | Arg | Glu | Phe | Arg | Phe | Asp | Leu | Ser | Lys | Ile | |
| | | 150 | | | | | 155 | | | | | 160 | | | | |

| CCA | GAA | GGG | GAA | GCT | GTC | ACG | GCA | GCC | GAA | TTC | CGG | ATC | TAC | AAG | GAC | 585 |
|---|---|---|---|---|---|---|---|---|---|---|---|---|---|---|---|---|
| Pro | Glu | Gly | Glu | Ala | Val | Thr | Ala | Ala | Glu | Phe | Arg | Ile | Tyr | Lys | Asp | |
| | 165 | | | | | 170 | | | | | 175 | | | | | |

| TAC | ATC | CGG | GAA | CGC | TTC | GAC | AAT | GAG | ACG | TTC | CGG | ATC | AGC | GTT | TAT | 633 |
|---|---|---|---|---|---|---|---|---|---|---|---|---|---|---|---|---|
| Tyr | Ile | Arg | Glu | Arg | Phe | Asp | Asn | Glu | Thr | Phe | Arg | Ile | Ser | Val | Tyr | |
| 180 | | | | | 185 | | | | | 190 | | | | | 195 | |

| CAG | GTG | CTC | CAG | GAG | CAC | TTG | GGC | AGG | GAA | TCG | GAT | CTC | TTC | CTG | CTC | 681 |
|---|---|---|---|---|---|---|---|---|---|---|---|---|---|---|---|---|
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |

| GAC | AGC | CGT | ACC | CTC | TGG | GCC | TCG | GAG | GAG | GGC | TGG | CTG | GTG | TTT | GAC | 729 |
|---|---|---|---|---|---|---|---|---|---|---|---|---|---|---|---|---|
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |

| ATC | ACA | GCC | ACC | AGC | AAC | CAC | TGG | GTG | GTC | AAT | CCG | CGG | CAC | AAC | CTG | 777 |
|---|---|---|---|---|---|---|---|---|---|---|---|---|---|---|---|---|
| Ile | Thr | Ala | Thr | Ser | Asn | His | Trp | Val | Val | Asn | Pro | Arg | His | Asn | Leu | |
| | | | 230 | | | | | 235 | | | | | 240 | | | |

| GGC | CTG | CAG | CTC | TCG | GTG | GAG | ACG | CTG | GAT | GGG | CAG | AGC | ATC | AAC | CCC | 825 |
|---|---|---|---|---|---|---|---|---|---|---|---|---|---|---|---|---|

```
Gly Leu Gln Leu Ser Val Glu Thr Leu Asp Gly Gln Ser Ile Asn Pro
        245                 250                 255

AAG TTG GCG GGC CTG ATT GGG CGG CAC GGG CCC CAG AAC AAG CAG CCC      873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC      921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC      969
Arg Ser Thr Gly Ser Lys Gln Arg Ser Gln Asn Arg Ser Lys Thr Pro
                295                 300                 305

AAG AAC CAG GAA GCC CTG CGG ATG GCC AAC GTG GCA GAG AAC AGC AGC     1017
Lys Asn Gln Glu Ala Leu Arg Met Ala Asn Val Ala Glu Asn Ser Ser
            310                 315                 320

AGC GAC CAG AGG CAG GCC TGT AAG AAG CAC GAG CTG TAT GTC AGC TTC     1065
Ser Asp Gln Arg Gln Ala Cys Lys Lys His Glu Leu Tyr Val Ser Phe
325                 330                 335

CGA GAC CTG GGC TGG CAG GAC TGG ATC ATC GCG CCT GAA GGC TAC GCC     1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG     1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC     1209
Asn Ala Thr Asn His Ala Ile Val Gln Thr Leu Val His Phe Ile Asn
                375                 380                 385

CCG GAA ACG GTG CCC AAG CCC TGC TGT GCG CCC ACG CAG CTC AAT GCC     1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA     1305
Ile Ser Val Leu Tyr Phe Asp Asp Ser Ser Asn Val Ile Leu Lys Lys
405                 410                 415

TAC AGA AAC ATG GTG GTC CGG GCC TGT GGC TGC CAC TAGCTCCTCC          1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAACAAC    1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAAATTGAC CCGGAAGTTC   1771

CTGTAATAAA TGTCACAATA AAACGAATGA ATGAAAAAAA AAAAAAAAA A            1822

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
```

```
                20                  25                  30
Leu Asp Asn Glu Val His Ser Ser Phe Ile His Arg Arg Leu Arg Ser
            35                  40                  45
Gln Glu Arg Arg Glu Met Gln Arg Glu Ile Leu Ser Ile Leu Gly Leu
50                  55                  60
Pro His Arg Pro Arg Pro His Leu Gln Gly Lys His Asn Ser Ala Pro
65                  70                  75                  80
Met Phe Met Leu Asp Leu Tyr Asn Ala Met Ala Val Glu Glu Gly Gly
                85                  90                  95
Gly Pro Gly Gly Gln Gly Phe Ser Tyr Pro Tyr Lys Ala Val Phe Ser
            100                 105                 110
Thr Gln Gly Pro Pro Leu Ala Ser Leu Gln Asp Ser His Phe Leu Thr
        115                 120                 125
Asp Ala Asp Met Val Met Ser Phe Val Asn Leu Val Glu His Asp Lys
    130                 135                 140
Glu Phe Phe His Pro Arg Tyr His His Arg Glu Phe Arg Phe Asp Leu
145                 150                 155                 160
Ser Lys Ile Pro Glu Gly Glu Ala Val Thr Ala Ala Glu Phe Arg Ile
                165                 170                 175
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
    210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Arg Ser Gln Asn Arg Ser
    290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430
```

(2) INFORMATION FOR SEQ ID NO:3:

-continued

```
     (i) SEQUENCE CHARACTERISTICS:
          (A) LENGTH: 102 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: Protein
          (B) LOCATION: 1..102
          (D) OTHER INFORMATION: /label= OPX
               /note= "wherein each Xaa is independently selected from
               a group of one or more specified amino acids as defined
               in the specification."

(xi) SEQUENCE DESCRIPTION: SEQ ID NO:3:

Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100

(2) INFORMATION FOR SEQ ID NO:4:

(i) SEQUENCE CHARACTERISTICS:
          (A) LENGTH: 97 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: Protein
          (B) LOCATION: 1..97
          (D) OTHER INFORMATION: /label= Generic-Seq-7
               /note= "wherein each Xaa is independently selected from
               a group of one or more specified amino acids as defined
               in the specification."

(xi) SEQUENCE DESCRIPTION: SEQ ID NO:4:

Leu Xaa Xaa Xaa Phe Xaa Xaa Xaa Gly Trp Xaa Xaa Xaa Xaa Xaa Xaa
1               5                   10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Xaa
        35                  40                  45

Xaa Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95
```

Xaa (2) INFORMATION FOR SEQ ID NO:5:

(i) SEQUENCE CHARACTERISTICS:
        (A) LENGTH: 102 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-8
            /note= "wherein each Xaa is independently selected from
            a group of one or more specified amino acids as defined
            in the specification."

(xi) SEQUENCE DESCRIPTION: SEQ ID NO:5:

```
Cys Xaa Xaa Xaa Xaa Leu Xaa Xaa Xaa Phe Xaa Xaa Xaa Gly Trp Xaa
1               5                   10                  15

Xaa Xaa Xaa Xaa Xaa Pro Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100
```

(2) INFORMATION FOR SEQ ID NO:6:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-9
            /note= "wherein each Xaa is independently selected from
            a group of one or more specified amino acids as defined
            in the specification."

(xi) SEQUENCE DESCRIPTION: SEQ ID NO:6:

```
Xaa Xaa Xaa Xaa Xaa Xaa Xaa Xaa Xaa Xaa Xaa Xaa Xaa Xaa Xaa Xaa
1               5                   10                  15

Pro Xaa Xaa Xaa Xaa Xaa Xaa Cys Xaa Gly Xaa Cys Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Cys Xaa Pro
    50                  55                  60

Xaa Xaa Xaa Xaa Xaa Xaa Xaa Leu Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa Xaa Cys Xaa Cys
                85                  90                  95

Xaa
```

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-10
            /note= "wherein each Xaa is independently selected from
            a group of one or more specified amino acids as defined
            in the specification."

(xi) SEQUENCE DESCRIPTION: SEQ ID NO:7:

```
Cys Xaa Xaa Xaa Xaa Xaa Xaa Xaa Xaa Xaa Xaa Xaa Xaa Xaa Xaa Xaa
1                5                  10                  15

Xaa Xaa Xaa Xaa Xaa Pro Xaa Xaa Xaa Xaa Xaa Xaa Xaa Cys Xaa Gly
                20                  25                  30

Xaa Cys Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
            50                  55                  60

Xaa Xaa Cys Xaa Pro Xaa Xaa Xaa Xaa Xaa Xaa Xaa Xaa Leu Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Cys Xaa Cys Xaa
            100
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Protein
        (B) LOCATION: 1..5
        (D) OTHER INFORMATION: /note= "wherein each Xaa is
            independently selected from a group of one or more
            specified amino acids as defined in the specification"

(xi) SEQUENCE DESCRIPTION: SEQ ID NO:8:

```
Cys Xaa Xaa Xaa Xaa
1                5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear

```
        -continued (ii) MOLECULE TYPE: peptide (ix) FEATURE:
    (A) NAME/KEY: Protein
    (B) LOCATION: 1..5
    (D) OTHER INFORMATION: /note= "wherein each Xaa is
        independently selected from a group of one or more
        specified amino acids as defined in the specification"

(xi) SEQUENCE DESCRIPTION: SEQ ID NO:9:

Cys Xaa Xaa Xaa Xaa
1               5
```

METHODS AND COMPOSITIONS FOR THE TREATMENT OF MOTOR NEURON INJURY AND NEUROPATHY

RELATED APPLICATIONS

The present application is a continuation-in-part of U.S. Ser. No. 08/260,675, filed Jun. 16, 1994, which is a file wrapper continuation of U.S. Ser. No. 08/126,100, filed Sep. 23, 1993, now abandoned, which is a file wrapper continuation of Ser. No. 07/922,813, filed Jul. 31, 1992, now abandoned, filed as a continuation-in-part of U.S. Ser. No. 07/752,764, now abandoned, and copending U.S. Ser. No. 07/753,059, now abandoned, both filed Aug. 30, 1991 as continuations-in-part of U.S. Ser. No. 07/667,274, filed Mar. 11, 1991, now abandoned. The above-mentioned applications are incorporated by reference herein.

BACKGROUND OF THE INVENTION

The mammalian nervous system comprises a peripheral nervous system (PNS) and a central nervous system (CNS, comprising the brain and spinal cord), and is composed of two principal classes of cells: neurons and glial cells. The glial cells fill the spaces between neurons, nourishing them and modulating their function. Certain glial cells, such as Schwann cells in the PNS and oligodendrocytes in the CNS, also provide a myelin sheath that surrounds neural processes. The myelin sheath enables rapid conduction along the neuron. In the peripheral nervous system, axons of multiple neurons may bundle together in order to form a nerve fiber. These, in turn, may be combined into fascicles or bundles.

During development, differentiating neurons from the central and peripheral nervous systems send out axons that grow and make contact with specific target cells. In some cases, axons must cover enormous distances; some grow into the periphery, whereas others are confined within the central nervous system. In mammals, this stage of neurogenesis is complete during the embryonic phase of life and neuronal cells do not multiply once they have fully differentiated.

A host of neuropathies have been identified that affect the nervous system. The neuropathies, which may affect neurons themselves or associated glial cells, may result from cellular metabolic dysfunction, infection, exposure to toxic agents, autoimmunity, malnutrition, or ischemia. In some cases, the cellular neuropathy is thought to induce cell death directly. In other cases, the neuropathy may induce sufficient tissue necrosis to stimulate the body's immune/inflammatory system and the immune response to the initial injury then destroys neural pathways.

Where the damaged neural pathway results from CNS axonal damage, autologous peripheral nerve grafts have been used to bridge lesions in the central nervous system and to allow axons to make it back to their normal target area. In contrast to CNS neurons, neurons of the peripheral nervous system can extend new peripheral processes in response to axonal damage. This regenerative property of peripheral nervous system axons is thought to be sufficient to allow grafting of these segments to CNS axons. Successful grafting appears to be limited, however, by a number of factors, including the length of the CNS axonal lesion to be bypassed, and the distance of the graft sites from the CNS neuronal cell bodies, with successful grafts occurring near the cell body.

Within the peripheral nervous system, this cellular regenerative property of neurons has limited ability to repair function to a damaged neural pathway. Specifically, the new axons extend randomly, and are often misdirected, making contact with inappropriate targets that can cause abnormal function. For example, if a motor nerve is damaged, regrowing axons may contact the wrong muscles, resulting in paralysis. In addition, where severed nerve processes result in a gap of longer than a few millimeters, e.g., greater than 10 millimeters (mm), appropriate nerve regeneration does not occur, either because the processes fail to grow the necessary distance, or because of misdirected axonal growth. Efforts to repair peripheral nerve damage by surgical means has met with mixed results, particularly where damage extends over a significant distance. In some cases, the suturing steps used to obtain proper alignment of severed nerve ends stimulates the formulation of scar tissue which is thought to inhibit axon regeneration. Even where scar tissue formation has been reduced, as with the use of nerve guidance channels or other tubular prostheses, successful regeneration generally still is limited to nerve damage of less than 10 millimeters in distance. In addition, the reparative ability of peripheral neurons is significantly inhibited where an injury or neuropathy affects the cell body itself or results in extensive degeneration of a distal axon.

Mammalian neural pathways also are at risk due to damage caused by neoplastic lesions. Neoplasias of both the neurons and glial cells have been identified. Transformed cells of neural origin generally lose their ability to behave as normal differentiated cells and can destroy neural pathways by loss of function. In addition, the proliferating tumors may induce lesions by distorting normal nerve tissue structure, inhibiting pathways by compressing nerves, inhibiting cerbrospinal fluid or blood supply flow, and/or by stimulating the body's immune response. Metastatic tumors, which are a significant cause of neoplastic lesions in the brain and spinal cord, also similarly may damage neural pathways and induce neuronal cell death.

One type of morphoregulatory molecule associated with neuronal cell growth, differentiation and development is the cell adhesion molecule ("CAM"), most notably the nerve cell adhesion molecule (N-CAM). The CAMs are members the immunoglobulin super-family. They mediate cell—cell interactions in developing and adult tissues through homophilic binding, i.e., CAM—CAM binding on apposing cells. A number of different CAMs have been identified. Of these, the most thoroughly studied are N-CAM and L-CAM (liver cell adhesion molecules), both of which have been identified on all cells at early stages of development, as well as in different adult tissues. In neural tissue development, N-CAM expression is believed to be important in tissue organization, neuronal migration, nerve-muscle tissue adhesion, retinal formation, synaptogenesis, and neural degeneration. Reduced N-CAM expression also is thought to be associated with nerve dysfunction. For example, expression of at least one form of N-CAM, N-CAM-180, is reduced in a mouse demyelinating mutant. Bhat, *Brain Res.* 452: 373–377 (1988). Reduced levels of N-CAM also have been associated with normal pressure hydrocephalus, Werdelin, *Acta Neurol. Scand.* 79: 177–181 (1989), and with type II schizophrenia. Lyons, et al., *Biol. Psychiatry* 23: 769–775 (1988). In addition, antibodies against N-CAM have been shown to disrupt functional recovery in injured nerves. Remsen, *Exp. Neurobiol.* 110: 268–273 (1990).

Currently no satisfactory method exists to repair the damage caused by traumatic injuries of motor neurons and diseases of motor neurons.

There are 15,000 to 18,000 new cases of spinal cord injury each year in the United States. In addition, there are approximately 200,000 survivors of spinal cord injury. The annual cost of care for these patients exceeds $7 billion. The pathophysiology following acute spinal cord trauma is a complex and not fully understood mechanism. The primary tissue damage caused by mechanical trauma occurs immediately and is irreversible. Allen, *J. Am. Med. Assoc.* 57: 878–880 (1911). Experimental evidence indicates that much of the post-traumatic tissue damage is the result of a reactive process that begins within minutes after the injury and continues for days or weeks. Janssen, et al., *Spine* 14: 23–32 (1989) and Panter, et al., (1992). This progressive, self-destructive process includes pathophysiological mechanisms such as hemorrhage, post-traumatic ischemia, edema, axonal and neuronal necrosis, and demyelinization followed by cyst formation and infarction. For review, see Tator, et al., *J. Neurosurg,* 75: 15–26 (1991) and Faden, *Crit. Rev. Neurobiol.* 7: 175–186 (1993). Proposed injurious factors include electrolyte changes whereby increased intracellular calcium initiates a cascade of events (Young, *J. Neurotrauma* 9, Suppl. 1: S9–S25 (1992) and Young, *J. Emerg. Med* 11: 13–22 (1993)), biochemical changes with uncontrolled transmitter release (Liu, et al., *Cell* 66: 807–815 (1991) and Yanase, et al., *J. Neurosurg* 83: 884–888 (1995), arachidonic acid release, free-radical production, lipid peroxidation (Braughler, et al., *J. Neurotrauma* 9, Suppl. 1: S1–S7 (1992), eicosanoid production (Demediuk, et al., *J. Neurosci. Res.* 20: 115–121 (1988), endogenous opioids (Faden, et al., *Ann Neurol.* 17: 386–390 (1985), metabolic changes including alterations in oxygen and glucose (Faden, *Crit. Rev. Neurobiol.* 7: 175–186 (1993)), inflammatory changes (Blight, *J. Neurotrauma* 9, Suppl. 1: S83–S91 (1992), and astrocytic edema (Kimelberg, *J. Neurotrauma* 9, Suppl. 1: S71–S81 (1992). For the past 400 years surgical approaches including laminectomy and decompression, accompanied by fusion, have been the most commonly practiced treatment strategies. Hansebout, *"Early Management of Acute Spinal Cord Injury"*, pp. 181–196 (1982) and Janssen, et al., *Spine* 14: 23–32 (1989). However, these procedures have not involved the application of techniques to augment the regenerative properties of spinal cord tissue.

A host of diseases of motor neurons have been identified, including demyelinating diseases, myelopathies, and diseases of motor neurons such as amyotrophic lateral sclerosis (ALS). *INTERNAL MEDICINE,* ch. 121–123 (4th ed., J. H. Stein, ed., Mosby, 1994). Multiple sclerosis (MS) is the most common demyelinating disorder of the central nervous system, causing patches of sclerosis (i.e., plaques) in the brain and spinal cord. MS has protean clinical manifestations, depending upon the location and size of the plaque. Typical symptoms include visual loss, diplopia, nystagmus, dysarthria, weakness, paresthesias, bladder abnormalities, and mood alterations. Myriad treatments have been proposed for this long-term variable illness. The list of proposed treatments encompasses everything from diet to electrical stimulation to acupuncture, emotional support, and various forms of immunosupressive therapy. None have proved to be satisfactory.

Progressive loss of lower and upper motor neurons occurs in several diseases (e.g., primary lateral sclerosis, spinal muscular atrophy, benign focal amyotrophy). However, ALS is the most common form of motor neuron disease. Loss of both lower and upper motor neurons occur in ALS. Symptoms include progressive skeletal muscle wasting, weakness, gasciculations, and cramping. Some cases have predominant involvement of brainstem motoneurons (progressive bulbar palsy). Unfortunately, treatment of motor neuron and related diseas is largely supportive at this time. *INTERNAL MEDICINE,* ch. 123 (4th ed., J. H. Stein, ed., Mosby, 1994).

Accordingly, there is a need in the art for treatments of motor neurons disorders and injuries, and related deficits in neural functions.

SUMMARY OF THE INVENTION

The present invention provides methods and compositions for maintaining neural pathways in a mammal in vivo, including methods for enhancing the survival of neural cells.

In a preferred embodiment, methods of the invention for treating motor neuron defects, including amyotrophic lateral sclerosis, multiple sclerosis, and spinal cord injury comprise administering a morphogen comprising a dimeric protein having an amino acid sequence selected from the group consisting of a sequence have 70% homology with the C-terminal seven-cysteine skeleton of human OP-1 (amino acids 330–341 of SEQ ID NO:2), a sequence having greater than 60% amino acid sequence identity with human OP-1; generic sequence 7 (SEQ ID NO:4); generic sequence 8 (SEQ ID NO:6); generic sequence 10 (SEQ ID NO:7); and OPX (SEQ ID NO:3); wherein the morphogen stimulates production of N-CAM or L1 isoforms by an NG108-15 cell in vivo. Spinal cord injuries include injuries resulting from a tumor, mechanical trauma, and chemical trauma. The same or similar methods are contemplated to restore motor function in a mammal having amyotrophic lateral sclerosis, multiple sclerosis, or a spinal cord injury. Administering one of the aforementioned morphogens also provides a prophylactic function. Such administration has the effect of preserving motor function in a mammal having, or at risk of having, amyotrophic lateral sclerosis, multiple sclerosis, or a spinal cord injury. Also according to the invention, morphogen administration preserves the integrity of the nigrostriatal pathway.

Specifically, methods of the invention for treating (pre- or post-symptomatically) amyotrophic lateral sclerosis, multiple sclerosis, or a spinal cord injury comprise administering a morphogen selected from the group consisting of human OP-1, mouse OP-1, human OP-2, mouse OP-2, 60A, GDF-1, BMP2A, BMP2B, DPP, Vg1, Vgr-1, BMP3, BMP5, and BMP6. Such morphogens are capable of stimulating production of N-CAM or L1 isoform by an NG108-15 cell in vivo.

In a particularly-preferred embodiment, the morphogen is a soluble complex, comprising at least one morphogen pro domain, or fragment thereof, non-covalently attached to a mature morphogen.

In one aspect, the invention features compositions and therapeutic treatment methods comprising administering to a mammal a therapeutically effective amount of a morphogenic protein ("morphogen"), as defined herein, upon injury to a neural pathway, or in anticipation of such injury, for a time and at a concentration sufficient to maintain the neural pathway, including repairing damaged pathways, or inhibiting additional damage thereto.

In another aspect, the invention features compositions and therapeutic treatment methods for maintaining neural pathways. Such treatment methods include administering to the mammal, upon injury to a neural pathway or in anticipation of such injury, a compound that stimulates a therapeutically effective concentration of an endogenous morphogen. These compounds are referred to herein as morphogen-stimulating agents, and are understood to include substances which, when administered to a mammal, act on tissue(s) or organ(s) that normally are responsible for, or capable of, producing a morphogen and/or secreting a morphogen, and which cause endogenous level of the morphogen to be altered.

In particular, the invention provides methods for protecting neurons from the tissue destructive effects associated with the body's immune and inflammatory response to nerve injury. The invention also provides methods for stimulating neurons to maintain their differentiated phenotype, including inducing the redifferentiation of transformed cells of neuronal origin to a morphology characteristic of untransformed neurons. In one embodiment, the invention provides means for stimulating production of cell adhesion molecules, particularly nerve cell adhesion molecules (N-CAM). The invention also provides methods, compositions and devices for stimulating cellular repair of damaged neurons and neural pathways, including regenerating damaged dendrites or axons. In addition, the invention also provides means for evaluating the status of nerve tissue, and for detecting and monitoring neuropathies by monitoring fluctuations in morphogen levels.

In one aspect of the invention, the morphogens described herein are useful in repairing damaged neural pathways of the peripheral nervous system. In particular, morphogens are useful for repairing damaged neural pathways, including transected or otherwise damaged nerve fibers. Specifically, the morphogens described herein are capable of stimulating complete axonal nerve regeneration, including vascularization and reformation of the myelin sheath. Preferably, the morphogen preferably is provided to the site of injury in a biocompatible, bioresorbable carrier capable of maintaining the morphogen at the site and, where necessary, means for directing axonal growth from the proximal to the distal ends of a severed neuron. For example, means for directing axonal growth may be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic or polybutyric acids and/or copolymers thereof. A preferred carrier comprises an extracellular matrix composition derived, for example, from mouse sarcoma cells.

In a particularly preferred embodiment, a morphogen is disposed in a nerve guidance channel which spans the distance of the damaged pathway. The channel acts both as a protective covering and a physical means for guiding growth of a neurite. Useful channels comprise a biocompatible membrane, which may be tubular in structure, having a dimension sufficient to span the gap in the nerve to be repaired, and having openings adapted to receive severed nerve ends. The membrane may be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In a preferred embodiment, the outer surface of the channel is substantially impermeable.

The morphogen may be disposed in the channel in association with a biocompatible carrier material, or it may be adsorbed to or otherwise associated with the inner surface of the casing, such as is described in U.S. Pat. No. 5,011,486, provided that the morphogen is accessible to the severed nerve ends.

Morphogens described herein are also useful in autologous peripheral nerve segment implants, such as in the repair of damaged or detached retinas, or other damage to the optic nerve.

In another aspect of the invention, morphogens described herein are useful to protect against damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of a morphogen, either directly or systemically alleviate and/or inhibit the immunologically related response to a neural injury. Alternatively, administration of an agent capable of stimulating morphogen expression and/or secretion in vivo, preferably at the site of injury, may also be used. Where the injury is to be induced, as during surgery or other aggressive clinical treatment, the morphogen or agent may be provided prior to induction of the injury to provide a neuroprotective effect to the nerve tissue at risk.

Generally, morphogens useful in methods and compositions of the invention are dimeric proteins that induce morphogenesis of one or more eukaryotic (e.g., mammalian) cells, tissues or organs. Tissue morphogenesis includes de novo or regenerative tissue formation, such as occurs in a vertebrate embryo during development. Of particular interest are morphogens that induce tissue-specific morphogenesis at least of bone or neural tissue. As defined herein, a morphogen comprises a pair of polypeptides that, when folded, form a dimeric protein that elicits morphogenetic responses in cells and tissues displaying morphogen-specific receptors. That is, the morphogens generally induce a cascade of events including all of the following in a morphogenically permissive environment: stimulating proliferation of progenitor cells; stimulating the differentiation of progenitor cells; stimulating the proliferation of differentiated cells; and, supporting the growth and maintenance of differentiated cells. "Progenitor" cells are uncommitted cells that are competent to differentiate into one or more specific types of differentiated cells, depending on their genomic repertoire and the tissue specificity of the permissive environment in which morphogenesis is induced. An exemplary progenitor cell is a hematopoeitic stem cell, a mesenchymal stem cell, a basement epithelium cell, a neural crest cell, or the like. Further, morphogens can delay or mitigate the onset of senescence- or quiescence-associated loss of phenotype and/or tissue function. Still further, morphogens can stimulate phenotypic expression of a differentiated cell type, including expression of metabolic and/or functional, e.g., secretory, properties thereof. In addition, morphogens can induce redifferentiation of committed cells (e.g., osteoblasts, neuroblasts, or the like) under appropriate conditions. As noted above, morphogens that induce proliferation and/or differentiation at least of bone or neural tissue, and/or support the growth, maintenance and/or functional properties of neural tissue, are of particular interest herein. See, e.g., WO 92/15323, WO 93/04692, WO 94/03200 (providing more detailed disclosures as to the tissue morphogenic properties of these proteins).

As used herein, the terms "morphogen," "bone morphogen," "bone morphogenic protein," "BMP," "morphogenic protein" and "morphogenetic protein" all embrace the class of proteins typified by human osteogenic protein 1 (hOP-1). Nucleotide and amino acid sequences for hOP-1 are provided in SEQ ID NOS:1 and 2, respectively. For ease of description, hOP-1 is considered a representative morphogen. It will be appreciated that OP-1 is merely representative of the TGF-β subclass of true tissue morphogens and is not intended to limit the description. Other known and useful morphogens include, but are not limited to, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, 60A, NODAL, UNIVIN, SCREW, ADMP, and NEURAL, and morphogenically-active amino acid variants of any thereof.

In specific embodiments, useful morphogens include those sharing the conserved seven cysteine skeleton, and sharing at least 70% amino acid sequence homology (similarity), within the C-terminal seven-cysteine skeleton of human OP-1, residues 330–431 of SEQ ID NO:2 (hereinafter referred to as the "reference sequence"). In another embodiment, the invention encompasses use of biologically active species (phylogenetic) variants of any of the morphogenic proteins recited herein, including conservative amino acid sequence variants, proteins encoded by degenerate nucleotide sequence variants, and morphogenically-active proteins sharing the conserved seven cysteine skeleton as defined herein and encoded by a DNA competent to hybridize under standard stringency conditions to a DNA encoding a morphogenic protein disclosed herein, including, without limitation, OP-1 or BMP-2 or BMP-4. Presently, however, the reference sequence is that of residues 330–431 of SEQ ID NO:2 (OP-1).

In still another embodiment, morphogens useful in methods and compositions of the invention are defined as morphogenically-active proteins having any one of the generic sequences defined herein, including OPX (SEQ ID NO:3) and Generic Sequences 7 and 8 (SEQ ID NOS:4 and 5, respectively), or Generic Sequences 9 and 10 (SEQ ID NOS:6 and 7, respectively). OPX encompasses the observed variation between the known phylogenetic counterparts of the osteogenic OP-1 and OP-2 proteins, and is described by the amino acid sequence presented herein below and in SEQ ID NO:3. Generic Sequence 9 is a 96 amino acid sequence containing the C-terminal six cysteine skeleton observed in hOP-1 (residues 335–431 of SEQ ID NO:2) and wherein the remaining residues encompass the observed variation among OP-1, OP-2, OP-3, BMP-2, BMP-3, BMP-4, BMP-5, BMP-6, BMP-8, BMP-9, BMP-10, BMP-11, BMP-15, GDF-1, GDF-3, GDF-5, GDF-6, GDF-7, GDF-8, GDF-9, GDF-10, GDF-11, 60A, UNIVIN, NODAL, DORSALIN, NEURAL, SCREW and ADMP. That is, each of the non-cysteine residues is independently selected from the corresponding residue in this recited group of known, naturally-sourced proteins. Generic Sequence 10 is a 102 amino acid sequence which includes a five amino acid sequence added to the N-terminus of the Generic Sequence 9 and defines the seven cysteine skeleton observed in hOP-1 (330–431 SEQ ID NO:2). Generic Sequences 7 and 8 are 96 and 102 amino acid sequences, respectively, containing either the six cysteine skeleton (Generic Sequence 7) or the seven cysteine skeleton (Generic Sequence 8) defined by hOP-1 and wherein the remaining non-cysteine residues encompass the observed variation among OP-1, OP-2, OP-3, BMP-2, BMP-3, BMP-4, 60A, DPP, Vg1, BMP-5, BMP-6, Vgr-1, and GDF-1.

Of particular interest are morphogens which, when provided to a specific tissue of a mammal, induce tissue-specific morphogenesis or maintain the normal state of differentiation and growth of that tissue. In preferred embodiments, the present morphogens induce the formation of vertebrate (e.g., avian or mammalian) body tissues, such as but not limited to nerve, eye, bone, cartilage, bone marrow, ligament, tooth dentin, periodontium, liver, kidney, lung, heart, or gastrointestinal lining. Preferred methods may be carried out in the context of developing embryonic tissue, or at an aseptic, unscarred wound site in post-embryonic tissue. Methods of identifying such morphogens, or morphogen receptor agonists, are known in the art and include assays for compounds which induce morphogen-mediated responses (e.g., induction of endochondral bone formation, induction of differentiation of metanephric mesenchyme, and the like). In a preferred embodiment, morphogens of the invention, when implanted in a mammal in conjunction with a matrix permissive of bone morphogenesis, are capable of inducing a developmental cascade of cellular and molecular events that culminates in endochondral bone formation. See, U.S. Pat. No. 4,968,590; Sampath, et al., *Proc. Natl. Acad. Sci. USA* 80: 6591–6595 (1983), the disclosures of which are incorporated by reference herein.

In an alternative preferred embodiment, morphogens of the invention are also capable of stimulating production of cell adhesion molecules, including nerve cell adhesion molecules (N-CAMs). In a preferred embodiment, the present morphogens are capable of stimulating the production of N-CAM in vitro in NG108-15 cells, which are a preferred model system for assessing neuronal differentiation, particularly motor neuron differentiation.

In still other embodiments, an agent which acts as an agonist of a morphogen receptor may be administered instead of the morphogen itself. An "agonist" of a receptor is a compound which binds to the receptor, and for which the result of such binding is similar to the result of binding the natural, endogenous ligand of the receptor. That is, the compound must, upon interaction with the receptor, produce the same or substantially similar transmembrane and/or intracellular effects as the endogenous ligand. Thus, an agonist of a morphogen receptor binds to the receptor and such binding has the same or a functionally similar result as morphogen binding (e.g., induction of morphogenesis). The activity or potency of an agonist can be less than that of the natural ligand, in which case the agonist is said to be a "partial agonist," or it can be equal to or greater than that of the natural ligand, in which case it is said to be a "full agonist." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Such an agonist may also be referred to as a morphogen "mimic," "mimetic," or "analog."

Morphogen inducers and agonists can be identified by mutation, site-specific mutagenesis, combinatorial chemistry, etc. Such methods are well known in the art. For example, methods of identifying morphogen inducers or agonists of morphogen receptors may be found in U.S. Pat. No. 08/478,097 filed Jun. 7, 1995 now U.S. Pat. No. 6,040,431 and U.S. Pat. No. 08/507,598 filed Jul. 26, 1995, now U.S. Pat. No. 5,834,188 the disclosures of which are incorporated herein by reference. Candidate morphogen inducers and agonists are then tested for their ability to induce endochondral bone formation and preferably, to stimulate N-CAM production in neurons or in a neuronal model system, such as NG108-15 cells. Morphogen inducers and agonists identified according to the present invention are capable of inducing endochondral bone formation when implanted in a mammal in conjunction with a matrix permissive of bone morphogenesis and are capable of stimulating production of N-CAM in vitro.

The preferred methods, material, and examples that will now be described are illustrative only and are not intended to be limiting. Other features and advantages of the invention will be apparent from the following detailed description, and from the claims.

BRIEF DESCRIPTION OF THE DRAWINGS

FIG. 1 is a tabular presentation of the percent amino acid sequence identity and percent amino acid sequence homology ("similarity") that various members of the family of morphogenic proteins as defined herein share with hOP-1 in the C-terminal seven cysteine skeleton;

DETAILED DESCRIPTION OF THE INVENTION

Figure 2A:
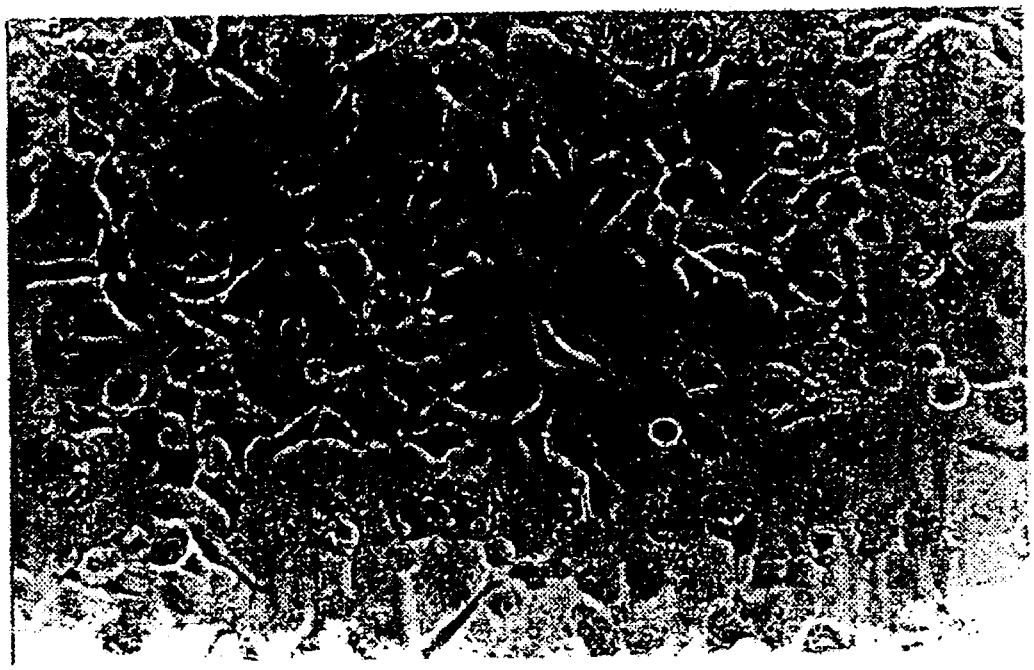
FIG. 2 (Panels A and B) are photographs illustrating the ability of morphogen (OP-1) to induce transformed neuroblastoma xglioma cells (Panel 1A) to redifferentiate to a morphology characteristic of untransformed neurons (Panel 1B)

It has now been discovered that morphogens enhance survival of neurons, and maintain neural pathways. As described herein, morphogens are capable of enhancing survival of neurons, stimulating neuronal CAM expression, maintaining the phenotypic expression of differentiated neurons, inducing the redifferentiation of transformed cells of neural origin, and stimulating axonal growth over breaks in neural processes, particularly large gaps in axons. Morphogens also protect against tissue destruction associated with immunologically-related nerve tissue damage. Finally, morphogens may be used as part of a method for monitoring the viability of nerve tissue in a mammal.

A. Biochemical, Structural and Functional Properties of Useful Morphogenic Proteins As noted above, a protein is morphogenic as defined herein if it induces the developmental cascade of cellular and molecular events that culminate in the formation of new, organ-specific tissue. In a preferred embodiment, a morphogen is a dimeric protein, each polypeptide component of which has a sequence that corresponds to, or is functionally equivalent to, at least the conserved C-terminal six or seven cysteine skeleton of human OP-1, included in SEQ ID NO:2, and/or which shares 70% amino acid sequence homology with OP1 in this region. The morphogens are generally competent to induce a cascade of events including the following, in a morphogenically permissive environment: stimulating proliferation of progenitor cells; stimulating the differentiation of progenitor cells; stimulating the proliferation of differentiated cells; and supporting the growth and maintenance of differentiated cells. Under appropriate conditions morphogens are also competent to induce redifferentiation of cells that have undergone abnormal differentiation. Details of how the morphogens useful in this invention were identified, as well as a description on how to make, use and test them for morphogenic activity are disclosed in numerous publications, including U.S. Pat. Nos. 5,011,691 and 5,266,683, and the international patent application publications WO 92/15323; WO 93/04692; and WO 94/03200, each of which are incorporated by reference herein. As disclosed therein, the morphogens can be purified from naturally-sourced material or recombinantly produced from prokaryotic or eukaryotic host cells, using the genetic sequences disclosed therein. Alternatively, novel morphogenic sequences can be identified following the procedures disclosed therein.

The naturally-occurring morphogens share substantial amino acid sequence homology in their C-terminal sequences (sharing e.g., a six or seven cysteine skeleton sequence). Typically, a naturally-occurring morphogen is translated as a precursor, having an N-terminal signal peptide sequence, typically less than about 35 residues in length, followed by a "pro" domain that is cleaved to yield the mature polypeptide, which includes the biologically active C-terminal skeleton sequence. The signal peptide is cleaved rapidly upon translation, at a cleavage site that can be predicted in a given sequence using the method of Von Heijne, *Nucleic Acids Research* 14: 4683–4691 (1986). The pro polypeptide typically is about three times larger than the fully processed, mature C-terminal polypeptide. Under native conditions, the protein is secreted as a mature dimer and the cleaved pro polypeptide is thought to remain associated therewith to form a protein complex, presumably to improve the solubility of the mature dimeric protein. The complexed form of a morphogen is generally observed to be more soluble than the mature form under physiological conditions.

Natural-sourced morphogenic protein in its mature, native form, is typically a glycosylated dimer, having an apparent molecular weight of about 30–36 kDa as determined by SDS-PAGE. When reduced, the 30 kDa protein gives rise to two glycosylated polypeptide subunits having apparent molecular weights in the range of about 16 kDa and about 18 kDa. The unglycosylated dimeric protein, which also has morphogenic activity, typically has an apparent molecular weight in the range of about 27 kDa. When reduced, the 27 kDa protein gives rise to two unglycosylated polypeptides having molecular weights typically in the range of about 14 kDa to about 16 kDa.

In preferred embodiments, each of the polypeptide subunits of a dimeric morphogenic protein as defined herein comprises an amino acid sequence sharing a defined relationship with an amino acid sequence of a reference morphogen. In one embodiment, preferred morphogenic polypeptide chains share a defined relationship with a sequence present in morphogenically-active human OP-1, SEQ ID NO:2. However, any one or more of the naturally-occurring or biosynthetic morphogenic proteins disclosed herein similarly could be used as a reference sequence. Preferred morphogenic polypeptide chains share a defined relationship with at least the C-terminal six cysteine skeleton of human OP-1, residues 335–431 of SEQ ID NO:2. Preferably, morphogenic proteins share a defined relationship with at least the C-terminal seven cysteine skeleton of human OP-1, residues 330–431 of SEQ ID NO:2.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. For example naturally-occurring morphogens have been described in which at least one internal deletion (of one residue; BMP2) or insertion (of four residues; GDF-1) is present but does not abrogate biological activity. Functionally equivalent sequences further include those wherein one or more amino acid residues differ from the corresponding residue of a reference sequence, e.g., the C-terminal seven cysteine skeleton of human OP-1, provided that this difference does not destroy tissue morphogenic activity. Accordingly, conservative substitutions of corresponding amino acids in the reference sequence are preferred. Amino acid residues that are "conservative substitutions" for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff, et al., 5 *ATLAS OF PROTEIN SEQUENCE AND STRUCTURE*, Suppl. 3, ch. 22 pp. 354–352 (1978), Natl. Biomed. Res. Found., Washington, D.C. 20007, the teachings of which are incorporated by reference herein. Examples of conservative substitutions include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative substitution" also includes the use of a synthetic or derivatized amino acid in place of the corresponding natural parent amino acid, provided that antibodies raised to the resulting variant polypeptide also immunoreact with the corresponding naturally sourced morphogen polypeptide.

The following publications disclose publications morphogen polypeptide sequences, as well as relevant chemical and physical properties, of naturally-occurring and/or synthetic morphogens: OP-1 and OP-2: U.S. Pat. Nos. 5,011,691, 5,266,683, Ozkaynak, et al., *EMBO J.* 9: 2085–2093 (1990); OP-3: WO 94/10203 (PCT US93/10520); BMP-2, BMP-3, and BMP-4: WO 88/00205, Wozney, et al., *Science* 242: 1528–1534 (1988); BMP-5 and BMP-6: Celeste, et al., *PNAS* 87: 9843–9847 (1991); Vgr-1: Lyons, et al., *PNAS* 86: 4554–4558 (1989); DPP: Padgett, et al., *Nature* 325: 81–84 (1987); Vg-1: Weeks *Cell* 51: 861–867 (1987); BMP-9: WO 95/33830 (PCT/US95/07084); BMP-10: WO 94/26893 (PCT/US94/05290); BMP-11: WO 94/26892 (PCT/US94/05288); BMP-12: WO 95/16035 (PCT/US94/14030); BMP-13: WO 95/16035 (PCT/US94/14030); GDF-1: WO 92/00382 (PCT/US91/04096) and Lee, et al., *PNAS* 88: 4250–4254 (1991); GDF-8: WO 94/21681 (PCT/US94/03019); GDF-9: WO 94/15966 (PCT/US94/00685); GDF-10: WO 95/10539 (PCT/US94/11440); GDF-11: WO 96/01845 (PCT/US95/08543); BMP-15: WO 96/36710 (PCT/US96/06540); MP121: WO 96/01316 (PCT/EP95/02552); GDF-5 (CDMP-1, MP52): WO 94/15949 (PCT/US94/00657) and WO 96/14335 (PCT/US94/12814) and WO 93/16099 (PCT/EP93/00350); GDF-6 (CDMP-2, BMP-13): WO 95/01801 (PCT/US94/07762) and WO 96/14335 and WO 95/10635 (PCT/US94/14030); GDF-7 (CDMP-3, BMP-12): WO 95/10802 (PCT/US94/07799) and WO 95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In certain preferred embodiments, useful morphogenic proteins include those in which the amino acid sequences comprise a sequence sharing at least 70% amino acid sequence homology or "similarity", and preferably 80% homology or similarity, with a reference morphogenic protein selected from the exemplary, naturally-occurring morphogenic proteins listed herein. Preferably, the reference protein is human OP-1, and the reference sequence thereof is the C-terminal seven cysteine skeleton present in osteogenically active forms of human OP-1, residues 330–431 of SEQ ID NO:2. Useful morphogenic proteins accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins including those set forth and identified above. Certain particularly preferred morphogenic polypeptides share at least 60% amino acid identity with the preferred reference sequence of human OP-1, still more preferably at least 65% amino acid identity therewith.

In certain embodiments, a polypeptide suspected of being functionally equivalent to a reference morphogen polypeptide is aligned therewith using the method of Needleman, et al., *J. Mol. Biol.* 48: 443–453 (1970), implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology, or identity, between the candidate and reference sequences. "Amino acid sequence homology" is understood herein to include both amino acid sequence identity and similarity. Homologous sequences share identical and/or similar amino acid residues, where similar residues are conservation substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a preferred embodiment, the reference sequence is the C-terminal seven cysteine skeleton sequence of human OP-1.

FIG. 1 recites the percent amino acid sequence homology (similarity) and percent identity within the C-terminal seven cysteine skeletons of various representative members of the TGF-β family, using OP1 as the reference sequence. The percent homologies recited in the figure are determined by aligning the sequences essentially following the method of Needleman, et al., *J. Mol. Biol.*, 48: 443–453 (1970), and using the Align Program (DNAstar, Inc.). Insertions and deletions from the reference morphogen sequence (the C-terminal, biologically active seven-cysteine skeleton of hOP-1) are ignored for purposes of calculation.

As is apparent to one of ordinary skill in the art reviewing the sequences for the proteins listed in FIG. 1, significant amino acid changes can be made from the reference sequence while retaining substantial morphogenic activity. For example, while the GDF-1 protein sequence shares only about 50% amino acid identity with the hOP-1 sequence described herein, the GDF-1 sequence shares greater than 70% amino acid sequence homology with the hOP-1 sequence, where "homology" is as defined above. Moreover, GDF-1 contains a four amino acid insert (Gly-Gly-Pro-Pro) between the two residues corresponding to residue 372 and 373 of OP-1 (SEQ ID NO:2). Similarly, BMP-3 has a "extra" residue, a valine, inserted between the two residues corresponding to residues 385 and 386 of hOP-1 (SEQ ID NO:2). Also, BMP-2 and BMP-4 are both "missing" the amino acid residue corresponding to residue 389 of OP1 (SEQ ID NO:2). None of these "deviations" from the reference sequence appear to interfere substantially with biological activity.

In other preferred embodiments, the family of morphogenic polypeptides useful in the present invention, and members thereof, are defined by a generic amino acid sequence. For example, Generic Sequence 7 (SEQ ID NO:4) and Generic Sequence 8 (SEQ ID NO:5) disclosed below, encompass the observed variations between preferred protein family members identified to date, including at least OP-1, OP-2, OP-3, CBMP-2A, CBMP-2B, BMP-3, 60A, DPP, Vg1, BMP-5, BMP-6, Vgr-1, and GDF-1. The amino acid sequences for these proteins are described herein and/or in the art, as summarized above. The generic sequences include both the amino acid identity shared by these sequences in the C-terminal skeleton, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 36 (Generic Sequence 7) or position 41 (Generic Sequence 8), thereby encompassing the morphogenically-active sequences of OP-2 and OP-3.

```
          Generic Sequence 7 (SEQ ID NO: 4)

Leu Xaa Xaa Xaa Phe Xaa Xaa
               1               5
    Xaa Gly Trp Xaa Xaa Xaa Xaa Xaa Xaa Pro
              10                  15
    Xaa Xaa Xaa Xaa Ala Xaa Tyr Cys Xaa Gly
              20                  25
    Xaa Cys Xaa Xaa Pro Xaa Xaa Xaa Xaa Xaa
              30                  35
    Xaa Xaa Xaa Asn His Ala Xaa Xaa Xaa Xaa
              40                  45
    Xaa Xaa Xaa Xaa Xaa Xaa Xaa Xaa Xaa Xaa
              50                  55
    Xaa Xaa Xaa Cys Cys Xaa Pro Xaa Xaa Xaa
              60                  65
    Xaa Xaa Xaa Xaa Xaa Leu Xaa Xaa Xaa Xaa
              70                  75
    Xaa Xaa Xaa Val Xaa Leu Xaa Xaa Xaa Xaa
              80                  85
    Xaa Met Xaa Val Xaa Xaa Cys Xaa Cys Xaa
              90                  95
``` wherein each Xaa independently is selected from a group of one or more specified amino acids defined as follows. "Res." means "residue" and Xaa at res. 2=(Tyr or Lys); Xaa at res. 3=Val or Ilc); Xaa at res. 4=(Ser, Asp or Glu); Xaa at res. 6=(Arg, Gln, Ser, Lys or Ala); Xaa at res. 7=(Asp or Glu); Xaa at res. 8=(Leu, Val or Ile); Xaa at res. 11=(Gln, Leu, Asp, His, Asn or Ser); Xaa at res. 12=(Asp, Arg, Asn or Glu); Xaa at res. 13=(Trp or Ser); Xaa at res. 14=(Ile or Val); Xaa at res. 15=(Ile or Val); Xaa at res. 16 (Ala or Ser); Xaa at res. 18=(Glu, Gln, Leu, Lys, Pro or Arg); Xaa at res. 19=(Gly or Ser); Xaa at res. 20=(Tyr or Phe); Xaa at res. 21=(Ala, Ser, Asp, Met, His, Gln, Leu or Gly); Xaa at res. 23=(Tyr, Asn or Phe); Xaa at res. 26=(Glu, His, Tyr, Asp, Gln, Ala or Ser); Xaa at res. 28=(Glu, Lys, Asp, Gln or Ala); Xaa at res. 30=(Ala, Ser, Pro, Gln, Ile or Asn) Xaa at res. 31=(Phe, Leu or Tyr); Xaa at res. 33=(Leu, Val or Met); Xaa at res.

34=(Asn, Asp, Ala, Thr or Pro); Xaa at res. 35=(Ser, Asp, Glu, Leu, Ala or Lys); Xaa at res. 36=(Tyr, Cys, His, Ser or Ile); Xaa at res. 37=(Met, Phe, Gly or Leu); Xaa at res. 38=(Asn, Ser or Lys); Xaa at res. 39=(Ala, Ser, Gly or Pro); Xaa at res. 40=(Thr, Leu or Ser); Xaa at res. 44=(Ile, Val or Thr); Xaa at res. 45=(Val, Leu, Met or Ile); Xaa at res. 46=(Gln or Arg); Xaa at res. 47=(Thr, Ala or Ser); Xaa at res. 48=(Leu or Ile); Xaa at res. 49=(Val or Met); Xaa at res. 50=(His, Asn or Arg); Xaa at res. 51=(Phe, Leu, Asn, Ser, Ala or Val); Xaa at res. 52=(Ile, Met, Asn, Ala, Val, Gly or Leu); Xaa at res. 53=(Asn, Lys, Ala, Glu, Gly or Phe); Xaa at res. 54=(Pro, Ser or Val); Xaa at res. 55=(Glu, Asp, Asn, Gly, Val, Pro or Lys); Xaa at res. 56=(Thr, Ala, Val, Lys, Asp, Tyr, Ser, Gly, Ile or His); Xaa at res. 57=(Val, Ala or Ile); Xaa at res. 58=(Pro or Asp); Xaa at res. 59=(Lys, Leu or Glu); Xaa at res. 60=(Pro, Val or Ala); Xaa at res. 63=(Ala or Val); Xaa at res. 65=(Thr, Ala or Glu); Xaa at res. 66=(Gln, Lys, Arg or Glu); Xaa at res. 67=(Leu, Met or Val); Xaa at res. 68=(Asn, Ser, Asp or Gly); Xaa at res. 69=(Ala, Pro or Ser); Xaa at res. 70=(Ile, Thr, Val or Leu); Xaa at res. 71=(Ser, Ala or Pro); Xaa at res. 72=(Val, Leu, Met or Ile); Xaa at res. 74=(Tyr or Phe); Xaa at res. 75=(Phe, Tyr, Leu or His); Xaa at res. 76=(Asp, Asn or Leu); Xaa at res. 77=(Asp, Glu, Asn, Arg or Ser); Xaa at res. 78=(Ser, Gln, Asn, Tyr or Asp); Xaa at res. 79=(Ser, Asn, Asp, Glu or Lys); Xaa at res. 80=(Asn, Thr or Lys); Xaa at res. 82=(Ile, Val or Asn); Xaa at res. 84=(Lys or Arg); Xaa at res. 85=(Lys, Asn, Gln, His, Arg or Val); Xaa at res. 86=(Tyr, Glu or His); Xaa at res. 87=(Arg, Gln, Glu or Pro); Xaa at res. 88=(Asn, Glu, Trp or Asp); Xaa at res. 90=(Val, Thr, Ala or Ile); Xaa at res. 92=(Arg, Lys, Val, Asp, Gln or Glu); Xaa at res. 93=(Ala, Gly, Glu or Ser); Xaa at res. 95=(Gly or Ala) and Xaa at res. 97=(His or Arg).

Generic Sequence 8 (SEQ ID NO:5) includes all of Generic Sequence 7 (SEQ ID NO:4) and in addition includes the following sequence (SEQ ID NO:8) at its N-terminus:

| SEQ ID NO: 8 |
| --- |
| Cys Xaa Xaa Xaa Xaa |
| 1               5 |

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res. 2=(Tyr or Lys)" in Generic Sequence 7 refers to Xaa at res. 7 in Generic Sequence 8. In Generic Sequence 8, Xaa at res. 2=(Lys, Arg, Ala or Gln); Xaa at res. 3=(Lys, Arg or Met); Xaa at res. 4=(His, Arg or Gln); and Xaa at res. 5=(Glu, Ser, His, Gly, Arg, Pro, Thr, or Tyr).

In another embodiment, useful osteogenic proteins include those defined by Generic Sequences 9 and 10 (SEQ ID NOS:6 and 7, respectively), described herein above. Specifically, Generic Sequences 9 and 10 are composite amino acid sequences of the following proteins: human OP-1, human OP-2, human OP-3, human BMP-2, human BMP-3, human BMP-4, human BMP-5, human BMP-6, human BMP-8, human BMP-9, human BMP-10, human BMP-11, Drosophila 60A, Xenopus Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, Drosophila dpp, Drosophila SCREW, mouse NODAL, mouse GDF-8, human GDF-8, mouse GDF-9, mouse GDF-10, human GDF-11, mouse GDF-11, human BMP-15, and rat BMP-3b. Like Generic Sequence 7, Generic Sequence 9 accommodates the C-terminal six cysteine skeleton and, like Generic Sequence 8, Generic Sequence 10 accommodates the seven cysteine skeleton.

| Generic Sequence 9 (SEQ ID NO: 6) |
| --- |
| Xaa Xaa Xaa Xaa Xaa Xaa Xaa Xaa Xaa Xaa |
| 1          5          10 |
| Xaa Xaa Xaa Xaa Xaa Xaa Pro Xaa Xaa Xaa |
| 15          20 |
| Xaa Xaa Xaa Xaa Cys Xaa Gly Xaa Cys Xaa |
| 25          30 |
| Xaa Xaa Xaa Xaa Xaa Xaa Xaa Xaa Xaa Xaa |
| 35          40 |
| Xaa Xaa Xaa Xaa Xaa Xaa Xaa Xaa Xaa Xaa |
| 45          50 |
| Xaa Xaa Xaa Xaa Xaa Xaa Xaa Xaa Xaa Xaa |
| 55          60 |
| Xaa Cys Xaa Pro Xaa Xaa Xaa Xaa Xaa Xaa |
| 65          70 |
| Xaa Xaa Leu Xaa Xaa Xaa Xaa Xaa Xaa Xaa |
| 75          80 |
| Xaa Xaa Xaa Xaa Xaa Xaa Xaa Xaa Xaa Xaa |
| 85          90 |
| Xaa Xaa Xaa Cys Xaa Cys Xaa |
| 95 | wherein each Xaa is independently selected from a group of one or more specified amino acids defined as follows: "Res." means "reside" and Xaa at res. 1=(Phe, Leu or Glu); Xaa at res. 2=(Tyr, Phe, His, Arg, Thr, Lys, Gln, Val or Glu); Xaa at res. 3=(Val, Ile, Leu or Asp); Xaa at res. 4=(Ser, Asp, Glu, Asn or Phe); Xaa at res. 5=(Phe or Glu); Xaa at res. 6=(Arg, Gln, Lys, Ser, Glu, Ala or Asn); Xaa at res. 7=(Asp, Glu, Leu, Ala or Gln); Xaa at res. 8=(Leu, Val, Met, Ile or Phe); Xaa at res. 9=(Gly, His or Lys); Xaa at res. 10=(Trp or Met); Xaa at res. 11=(Gln, Leu, His, Glu, Asn, Asp, Ser or Gly); Xaa at res. 12=(Asp, Asn, Ser, Lys, Arg, Cgu or His); Xaa at res. 13=(Trp or Ser); Xaa at res. 14=(Ile or Val); Xaa at res. 15=(Ile or Val); Xaa at res. 16=(Ala, Ser, Tyr or Trp); Xaa at res. 18=(Glu, Lys, Gln, Met, Pro, Leu, Arg, His or Lys); Xaa at res. 19=(Gly, Glu, Asp, Lys, Ser, Gln, Arg or Phe); Xaa at res. 20=(Tyr or Phe); Xaa at res. 21=(Ala, Ser, Gly, Met, Gln, His, Glu, Asp Leu, Asn, Lys or Thr); Xaa at res. 22=(Ala or Pro); Xaa at res. 23=(Tyr, Phe, Asn, Ala or Arg); Xaa at res. 24=(Tyr, His, Glu, Phe or Arg); Xaa at res. 26=(Glu, Asp, Ala, Ser, Tyr, His, Lys, Arg, Gln or Gly); Xaa at res. 28=(Glu, Asp, Leu, Val, Lys, Gly, Thr, Ala or Gln); Xaa at res. 30=(Ala, Ser, Ile, Asn, Pro, Glu, Asp, Phe, Gln or Leu); Xaa at res. 31=(Phe, Tyr, Leu, Asn, Gly or Arg); Xaa at res. 32=(Pro, Ser, Ala or Val); Xaa at res. 33=(Leu, Met, Glu, Phe or Val); Xaa at res. 34=(Asn, Asp, Thr, Gly, Ala, Arg, Leu or Pro); Xaa at res. 35=(Ser, Ala, Glu, Asp, Thr, Leu, Lys, Gln or His); Xaa at res. 36=(Tyr, His, Cys, Ile, Arg, Asp, Asn, Lys, Ser, Glu or Gly); Xaa at res. 37=(Met, Leu, Phe, Val, Gly or Tyr); Xaa at res. 38=(Asn, Glu, Thr, Pro, Lys, His, Gly, Met, Val or Arg); Xaa at res. 39=(Ala, Ser, Gly, Pro or Phe); Xaa at res. 40=(Thr, Ser, Leu, Pro, His or Met); Xaa at res. 41=(Asn, Lys, Val, Thr or Gln); Xaa at res. 42=(His, Tyr or Lys); Xaa at res. 43=(Ala, Thr, Leu or Tyr); Xaa at res. 44=(Ile, Thr, Val, Phe, Tyr, Met or Pro); Xaa at res. 45=(Val, Leu, Met, Ile or His); Xaa at res. 46=(Gln, Arg or Thr); Xaa at res. 47=(Thr, Ser, Ala, Asn or His); Xaa at res. 48=(Leu, Asn or Ile); Xaa at res. 49=(Val, Met, Leu, Pro or Ile); Xaa at res. 50=(His, Asn, Arg, Lys, Tyr or Gln); Xaa at res. 51=(Phe, Leu, Ser, Asn, Met, Ala, Arg, Glu, Gly or Gln); Xaa at res. 52=(Ile, Met, Leu, Val, Lys, Gln, Ala or Tyr); Xaa at res. 53=(Asn, Phe, Lys, Glu, Asp, Ala, Gln, Gly, Leu or Val); Xaa at res. 54=(Pro, Asn, Ser, Val or Asp); Xaa at res. 55=(Glu, Asp, Asn, Lys, Arg, Ser, Gly, Thr, Gln, Pro or His); Xaa at res. 56=(Thr, His, Tyr, Ala, Ile, Lys, Asp, Ser, Gly or Arg); Xaa at res. 57=(Val, Ile, Thr, Ala, Leu or Ser); Xaa at res. 58=(Pro, Gly, Ser, Asp or Ala); Xaa at res. 59=(Lys, Leu, Pro, Ala, Ser, Glu, Arg or Gly); Xaa at res. 60=(Pro, Ala, Val, Thr or Ser); Xaa at res. 61=(Cys, Val or Ser); Xaa at res. 63=(Ala, Val or Thr); Xaa at res. 65=(Thr, Ala, Glu, Val, Gly, Asp or Tyr); Xaa at res. 66=(Gln, Lys, Glu, Arg or Val); Xaa at res. 67=(Leu, Met, Thr or Tyr); Xaa at res. 68=(Asn, Ser, Gly, Thr, Asp, Glu, Lys or Val); Xaa at res. 69=(Ala, Pro, Gly or Ser); Xaa at res. 70=(Ile, Thr, Leu or Val); Xaa at res. 71=(Ser, Pro, Ala, Thr, Asn or Gly); Xaa at res. 2=(Val, Ile, Leu or Met); Xaa at res. 74=(Tyr, Phe, Arg, Thr, Tyr or Met); Xaa at res. 75=(Phe, Tyr, His, Leu, Ile, Lys, Gln or Val); Xaa at res. 76=(Asp, Leu, Asn or Glu); Xaa at res. 77=(Asp, Ser, Arg, Asn, Glu, Ala, Lys, Gly or Pro); Xaa at res. 78=(Ser, Asn, Asp, Tyr, Ala, Gly, Gln, Met, Glu, Asn or Lys); Xaa at res. 79=(Ser, Asn, Glu, Asp, Val, Lys, Gly, Gln or Arg); Xaa at res. 80=(Asn, Lys, Thr, Pro, Val, Ile, Arg, Ser or Gln); Xaa at res. 81=(Val, Ile, Thr or Ala); Xaa at res. 82=(Ile, Asn, Val, Leu, Tyr, Asp or Ala); Xaa at res. 83=(Leu, Tyr, Lys or Ile); Xaa at res. 84=(Lys, Arg, Asn, Tyr, Phe, Thr, Glu or Gly); Xaa at res. 85=(Lys, Arg, His, Gln, Asn, Glu or Val); Xaa at res. 86=(Tyr, His, Glu or Ile); Xaa at res. 87=(Arg, Glu, Gln, Pro or Lys); Xaa at res. 88=(Asn, Asp, Ala, Glu, Gly or Lys); Xaa at res. 89=(Met or Ala); Xaa at res. 90=(Val, Ile, Ala, Thr, Ser or Lys); Xaa at res. 91=(Val or Ala); Xaa at res. 92=(Arg, Lys, Gln, Asp, Glu, Val, Ala, Ser or Thr); Xaa at res. 93=(Ala, Ser, Glu, Gly, Arg or Thr); Xaa at res. 95=(Gly, Ala or Thr); Xaa at res. 97=(His, Arg, Gly, Leu or Ser). Further, after res. 53 in rBMP-3b and mGDF-10 there is an Ile; after res. 54 in GDF-1 there is a T; after res. 54 in BMP-3 there is a V; after res. 78 in BMP-8 and Dorsalin there is a G; after res. 37 in hGDF-1 there is Pro, Gly, Gly, Pro.

Generic Sequence 10 (SEQ ID NO:7) includes all of Generic Sequence 9 (SEQ ID NO:6) and in addition includes the following sequence (SEQ ID NO:9) at its N-terminus:

| SEQ ID NO: 9 |
|---|
| Cys Xaa Xaa Xaa Xaa |
| 1             5 |

Accordingly, beginning with residue 6, each "Xaa" in Generic Sequence 10 is a specified amino acid defined as for Generic Sequence 9, with the distinction that each residue number described for Generic Sequence 9 is shifted by five in Generic Sequence 10. Thus, "Xaa at res. 1=(Tyr, Phe, His, Arg, Thr, Lys, Gln, Val or Glu)" in Generic Sequence 9 refers to Xaa at res. 6 in Generic Sequence 10. In Generic Sequence 10, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

Based upon alignment of the naturally-occurring morphogens within the definition of Generic Sequence 10, it should be clear that gaps and/or insertions of one or more amino acid residues can be tolerated (without abrogating or substantially impairing biological activity) at least between or involving residues 11–12, 42–43, 59–60, 68–69 and 83–84.

As noted above, certain preferred morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the Drosophila 60A protein, as well as the closely related proteins BMP-5, BMP-6 and Vgr-1. Accordingly, in certain particularly preferred embodiments, useful morphogenic proteins include active proteins comprising pairs of polypeptide chains within the generic amino acid sequence herein referred to as "OPX" (SEQ ID NO:3), which defines the seven cysteine skeleton and accommodates the homologies between several identified variants of OP-1 and OP-2. Accordingly, each "Xaa" at a given position in OPX independently is selected from the residues occurring at the corresponding position in the C-terminal sequence of mouse or human OP-1 or OP-2. Specifically, each "Xaa" is independently selected from a group of one or more specified amino acids as defined below:

```
Cys Xaa Xaa His Glu Leu Tyr Val Ser Phe Xaa Asp Leu Gly Trp
1             5                   10                  15
Xaa Asp Trp Xaa Ile Ala Pro Xaa Gly Tyr Xaa Ala Tyr Tyr Cys
              20                  25                  30
Glu Gly Glu Cys Xaa Phe Pro Leu Xaa Ser Xaa Met Asn Ala Thr
                  35                  40                  45
Asn His Ala Ile Xaa Gln Xaa Leu Val His Xaa Xaa Xaa Pro Xaa
                  50                  55                  60
Xaa Val Pro Lys Xaa Cys Cys Ala Pro Thr Xaa Leu Xaa Ala Xaa
                  65                  70                  75
Ser Val Leu Tyr Xaa Asp Xaa Ser Xaa Asn Val Ile Leu Xaa Lys
                  80                  85                  90
Xaa Arg Asn Met Val Val Xaa Ala Cys Gly Cys His
                  95                  100
``` wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred embodiment, useful morphogenically-active proteins have polypeptide chains with amino acid sequences comprising a sequence encoded by a nucleic acid that hybridizes with DNA or RNA encoding reference morphogen sequences, e.g., C-terminal sequences defining the conserved seven cysteine skeletons of OP-1, OP-2, BMP-2, BMP-4, BMP-5, BMP-6, 60A, GDF-3, GDF-5, GDF-6, GDF-7 and the like. As used herein, high stringency hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in standard molecular biology cloning texts. See, for example, *MOLECULAR CLONING A LABORATORY MANUAL*, 2nd Ed., ed. by Sambrook, Fritsch and Maniatis (Cold Spring Harbor Laboratory Press: 1989); DNA CLONING, Volumes I and II (D. N. Glover ed., 1985); *OLIGONUCLEOTIDE SYNTHESIS* (M. J. Gait ed., 1984); *NUCLEIC ACID HYBRIDIZATION* (B. D. Hames & S. J. Higgins eds. 1984); and B. Perbal, *A PRACTICAL GUIDE To MOLECULAR CLONING* (1984).

In other embodiments, as an alternative to the administration of a morphogenic protein, an effective amount of an agent competent to stimulate or induce increased endogenous morphogen expression in a mammal may be administered by any of the routes described herein. Such a morphogen inducer may be provided to a mammal, e.g., by systemic administration to the mammal or by direct administration to the neural tissue. A method for identifying and testing inducers (stimulating agents) competent to modulate the levels of endogenous morphogens in a given tissue is described in published applications WO93/05172 and WO93/05751, each of which is incorporated by reference herein. Briefly, candidate compounds are identified and tested by incubation in vitro with test tissue or cells, or a cultured cell line derived therefrom, for a time sufficient to allow the compound to affect the production, i. e., cause the expression and/or secretion, of a morphogen produced by the cells of that tissue. Suitable tissue, or cultured cells of a suitable tissue, are preferably selected from renal epithelium, ovarian tissue, fibroblasts, and osteoblasts.

In yet other embodiments, an agent which acts as an agonist of a morphogen receptor may be administered instead of the morphogen itself. Such an agent may also be referred to an a morphogen "mimic," "mimetic," or "analog." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g., induction of differentiation of metanephric mesenchyme, induction of endochondral bone formation). For example, methods of identifying morphogen inducers or agonists of morphogen receptors may be found in U.S. Pat. No. 08/478,097 filed Jun. 7, 1995 and U.S. Pat. No. 08/507, 598 filed Jul. 26, 1995, disclosures of which are incorporated herein by reference.

As a general matter, methods of the present invention may be applied to the treatment of any mammalian subject at risk of or afflicted with a neural tissue insult or neuropathy. The invention is suitable for the treatment of any primate, preferably a higher primate such as a human. In addition, however, the invention may be employed in the treatment of domesticated mammals which are maintained as human companions (e.g., dogs, cats, horses), which have significant commercial value (e.g., goats, pigs, sheep, cattle, sporting or draft animals), which have significant scientific value (e.g., captive or free specimens of endangered species, or inbred or engineered animal strains), or which otherwise have value.

C. Formulations and Methods of Treatment

Morphogens, morphogen inducers, or agonists of morphogen receptors of the present invention may be administered by any route which is compatible with the particular morphogen, inducer, or agonist employed. Thus, as appropriate, administration may be oral or parenteral, including intravenous and intraperitoneal routes of administration. In addition, administration may be by periodic injections of a bolus of the morphogen, inducer or agonist, or may be made more continuous by intravenous or intraperitoneal administration from a reservoir which is external (e.g., an i.v. bag) or internal (e.g., a bioerodable implant, or a colony of implanted, morphogen-producing cells).

Therapeutic agents of the invention (i.e., morphogens, morphogen inducers or agonists of morphogen receptors) may be provided to an individual by any suitable means, directly (e.g., locally, as by injection, implantation or topical administration to a tissue locus) or systemically (e.g., parenterally or orally). Where the agent is to be provided parenterally, such as by intravenous, subcutaneous, intramolecular, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the agent preferably comprises part of an aqueous or physiologically compatible fluid suspension or solution. Thus, the morphogen carrier or vehicle is physiologically acceptable so that in addition to delivery of the desired agent to the patient, it does not otherwise adversely affect the patient's electrolyte and/or volume balance. The fluid medium for the agent thus can comprise normal physiologic saline (e.g., 9.85% aqueous NaCl, 0.15M, pH 7–7.4).

Association of the mature morphogen dimer with a morphogen pro domain results in the pro form of the morphogen which typically is more soluble in physiological solutions than the corresponding mature form. In fact, endogenous morphogens are thought to be transported (e.g., secreted and circulated) in the mammalian body in this form. This soluble form of the protein can be obtained from culture medium of morphogen-secreting mammalian cells, e.g., cells transfected with nucleic acid encoding and competent to express the morphogen. Alternatively, a soluble species can be formulated by complexing the mature, morphogenically-active polypeptide dimer (or an active fragment thereof) with a morphogen pro domain polypeptide or a solubility-enhancing fragment thereof. Solubility-enhancing pro domain fragments can be any N-terminal, C-terminal or internal fragment of the pro region of a member of the morphogen family that complexes with the mature polypeptide dimer to enhance stability and/or dissolubility of the resulting noncovalent or convalent complex. Typically, useful fragments are those cleaved at the proteolytic site Arg-Xaa-Xaa-Arg. A detailed description of soluble complex forms of morphogenic proteins, including how to make, test and use them, is described in WO 94/03600 (PCT US 93/07189). In the case of OP-1, useful pro domain polypeptide fragments include the intact pro domain polypeptide (residues 30–292) and fragments 48–292 and 158–292, all of SEQ ID NO:2. Another molecule capable of enhancing solubility and particularly useful for oral administrations, is casein. For example, addition of 0.2% casein increases solubility of the mature active form of OP1 by 80%. Other components found in milk and/or various serum proteins may also be useful.

Useful solutions for parenteral administration may be prepared by any of the methods well known in the pharmaceutical art, described, for example, in *REMINGTON'S PHARMACEUTICAL SCIENCES* (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration may also be prepared by mixing the morphogen, inducer or agonist with a non-irritating excipient such as cocoa butter or other compositions which are solid at room temperature and liquid at body temperatures.

Formulations for topical administration to the skin surface may be prepared by dispersing the morphogen, inducer or agonist with a dermatologically acceptable carrier such as a lotion, cream, ointment or soap. Particularly useful are carriers capable of forming a film or layer over the skin to localize application and inhibit removal. For topical administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

Alternatively, the agents described herein may be administered orally. Oral administration of proteins as therapeutics generally is not practiced, as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590). In addition, at least one morphogen, OP-1, has been identified in mammary gland extract, colostrum and 57-day milk. Moreover, the OP-1 purified from mammary gland extract is morphogenically-active and is also detected in the bloodstream. Maternal administration, via ingested milk, may be a natural delivery route of TGF-β superfamily proteins. Letterio, et al., *Science* 264: 1936–1938 (1994), report that TGF-β is present in murine milk, and that radiolabelled TGF-β is absorbed by gastrointestinal mucosa of suckling juveniles. Labeled, ingested TGF-β appears rapidly in intact form in the juveniles' body tissues, including lung, heart and liver. Finally, soluble form morphogen, e.g., mature morphogen associated with the pro domain, is morphogenically-active. These findings, as well as those disclosed in the examples below, indicate that oral and parenteral administration are viable means for administering TGF-β superfamily proteins, including the morphogens, to an individual. In addition, while the mature forms of certain morphogens described herein typically are sparingly soluble, the morphogen form found in milk (and mammary gland extract and colostrum) is readily soluble, probably by association of the mature, morphogenically-active form with part or all of the pro domain of the expressed, full length polypeptide sequence and/or by association with one or more milk components. Accordingly, the compounds provided herein may also be associated with molecules capable of enhancing their solubility in vitro or in vivo.

Where the morphogen is intended for use as a therapeutic for disorders of the CNS, an additional problem must be addressed: overcoming the blood-brain barrier, the brain capillary wall structure that effectively screens out all but selected categories of substances present in the blood, preventing their passage into the brain. The blood-brain barrier can be bypassed effectively by direct infusion of the morphogen or morphogen-stimulating agent into the brain, or by intranasal administration or inhalation of formulations suitable for uptake and retrograde transport by olfactory neurons. Alternatively, the morphogen or morphogen-stimulating agent can be modified to enhance its transport across the blood-brain barrier. For example, truncated forms of the morphogen or a morphogen-stimulating agent may be most successful. Alternatively, the morphogens, inducers or agonists provided herein can be derivatized or conjugated to a lipophilic moiety or to a substance that is actively transported across the blood-brain barrier, using standard means known to those skilled in the art. See, for example, Pardridge, *Endocrine Reviews* 7: 314–330 (1986) and U.S. Pat. No. 4,801,575.

The compounds provided herein may also be associated with molecules capable of targeting the morphogen, inducer or agonist to the desired tissue. For example, an antibody, antibody fragment, or other binding protein that interacts specifically with a surface molecule on cells of the desired tissue, may be used. Useful targeting molecules may be designed, for example, using the single chain binding site technology disclosed in U.S. Pat. No. 5,091,513. Targeting molecules can be covalently or non-covalently associated with the morphogen, inducer or agonist.

As will be appreciated by one of ordinary skill in the art, the formulated compositions contain therapeutically-effective amounts of the morphogen, morphogen inducers or agonists of morphogen receptors. That is, they contain an amount which provides appropriate concentrations of the agent to the affected nervous system tissue for a time sufficient to stimulate a detectable restoration of impaired central or peripheral nervous system function, up to and including a complete restoration thereof. As will be appreciated by those skilled in the art, these concentrations will vary depending upon a number of factors, including the biological efficacy of the selected agent, the chemical characteristics (e.g., hydrophobicity) of the specific agent, the formulation thereof, including a mixture with one or more excipients, the administration route, and the treatment envisioned, including whether the active ingredient will be administered directly into a tissue site, or whether it will be administered systemically. The preferred dosage to be administered is also likely to depend on variables such as the condition of the diseased or damaged tissues, and the overall health status of the particular mammal. As a general matter, single, daily, biweekly or weekly dosages of 0.00001–1000 mg of a morphogen are sufficient, with 0.0001–100 mg being preferable, and 0.001 to 10 mg being even more preferable. Alternatively, a single, daily, biweekly or weekly dosage of 0.01–1000 µg/kg body weight, more preferably 0.01–10 mg/kg body weight, may be advantageously employed. The present effective dose can be administered in a single dose or in a plurality (two or more) of installment doses, as desired or considered appropriate under the specific circumstances. A bolus injection or diffusable infusion formulation can be used. If desired to facilitate repeated or frequent infusions, implantation of a semi-permanent stent (e.g., intravenous, intraperitoneal, intracisternal or intracapsular) may be advisable.

The morphogens, inducers or agonists of the invention may, of course, be administered alone or in combination with other molecules known to be beneficial in the treatment of the conditions described herein. For example, various well-known growth factors, hormones, enzymes, therapeutic compositions, antibiotics, or other bioactive agents can also be administered with the morphogen. Thus, various known growth factors such as NGF, EGF, PDGF, IGF, FGF, TGF-α, and TGF-β, as well as enzymes, enzyme inhibitors, antioxidants, anti-inflammatory agents, free radical scavenging agents, antibiotics and/or chemoattractant/chemotactic factors, can be included in the present morphogen formulation.

EXAMPLE 1

Preparation of Soluble Morphogen Protein Solutions for In vivo Administration

A. Aqueous Solutions

While the mature dimeric morphogenic proteins defined herein are typically sparingly soluble in physiological buffers, they can be solubilized to form injectable suspensions or solutions. One exemplary aqueous formulation containing a morphogen is made, for example, by dispersing the morphogen in 50% ethanol containing acetonitrile in 0.1% trifluoroacetic acid (TFA) or 0.1% HCl, or in an equivalent solvent. One volume of the resultant solution then is added, for example, to ten volumes of phosphate buffered saline (PBS), which further may include 0.1–0.2% human serum albumin (HSA) or a similar carrier protein. The resultant solution is preferably vortexed extensively to produce a physiologically acceptable morphogen formulation.

In another embodiment, the morphogen, including OP-1, is solubilized by reducing the pH of the solution. In one preferred formulation, the protein is solubilized in 0.2 mM acetate buffer, pH 4.5, containing 5% mannitol, to render the solution more isotonic. Other standard means for creating physiologically acceptable formulations are within the skill of the art.

B. Soluble Complex Formulations

Another preferred form is a dimeric morphogenic protein comprising at least the C-terminal seven cysteine skeleton characteristic of the morphogen family, complexed with a peptide comprising a pro region of a member of the morphogen family, or a solubility-enhancing fragment thereof, or an allelic, phylogenetic or other sequence variant thereof. The solubility-enhancing fragment is any N-terminal or C-terminal fragment of the pro domain polypeptide of a member of the morphogen family that complexes with the mature polypeptide dimer to enhance the stability of the resulting soluble complex. Preferably, the dimeric morphogenic protein is complexed with two such pro domain peptides.

As described above and in published application WO 94/03600, incorporated by reference herein, the soluble complex form is isolated from the cell culture media (or a body fluid) under appropriate conditions. Alternatively, the complex is formulated in vitro.

Soluble morphogen complexes are isolated from conditioned media using a simple, three step chromatographic protocol performed in the absence of denaturants. The protocol involves running the media (or body fluid) over an affinity column, followed by ion exchange and gel filtration chromatographies generally as described in WO 94/03600. The affinity column described below is a Zn-IMAC column. The present example uses human OP-1, and is not intended to be limiting. The present protocol has general applicability to the purification of a variety of morphogens, all of which are anticipated to be isolatable using only minor modifications of the protocol described below. An alternative protocol also envisioned to have utility includes an immunoaffinity column, created using standard procedures and, for example, using antibody specific for a given morphogen pro domain (complexed, for example, to a protein A-conjugated Sepharose column). Protocols for developing immunoaffinity columns are well described in the art (see, for example, *GUIDE TO PROTEIN PURIFICATION*, M. Deutscher, ed., Academic Press, San Diego, 1990, particularly sections VII and XI thereof).

In this example, OP-1 was expressed in mammalian (CHO, Chinese hamster ovary) cells as described in the art (see, for example, international application US90/05903 (WO 91/05802). The CHO cell conditioned media containing 0.5% FBS is initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC purified soluble OP-1 is next applied to an S-Sepharose action-exchange column equilibrated in 20 mM $NaPO_4$ (pH 7.0) with 50 mM NaCl. The protein then is applied to a Sephacryl S-200HR column equilibrated in TBS. Using substantially the same protocol, soluble morphogens can also be isolated from one or more body fluids, including milk, serum, cerebrospinal fluid or peritoneal fluid.

The soluble OP-1 complex elutes with an apparent molecular weight of 110 kDa. This agrees well with the predicted composition of the soluble OP1 complex, with one mature OP1 dimer (35–36 kDa) associated with two pro domains (39 kDa each). Purity of the final complex can be verified by running the appropriate fraction in a reduced 15% polyacrylamide gel.

As an alternative to purifying soluble complexes from culture media or a body fluid, soluble complexes can be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain polypeptide has an opportunity to associate with the mature dimeric protein under relaxed folding conditions. The concentration of denaturant in the solution then is decreased in a controlled, preferably step-wise manner, so as to allow proper refolding of the dimer and pro domain peptides, while maintaining the association of the pro domain peptides with the mature dimer. Useful denaturants include 4–6 M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea or GuHCl, which then preferably can be diluted into a physiological buffer. Protein purification/renaturing procedures and considerations are well described in the art, and details for developing a suitable renaturing protocol readily can be determined by one having ordinary skill in the art. One useful text on the subject is GUIDE TO PROTEIN PURIFICATION, M. Deutscher, ed., Academic Press, San Diego, 1990, particularly section V. Complex formation may also be aided by addition of one or more chaperone proteins.

The stability of the highly purified soluble morphogen complex in a physiological buffer, e.g., Tris-buffered saline (TBS) and phosphate-buffered saline (PBS), can be enhanced by any of a number of means, including any one or more of three classes of additives. These additives include basic amino acids (e.g., L-arginine, lysine and betaine); nonionic detergents (e.g., Tween 80 or NonIdet P-120); and carrier proteins (e.g., serum albumin and casein). Useful concentrations of these additives include 1–100 mM, preferably 10–70 mM, including 50 mM, basic amino acid; 0.01–1.0%, preferably 0.05–0.2%, including 0.1% (v/v) nonionic detergent; and 0.01–1.0%, preferably 0.05–0.2%, including 0.1% (w/v) carrier protein.

EXAMPLE 2

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence. See Lyons, et al., PNAS 86: 4554–4558 (1989) for a description of the cDNA sequence. Similarly, particularly useful mOP-1-specific probe sequences are the BstX1-BglI fragment, a 0.68 Kb sequence that covers approximately two-thirds of the mOP-1 pro region; a StuI—StuI fragment, a 0.2 Kb sequence immediately upstream of the 7-cysteine domain; and the EarI-PstI fragment, an 0.3 Kb fragment containing a portion of the 3' untranslated sequence (See SEQ ID NO:18, where the pro region is defined essentially by residues 30–291.) Similar approaches may be used, for example, with hOP1 (SEQ ID NO:16) or human or mouse OP-2 (SEQ ID NOS:20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski, et al., Anal. Biochem 162: 156–159 (1987) and described below. Poly (A)+RNA is prepared by using oligo (dT)-cellulose chromatography (e.g., Type 7, from Pharmacia LKB Biotechnology, Inc.). Poly (A)+RNA (generally 15 mg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 752,764, and in Ozkaynak, et al., Biochem. Biophys. Res. Comm. 179: 116–123 (1991), and Ozkaynak, et al., (JBC, in press) (1992), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

EXAMPLE 3

Morphogen Localization in the Nervous System

Morphogens have been identified in developing and adult rat brain and spinal cord tissue, as determined both by northern blot hybridization of morphogen-specific probes to mRNA extracts from developing and adult nerve tissue (see Example 2, above) and by immunolocalization studies. For example, northern blot analysis of developing rat tissue has identified significant OP-1 mRNA transcript expression in the CNS (U.S. Ser. No. 752,764, and Ozkaynak, et al., Biochem. Biophys. Res. Comm., 179: 11623 (1991) and Ozkaynak, et al., JBC, in press (1992)). GDF-1 mRNA appears to be expressed primarily in developing and adult nerve tissue, specifically in the brain, including the cerebellum and brain stem, spinal cord and peripheral nerves. Lee, S., *PNAS* 88: 4250–4254 (1991). BMP2B (also referred in the art as BMP4) and Vgr-1 transcripts also have been reported to be expressed in nerve tissue (Jones, et al., *Development* 111: 531–542 (1991)), although the nerve tissue does not appear to be the primary expression tissue for these genes. Ozkaynak, et al., *JBC* in press (1992). Specifically, CBMP2 transcripts are reported in the region of the diencephalon associated with pituitary development, and Vgr-1 transcripts are reported in the anteroposterior axis of the CNS, including in the roof plate of the developing neural tube, as well as in the cells immediately adjacent the floor plate of the developing neural tube. In older rats, Vgr-1 transcripts are reported in developing hippocampus tissue. In addition, the genes encoding OP-1 and BMP2 originally were identified by probing human hippocampus cDNA libraries.

Immunolocalization studies, performed using standard methodologies known in the art and disclosed in U.S. Ser. No. 752,764, filed Aug. 30, 1991, now abandoned the disclosure of which is incorporated herein, localized OP-1 expression to particular areas of developing and adult rat brain and spinal cord tissue. Specifically, OP1 protein expression was assessed in adult (2–3 months old) and five or six-day old mouse embryonic nerve tissue, using standard morphogen-specific antisera, specifically, rabbit anti-OP1 antisera, made using standard antibody protocols known in the art and preferably purified on an OP1 affinity column. The antibody itself was labelled using standard fluorescent labelling techniques, or a labelled anti-rabbit IgG molecule was used to visualize bound OP-1 antibody.

As can be seen in FIG. 2, immunofluorescence staining demonstrates the presence of OP-1 in adult rat central nervous system (CNS.) Similar and extensive staining is seen in both the brain (Panel 1A) and spinal cord (Panel 1B). OP-1 appears to be localized predominantly to the extracellular matrix of the grey matter (neuronal cell bodies), distinctly present in all areas except the cell bodies themselves. In white matter, formed mainly of myelinated nerve fibers, staining appears to be confined to astrocytes (glial cells). A similar staining pattern also was seen in newborn rat (10 day old) brain sections.

In addition, OP-1 has been specifically localized in the substantia nigra, which is composed primarily of striatal basal ganglia, a system of accessory motor neurons that function is association with the cerebral cortex and corticospinal system. Dysfunctions in this subpopulation or system of neurons are associated with a number of neuropathies, including Huntington's chorea and Parkinson's disease.

OP-1 also has been localized at adendema glial cells, known to secrete factors into the cerebrospinal fluid, and which occur around the intraventricular valve, coroid fissure, and central canal of the brain in both developing and adult rat.

Finally, morphogen inhibition in developing embryos inhibits nerve tissue development. Specifically, 9-day mouse embryo cells, cultured in vitro under standard culturing conditions, were incubated in the presence and absence of an OP-1-specific monoclonal antibody prepared using recombinantly produced, purified mature OP1 and the immunogen. The antibody was prepared using standard antibody production means well known in the art and as described generally in Example 14. After two days, the effect of the antibody on the developing embryo was evaluated by histology. As determined by histological examination, the OP-1-specific antibody specifically inhibits eye lobe formation in the developing embryo. In particular, the diencephalon outgrowth does not develop. In addition, the heart is malformed and enlarged. Moreover, in separate immunolocalization studies on embryo sections with labelled OP-1 specific antibody, the OP-1-specific antibody localizes to neural epithelia.

The endogenous morphogens which act on neuronal cells may be expressed and secreted by nerve tissue cells, e.g., by neurons and/or glial cells associated with the neurons, and/or they may be transported to the neurons by the cerebrospinal fluid and/or bloodstream. Recently, OP-1 has been identified in the human blood (See Example 10, below). In addition, transplanted Schwann cells recently have been shown to stimulate nerve fiber formation in rat spinal cord, including inducing vascularization and myelin sheath formation around at least some of the new neuronal processes. Bunge, *Exp. Neurology* 114: 254–257 (1991). The regenerative property of these cells may be mediated by the secretion of a morphogen by the Schwann cells.

EXAMPLE 4

Morphogen Enhancement of Neuronal Cell Survival

The morphogens described herein enhance cell survival, particularly of neuronal cells at risk of dying. For example, fully differentiated neurons are non-mitotic and die in vitro when cultured under standard mammalian cell culture conditions, using a chemically defined or low serum medium known in the art. See, for example, Charness, *J. Biol. Chem.* 26: 3164–3169 (1986) and Freese, et al., *Brain Res.* 521: 254–264 (1990). However, if a primary culture of non-mitotic neuronal cells is treated with a morphogen, the survival of these cells is enhanced significantly. For example, a primary culture of striatal basal ganglia isolated from the substantia nigra of adult rat brain was prepared using standard procedures, e.g., by dissociation by trituration with pasteur pipette of substantia nigra tissue, using standard tissue culturing protocols, and grown in a low serum medium, e.g., containing 50% DMEM (Dulbecco's modified Eagle's medium), 50% F-12 medium, heat inactivated horse serum supplemented with penicillin/streptomycin and 4 g/l glucose. Under standard culture conditions, these cells are undergoing significant cell death by three weeks when cultured in a serum-free medium. Cell death is evidenced morphologically by the inability of cells to remain adherent and by changes in their ultrastructural characteristics, e.g., by chromatin clumping and organelle disintegration.

In this example, the cultured basal ganglia were treated with chemically defined medium conditioned with 0.1–100 ng/ml OP-1. Fresh, morphogen-conditioned medium was provided to the cells every 3–4 days. Cell survival was enhanced significantly and was dose dependent upon the level of OP1 added: cell death decreased significantly as the concentration of OP1 was increased in cell cultures. Specifically, cells remained adherent and continued to maintain the morphology of viable differentiated neurons. In the absence of morphogen treatment, the majority of the cultured cells dissociated and underwent cell necrosis.

Dysfunctions in the basal ganglia of the substantia nigra are associated with Huntington's chorea and parkinsonism in vivo. The ability of the morphogens defined herein to enhance neuron survival indicates that these morphogens will be useful as part of a therapy to enhance survival of neuronal cells at risk of dying in vivo due, for example, to a neuropathy or chemical or mechanical trauma. It is particularly anticipated that these morphogens will provide a useful therapeutic agent to treat neuropathies which affect the striatal basal ganglia, including Huntington's chorea and Parkinson's disease. For clinical applications, the morphogen may be administered or, alternatively, a morphogen-stimulating agent may be administered.

EXAMPLE 5

Morphogen-Induced Redifferentiation of Transformed Cells

The morphogens described herein also induce redifferentiation of transformed cells to a morphology characteristic of untransformed cells. In particular, the morphogens are capable of inducing redifferentiation of transformed cells of neuronal origin to a morphology characteristic of untransformed neurons. The example provided below details morphogen induced redifferentiation of a transformed cell line of neuronal origin, NG105-115. Morphogen-induced redifferentiation of transformed cells also has been shown in mouse neuroblastoma cells (N1E-115) and in human embryo carcinoma cells (see copending U.S. Ser. No. 752, 764, incorporated herein by reference.)

NG108-15 is a transformed hybrid cell line produced by fusing neuroblastoma × glioma cells (obtained from America Type Tissue Culture, Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells (see FIG. 2A). Incubation of NG108-15 cells, cultured in a chemically defined, serum-free medium, with 0.1 to 300 ng/ml of OP-1 for four hours induces an orderly, dose-dependent change in cell morphology.

Figure 2B:
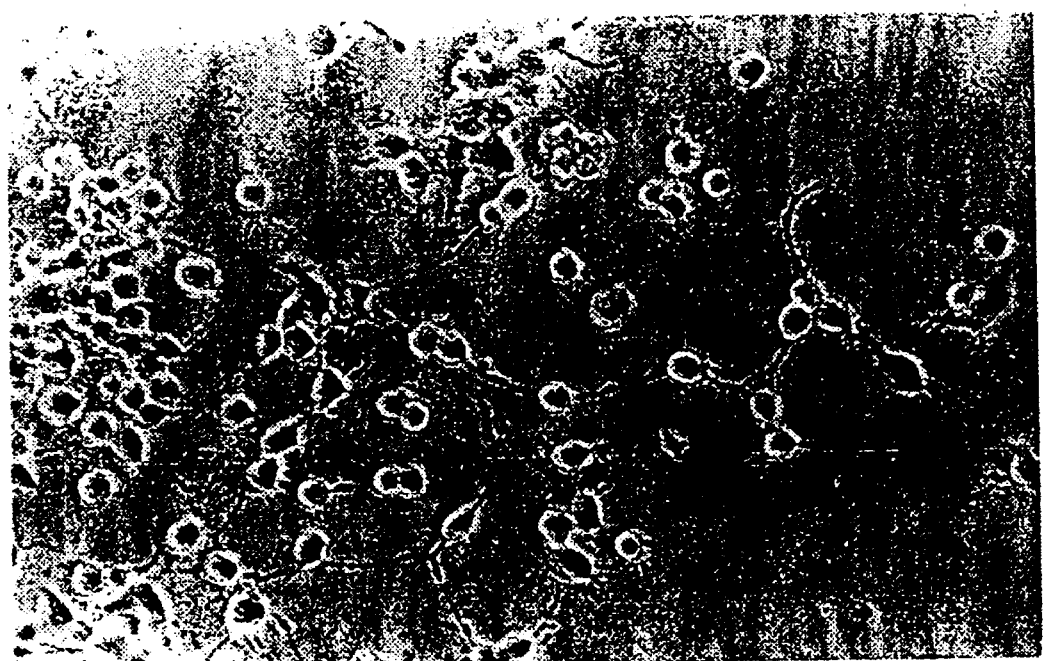
Figure 4:
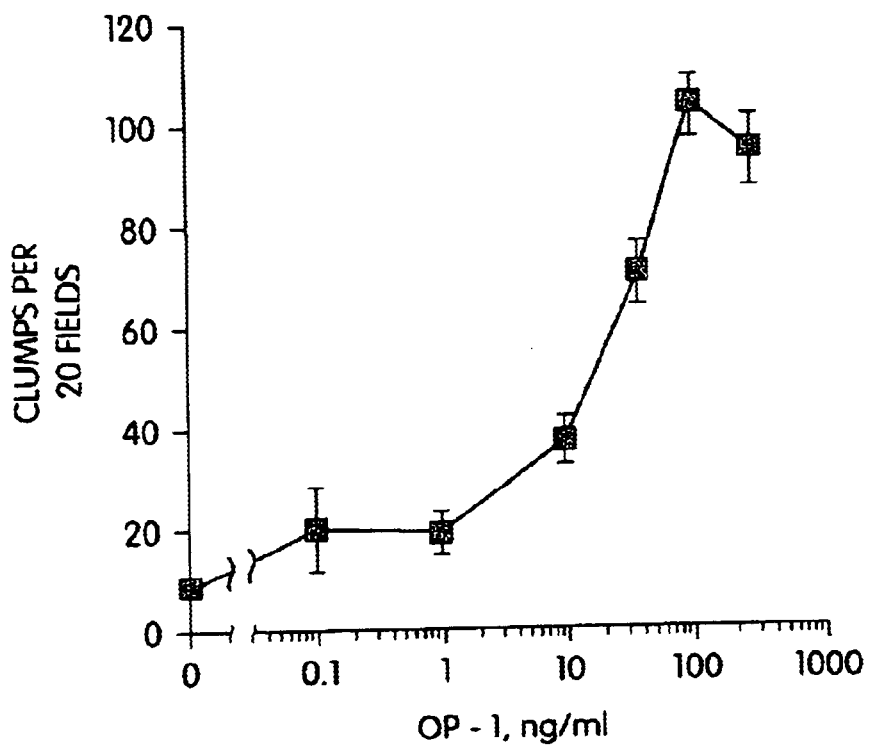
FIG. 4 is a line graph depicting the mean number of cell aggregates counted in twenty (20) randomly selected magnified viewing fields as a function of morphogen concentration.

In the experiment NG108-15 cells were subcultured on poly-L-lysine coated 6-well plates. Each well contained 40–50,000 cells in 2.5 ml of chemically defined medium. On the third day 2.5 ml of OP-1 in 60% ethanol containing 0.025% trifluoroacetic was added to each well. OP-1 concentrations of 0–300 ng/ml were tested. Typically, the media was changed daily with new aliquots of OP-1, although morphogenesis can be induced by a single four hour incubation with OP-1. In addition, OP-1 concentrations of 10 ng/ml were sufficient to induce redifferentiation. After one day, hOP-1-treated cells undergo a significant change in their cellular ultrastructure, including rounding of the soma, increase in phase brightness and extension of the short neurite processes. After two days, cells treated with OP-1 begin to form epithelioid sheets, which provide the basis for the growth of mutilayered aggregates at three day's post-treatment. By four days, the great majority of OP-1-treated cells are associated in tightly-packed, mutilayered aggregates (FIG. 2B). FIG. 4 plots the mean number of multilayered aggregates or cell clumps identified in twenty randomly selected fields from six independent experiments, as a function of morphogen concentration. Forty ng/ml of OP-1 is sufficient for half maximum induction of cell aggregation.

The morphogen-induced redifferentiation occurred without any associated changes in DNA synthesis, cell division, or cell viability, making it unlikely that the morphologic changes were secondary to cell differentiation or a toxic effect of hOP-1. Moreover, the OP1-induced morphogenesis does not inhibit cell division, as determined by $^3$H-thymidine uptake, unlike other molecules which have been shown to stimulate differentiation of transformed cells, such as butyrate, DMSO, retinoic acid or Forskolin. The data indicate that OP-1 can maintain cell stability and viability after inducing redifferentiation. In addition, the effects are morphogen specific, and redifferentiation is not induced when NG108-15 cells are incubated with 0.1–40 ng/ml TGF-$\beta$.

The experiments also have been performed with highly purified soluble morphogen (e.g., mature OP-1 associated with its pro domain) which also specifically induced redifferentiation of NG108-15 cells.

The morphogens described herein accordingly provide useful therapeutic agents for the treatment of neoplasias and neoplastic lesions of the nervous system, particularly in the treatment of neuroblastomas, including retinoblastomas, and gliomas. The morphogens themselves may be administered or, alternatively, a morphogen-stimulating agent may be administered.

EXAMPLE 6

Nerve Tissue Protection from Chemical Trauma

The ability of the morphogens described herein to enhance survival of neuronal cells and to induce cell aggregation and cell—cell adhesion in redifferentiated cells, indicates that the morphogens will be useful as therapeutic agents to maintain neural pathways by protecting the cells defining the pathway from the damage caused by chemical trauma. In particular, the morphogens can protect neurons, including developing neurons, from the effects of toxins known to inhibit the proliferation and migration of neurons and to interfere with cell—cell adhesion. Examples of such toxins include ethanol, one or more of the toxins present in cigarette smoke, and a variety of opiates. The toxic effects of ethanol on developing neurons induces the neurological damage manifested in fetal alcohol syndrome. The morphogens also may protect neurons from the cytotoxic effects associated with excitatory amino acids such as glutamate.

For example, ethanol inhibits the cell—cell adhesion effects induced in morphogen-treated NG108-15 cells when provided to these cells at a concentration of 25–50 mM. Half maximal inhibition can be achieved with 5–10 mM ethanol, the concentration of blood alcohol in an adult following ingestion of a single alcoholic beverage. Ethanol likely interferes with the homophilic binding of CAMs between cells, rather than their induction, as morphogen-induced N-CAM levels are unaffected by ethanol. Moreover, the inhibitory effect is inversely proportional to morphogen concentration. Accordingly, it is envisioned that administration of a morphogen or morphogen-stimulating agent to neurons, particularly developing neurons, at risk of damage from exposure to toxins such as ethanol, may protect these cells from nerve tissue damage by overcoming the toxin's inhibitory effects. The morphogens described herein also are useful in therapies to treat damaged neural pathways resulting from a neuropathy induced by exposure to these toxins.

EXAMPLE 7

Morphogen-Induced CAM Expression

The morphogens described herein induce CAM expression, particularly N-CAM expression, as part of their induction of morphogenesis. CAMs are morphoregulatory molecules identified in all tissues as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

N-CAMs are implicated in appropriate neural development, including appropriate neurulation, neuronal migration, fasciculation, and synaptogenesis. Inhibition of N-CAM production, as by complexing the molecule with an N-CAM-specific antibody, inhibits retina organization, including retinal axon migration, and axon regeneration in the peripheral nervous system, as well as axon synapses with target muscle cells. In addition, significant evidence indicates that physical or chemical trauma to neurons, oncogenic transformation and some genetic neurological disorders are accompanied by changes in CAM expression, which alter the adhesive or migratory behavior of these cells. Specifically, increased N-CAM levels are reported in Huntington's disease striatum (e.g., striatal basal ganglia), and decreased adhesion is noted in Alzheimer's disease.

The morphogens described herein stimulate CAM production, particularly L1 and N-CAM production, including all three isoforms of the N-CAM molecule. For example, N-CAM expression is stimulated significantly in morphogen-treated NG108-15 cells. Untreated NG108-15 cells exhibit a fibroblastic, or minimally differentiated morphology and express only the 180 and 140 isoforms of N-CAM normally associated with a developing cell. Following morphogen treatment, these cells exhibit a morphology characteristic of adult neurons and express enhanced levels of all three N-CAM isoforms. Using a similar protocol as described in the example below, morphogen treatment of NG108-15 cells also induced L1 expression.

Figure 3A:
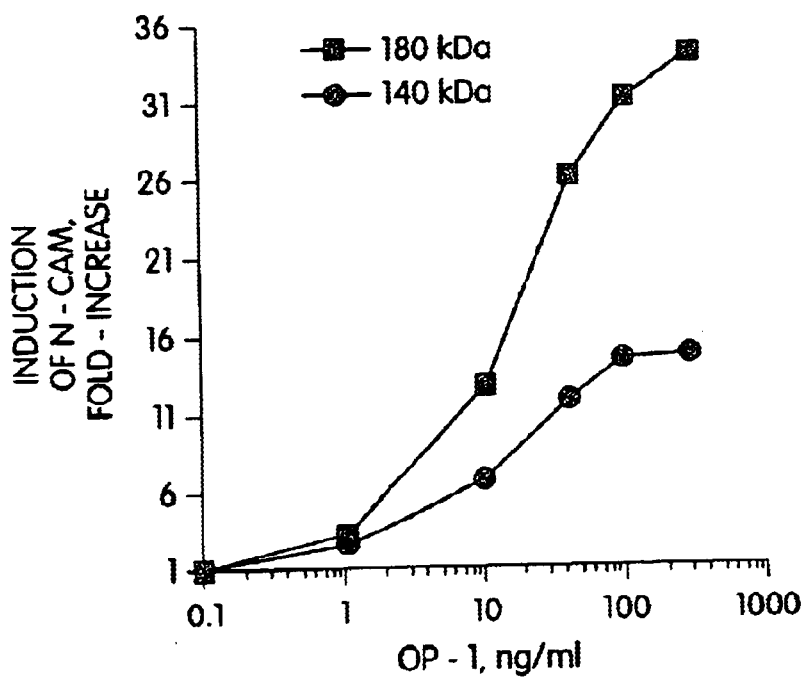
FIG. 3A is a line graph depicting a dose response curve for the induction of the 180 kDa and 140 kDa N-CAM isoforms in morphogen-treated NG108-15 cells.
Figure 3B:
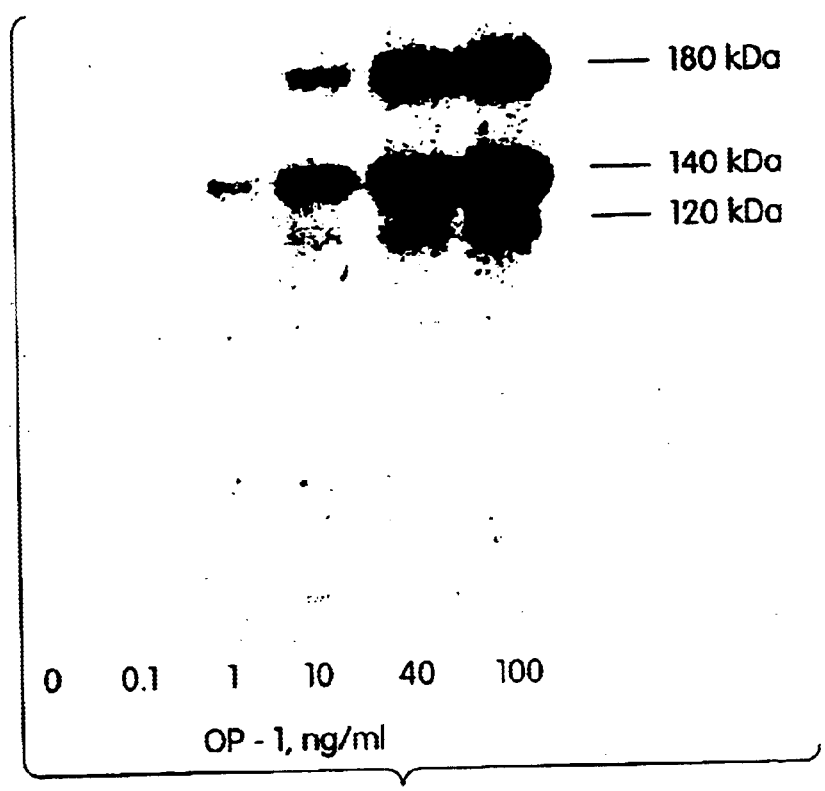
FIG. 3B is a photograph of a Western blot of whole cell extracts from morphogen-treated NG108-15 cells with an N-CAM-specific antibody.

In this example, NG108-15 cells were cultured for four days in the presence of increasing concentrations of OP-1 and standard Western blots performed on whole cell extracts. N-CAM isoforms were detected with an antibody which cross-reacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by western blot analyses using up to 100 mg of protein. Treatment of NG108-15 cells with OP-1 resulted in a dose-dependent increase in the expression of the 180 kDa and 140 kDa isoforms, as well as the induction of the 120 kDa isoform. See FIG. 3. FIG. 3B is a Western blot of OP1-treated NG108-15 cell extracts, probed with mAb H28.123, showing the induction of all three isoforms. FIG. 3A is a dose response curve of N-CAM-180 and N-CAM-140 induction as a function of morphogen concentration. N-CAM-120 is not shown in the graph, as it could not be quantitated in control cells. However, as is clearly evident from the Western blot in FIG. 3B, N-CAM-120 is induced in response to morphogen treatment.

The increase in N-CAM expression corresponded in a dose-dependent manner with the morphogen induction of multicellular aggregates. Compare FIG. 3A and FIG. 4. FIG. 4 graphs the mean number of multilayered aggregates (clumps) counted per 20 randomly selected, microscopic viewing fields in six independent experiments, versus the concentration of morphogen. The induction of the 120 isoform also indicates that morphogen-induced redifferentiation of transformed cells stimulates not only redifferentiation of these cells from a transformed phenotype, but also differentiation to a phenotype corresponding to a developed cell. Standard immunolocalization studies performed with the mAb H28.123 on morphogen-treated cells show N-CAM cluster formation associated with the periphery and processes of treated cells, and no reactivity with untreated cells. Moreover, morphogen treatment does not appear to inhibit cell division as determined by cell counting or $^3$H-thymidine uptake. Finally, known chemical differentiating agents, such as Forskolin and dimethylsulfoxide, do not induce N-CAM production.

In addition, the cell aggregation effects of OP1 on NG108-15 cells can be inhibited with anti-N-CAM antibodies or antisense N-CAM oligonucleotides. Antisense oligonucleotides can be made synthetically on a nucleotide synthesizer, using standard means known in the art. Preferably, phosphorothioate oligonucleotides ("S-oligos") are prepared, to enhance transport of the nucleotides across cell membranes. Concentrations of both N-CAM antibodies and N-CAM antisense oligonucleotides sufficient to inhibit N-CAM induction also inhibited formation of multilayered cell aggregates. Specifically, incubation of morphogen-treated NG108-15 cells with 0.3–3 mM N-CAM antisense S-oligos, 5–500 mM unmodified N-CAM antisense oligos, or 10 mg/ml mAb H28.123 significantly inhibits cell aggregation. It is likely that morphogen treatment also stimulates other CAMs, as inhibition is not complete.

Finally, the above-described experiments have also been performed with soluble morphogen (e.g., mature OP1 dimer, associated with its pro domain polypeptides as described in Example 1). The soluble form of morphogen also specifically induced CAM expression.

In addition to a transformed cell line, N-CAM expression can be assayed in a primary cell culture of neural or glial cells, following the procedures described herein. The efficacy of the morphogens described herein to affect N-CAM expression can be assessed in vitro using a suitable cell line, such as NG108-15 and the methods described herein.

As described above, preferred morphogens, inducers, or agonists of the present invention can induce both N-CAM expression in vitro and endochondral bone formation when implanted in vivo in a mammal in conjunction with a matrix permissive of bone morphogenesis. Thus, the methods described herein can be used to assess novel candidate morphogens, inducers, or agonists.

The experiments also have been performed with soluble morphogen (e.g., mature OP-1 associated with its pro domain) which also specifically induced CAM expression.

The morphogens described herein are useful as therapeutic agents to treat neurological disorders associated with altered CAM levels, particularly N-CAM levels, such as Huntington's chorea and Alzheimer's disease, and the like. In clinical applications, the morphogens themselves may be administered or, alternatively, a morphogen-stimulating agent may be administered.

The efficacy of the morphogens described herein to affect N-CAM expression may be assessed in vitro using a suitable cell line and the methods described herein. In addition to a transformed cell line, N-CAM expression can be assayed in a primary cell culture of neural or glial cells, following the procedures described herein. The efficacy of morphogen treatment on N-CAM expression in vivo may be evaluated by tissue biopsy as described in Example 10, below, and detecting N-CAM molecules with an N-CAM-specific antibody, such as mAb H28.123, or using the animal model described in Example 12.

Alternatively, the level of N-CAM proteins or protein fragments present in cerebrospinal fluid or serum also may be detected to evaluate the effect of morphogen treatment. N-CAM molecules are known to slough off cell surfaces and have been detected in both serum and cerebrospinal fluid. In addition, altered levels of the soluble form of N-CAM are associated with normal pressure hydrocephalus and type II schizophrenia. N-CAM fluid levels may be detected following the procedure described in Example 10 and using an N-CAM specific antibody, such as mAb H28.123.

EXAMPLE 8

Morphogen-Induced Nerve Gap Repair (PNS)

The morphogens described herein also stimulate peripheral nervous system axonal growth over extended distances allowing repair and regeneration of damaged neural pathways. While neurons of the peripheral nervous system can sprout new processes following injury, without guidance these sproutings typically fail to connect appropriately and die. Where the break is extensive, e.g., greater than 5 or 10 mm, regeneration is poor or nonexistent.

In this example morphogen stimulation of nerve regeneration was assessed using the rat sciatic nerve model. The rat sciatic nerve can regenerate spontaneously across a 5 mm gap, and occasionally across a 10 mm gap, provided that the severed ends are inserted in a saline-filled nerve guidance channel. In this experiment, nerve regeneration across a 12 mm gap was tested.

Adult female Sprague-Dawley rats (Charles River Laboratories, Inc.) weighing 230–250 g were anesthetized with intraperitoneal injections of sodium pentobarbital 35 mg/kg body weight). A skin incision was made parallel and just posterior to the femur. The avascular intermuscular plane between vastus lateralis and hamstring muscles were entered and followed to the loose fibroareolar tissue surrounding the sciatic nerve. The loose tissue was divided longitudinally thereby freeing the sciatic nerve over its full extent without devascularizing any portion. Under a surgical microscope the sciatic nerves were transected with microscissors at mid-thigh and grafted with an OP-1 gel graft that separated the nerve stumps by 12 mm. The graft region was encased in a silicone tube 20 mm in length with a 1.5 mm inner diameter, the interior of which was filled a morphogen solution. Specifically, The central 12 mm of the tube consisted of an OP-1 gel prepared by mixing 1 to 5 mg of substantially pure CHO-produced recombinant OP-1 with approximately 100 ml of MATRIGEL™ (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The OP-1-filled tube was implanted directly into the defect site, allowing 4 mm on each end to insert the nerve stumps. Each stump was abutted against the OP-1 gel and was secured in the silicone tube by three stitches of commercially available surgical 10-0 nylon through the epineurium, the fascicle sheath.

In addition to OP-1 gel grafts, empty silicone tubes, silicone tubes filled with gel only and "reverse" autografts, wherein 12 mm transected segments of the animal's sciatic nerve were rotated 180° prior to suturing, were grafted as controls. All experiments were performed in quadruplicate. All wounds were closed by wound clips that were removed after 10 days. All rats were grafted on both legs. At 3 weeks the animals were sacrificed, and the grafted segments removed and frozen on dry ice immediately. Frozen sections then were cut throughout the graft site, and examined for axonal regeneration by immunofluorescent staining using anti-neurofilament antibodies labeled with flurocein (obtained from Sigma Chemical Co., St. Louis).

Regeneration of the sciatic nerve occurred across the entire 12 mm distance in all graft sites wherein the gap was filled with the OP-1 gel. By contrast, empty silicone tubes and reverse autografts did not show nerve regeneration, and only one graft site containing the gel alone showed axon regeneration.

EXAMPLE 9

Morphogen-Induced Nerve Gap Repair (CNS)

Following axonal damage in vivo the CNS neurons are unable to resprout processes. Accordingly, trauma to CNS nerve tissue, including the spinal cord, optic nerve and retina, severely damages or destroys the neural pathways defined by these cells. Peripheral nerve grafts have been used in an effort to bypass CNS axonal damage. Successful autologous graft repair to date apparently requires that the graft site occur near the CNS neuronal cell body, and a primary result of CNS axotomy is neuronal cell death. The efficacy of morphogens described herein on CNS nerve repair, may be evaluated using a rat crushed optic nerve model such as the one described by Bignami, et al., *Exp. Eye Res.* 28: 63–69 (1979), the disclosure of which is incorporated herein by reference. Briefly, and as described therein, laboratory rats (e.g., from Charles River Laboratories, Wilmington, Mass.) are anesthetized using standard surgical procedures, and the optic nerve crushed by pulling the eye gently out of the orbit, inserting a watchmaker forceps behind the eyeball and squeezing the optic nerve with the forceps for 15 seconds, followed by a 30 second interval and second 15 second squeeze. Rats are sacrificed at different time intervals, e.g., at 48 hours, and at 3, 4, 11, 15 and 18 days after operation. The effect of morphogen on optic nerve repair can be assessed by performing the experiment in duplicate and providing morphogen or PBS (e.g., 25 ml solution, and 25 mg morphogen) to the optic nerve, e.g., just prior to the operation, concomitant with the operation, or at specific times after the operation.

In the absence of therapy, the surgery induces glial scarring of the crushed nerve, as determined by immunofluorescence staining for glial fibrillary acidic protein (GFA), a marker protein for glial scarring, and by histology. Indirect immunofluorescence on air-dried cryostat sections as described in Bignami, et al., *J. Comp. Neur.* 153: 27–38 (1974), using commercially available antibodies to GFA (e.g., Sigma Chemical Co., St. Louis). Reduced levels of GFA are anticipated in animals treated with the morphogen, evidencing the ability of morphogens to inhibit glial scar formation and to stimulate optic nerve regeneration.

EXAMPLE 10

Nerve Tissue Diagnostics

Morphogen localization in nerve tissue can be used as part of a method for diagnosing a neurological disorder or neuropathy. The method may be particularly advantageous for diagnosing neuropathies of brain tissue. Specifically, a biopsy of brain tissue is performed on a patient at risk, using standard procedures known in the medical art. Morphogen expression associated with the biopsied tissue then is assessed using standard methodologies, as by immunolocalization, using standard immunofluorescence techniques in concert with morphogen-specific antisera or monoclonal antibodies. Specifically, the biopsied tissue is thin sectioned using standard methodologies known in the art, and fluorescently labelled (or otherwise detectable) antibodies incubated with the tissue under conditions sufficient to allow specific antigen-antibody complex formation. The presence and quantity of complex formed then is detected and compared with a predetermined standard or reference value. Detection of altered levels of morphogen present in the tissue then may be used as an indicator of tissue dysfunction. Alternatively, fluctuation in morphogen levels may be assessed by monitoring morphogen transcription levels, either by standard northern blot analysis or in situ hybridization, using a labelled probe capable of hybridizing specifically to morphogen RNA and standard RNA hybridization protocols well described in the art.

Fluctuations in morphogen levels present in the cerebrospinal fluid or bloodstream also may be used to evaluate nerve tissue viability. For example, morphogens are detected associated with adendema cells which are known to secrete factors into the cerebrospinal fluid, and are localized generally associated with glial cells, and in the extracellular matrix, but not with neuronal cell bodies. Accordingly, the cerebrospinal fluid may be a natural means of morphogen transport. Alternatively, morphogens may be released from dying cells into cerebrospinal fluid. In addition, OP-1 recently has been identified in human blood, which also may be a means of morphogen transport, and/or a repository for the contents of dying cells.

Spinal fluid may be obtained from an individual by a standard lumbar puncture, using standard methodologies known in the medical art. Similarly, serum samples may be obtained by standard venipuncture and serum prepared by centrifugation at 3,000 RPM for ten minutes. The presence of morphogen in the serum or cerebral spinal fluid then may be assessed by standard Western blot (immunoblot), ELISA or RIA procedures. Briefly, for example, with the ELISA, samples may be diluted in an appropriate buffer, such as phosphate-buffered saline, and 50 ml aliquots allowed to absorb to flat bottomed wells in microtitre plates pre-coated with morphogen-specific antibody, and allowed to incubate for 18 hours at 4° C. Plates then may be washed with a standard buffer and incubated with 50 ml aliquots of a second morphogen-specific antibody conjugated with a detecting agent, e.g., biotin, in an appropriate buffer, for 90 minutes at room temperature. Morphogen-antibody complexes then may be detected using standard procedures.

Alternatively, a morphogen-specific affinity column may be created using, for example, morphogen-specific antibodies adsorbed to a column matrix, and passing the fluid sample through the matrix to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and confirmed by N-terminal sequencing. Morphogen concentrations in serum or other fluid samples then may be determined using standard protein quantification techniques, including by spectrophotometric absorbance or by quantitation by ELISA or RIA antibody assays. Using this procedure, OP-1 has been identified in serum.

Figure 5:
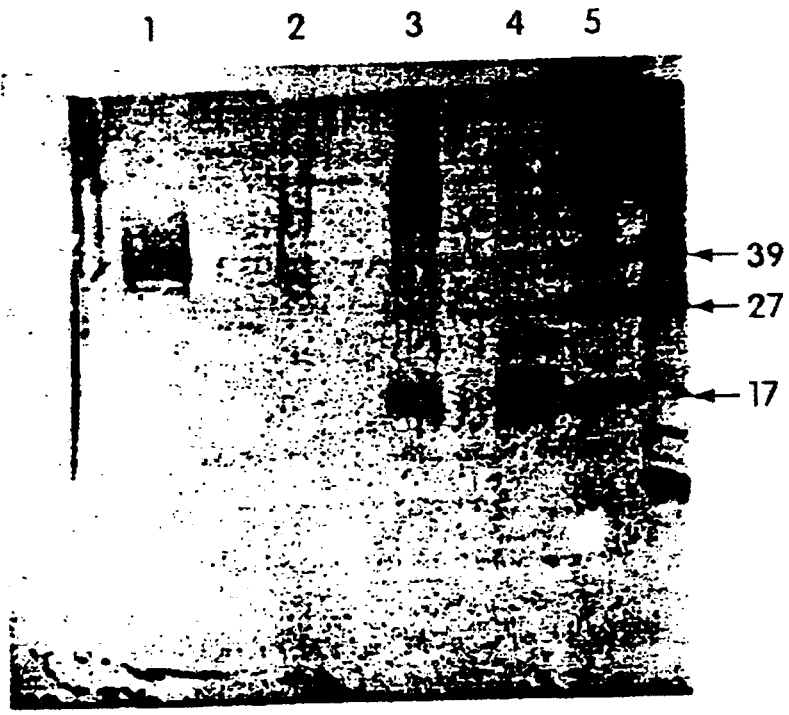
FIG. 5 is a photograph of an immunoblot demonstrating the presence of OP-1 in human serum.

OP1 was detected in human serum using the following assay. A monoclonal antibody raised against mammalian, recombinantly produced OP-1 using standard immunology techniques well described in the art and described generally in Example 14, was immobilized by passing the antibody over an activated agarose gel (e.g., Affi-Gel™, from Bio-Rad Laboratories, Richmond, Calif., prepared following manufacturer's instructions), and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP1 by standard immunoblot. FIG. 5 is an immunoblot showing OP1 in human sera under reducing and oxidized conditions. In the figure, lanes 1 and 4 are OP1 standards, run under oxidized (lane 1) and reduced (lane 4) conditions. Lane 5 shows molecular weight markers at 17, 27 and 39 kDa. Lanes 2 and 3 are human sera OP-1, run under oxidized (lane 2) and reduced (lane 3) conditions.

Morphogens may be used in diagnostic applications by comparing the quantity of morphogen present in a body fluid sample with a predetermined reference value, with fluctuations in fluid morphogen levels indicating a change in the status of nerve tissue. Alternatively, fluctuations in the level of endogenous morphogen antibodies may be detected by this method, most likely in serum, using an antibody or other binding protein capable of interacting specifically with the endogenous morphogen antibody. Detected fluctuations in the levels of the endogenous antibody may be used as indicators of a change in tissue status.

EXAMPLE 11

Alleviation of Immune Response-Mediated Nerve Tissue Damage

The morphogens described herein may be used to alleviate immunologically-related damage to nerve tissue. Details of this damage and the use of morphogens to alleviate this injury are disclosed in copending U.S. Ser. No. 753,059, filed Aug. 30, 1991, the disclosure of which is incorporated herein. A primary source of such damage to nerve tissue follows hypoxia or ischemia-reperfusion of a blood supply to a neural pathway, such as may result from an embolic stroke, or may be induced during a surgical procedure. As described in U.S. Ser. No. 753,059, morphogens have been shown to alleviate damage to myocardial tissue following ischemia-reperfusion of the blood supply to the tissue. The effect of morphogens on alleviating immunologically-related damage to nerve tissue may be assessed using methodologies and models known to those skilled in the art and described below.

For example, the rabbit embolic stroke model provides a useful method for assessing the effect of morphogens on tissue injury following cerebral ischemia-reperfusion. The protocol disclosed below is essentially that of Phillips, et al., *Annals of Neurology* 25: 281–285 (1989), the disclosure of which is herein incorporated by reference. Briefly, white New England rabbits (2–3 kg) are anesthetized and placed on a respirator. The intracranial circulation then is selectively catheterized by the Seldinger technique. Baseline cerebral angiography then is performed, employing a digital substration unit. The distal internal carotid artery or its branches then is selectively embolized with 0.035 ml of 18-hour-aged autologous thrombus. Arterial occlusion is documented by repeat angiography immediately after embolization. After a time sufficient to induce cerebral infarcts (15 minutes or 90 minutes), reperfusion is induced by administering a bolus of a reperfusion agent such as the TPA analogue FB-FB-CF (e.g., 0.8 mg/kg over 2 minutes).

The effect of morphogen on cerebral infarcts can be assessed by administering varying concentrations of morphogens, e.g., OP-1, at different times following embolization and/or reperfusion. The rabbits are sacrificed 3–14 days post embolization and their brains prepared for neuropathological examination by fixing by immersion in 10% neutral buffered formation for at least 2 weeks. The brains then are sectioned in a coronal plane at 2–3 mm intervals, numbered and submitted for standard histological processing in paraffin, and the degree of nerve tissue necrosis determined visually. Morphogen-treated animals are anticipated to reduce or significantly inhibit nerve tissue necrosis following cerebral ischemia-reperfusion in the test animals as determined by histology comparison with non-treated animals.

EXAMPLE 12

Animal Model for Assessing Morphogen Efficacy In Vivo

The in vivo activities of the morphogens described herein also are assessed readily in an animal model as described herein. A suitable animal, preferably exhibiting nerve tissue damage, for example, genetically or environmentally induced, is injected intracerebrally with an effective amount of a morphogen in a suitable therapeutic formulation, such as phosphate-buffered saline, pH 7. The morphogen preferably is injected within the area of the affected neurons. The affected tissue is excised at a subsequent time point and the tissue evaluated morphologically and/or by evaluation of an appropriate biochemical marker (e.g., by morphogen or N-CAM localization; or by measuring the dose-dependent effect on a biochemical marker for CNS neurotrophic activity or for CNS tissue damage, using for example, glial fibrillary acidic protein as the marker. The dosage and incubation time will vary with the animal to be tested. Suitable dosage ranges for different species may be determined by comparison with established animal models. Presented below is an exemplary protocol for a rat brain stab model.

Briefly, male Long Evans rats, obtained from standard commercial sources, are anesthetized and the head area prepared for surgery. The calvariae is exposed using standard surgical procedures and a hole drilled toward the center of each lobe using a 0.035K wire, just piercing the calvariae. 25 ml solutions containing either morphogen (e.g., OP-1, 25 mg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluorescence staining for glial fibrillary acidic protein, a marker protein for glial scarring, to qualitatively determine the degree of scar formation. Glial fibrillary acidic protein antibodies are available commercially, e.g., from Sigma Chemical Co., St. Louis, Mo. Sections also are probed with anti-OP-1 antibodies to determine the presence of OP-1. Reduced levels of glial fibrillary acidic protein are anticipated in the tissue sections of animals treated with the morphogen, evidencing the ability of morphogens to inhibit glial scar formation and stimulate nerve regeneration.

EXAMPLE 13

In vitro Model for Evaluating Morphogen Species Transport Across the Blood-Brain Barrier Described below is an in vitro method for evaluating the facility with which selected morphogen species likely will pass across the blood-brain barrier. A detailed description of the model and protocol are provided by Audus, et al., *Ann. N.Y. Acad. Sci* 507: 9–18 (1987), the disclosure of which is incorporated herein by reference.

Briefly, microvessel endothelial cells are isolated from the cerebral gray matter of fresh bovine brains. Brains are obtained from a local slaughter house and transported to the laboratory in ice cold minimum essential medium (MEM) with antibiotics. Under sterile conditions the large surface blood vessels and meninges are removed using standard dissection procedures. The cortical gray matter is removed by aspiration, then minced into cubes of about 1 mm. The minced gray matter then is incubated with 0.5% dispase (BMB, Indianapolis, Ind.) for 3 hours at 37° C. in a shaking water bath. Following the 3 hour digestion, the mixture is concentrated by centrifugation (1000×g for 10 min.), then resuspended in 13% dextran and centrifuged for 10 min. at 5800×g. Supernatant fat, cell debris and myelin are discarded and the crude microvessel pellet resuspended in 1 mg/ml collagenase/dispase and incubated in a shaking water bath for 5 hours at 37° C. After the 5-hour digestion, the microvessel suspension is applied to a pre-established 50% Percoll gradient and centrifuged for 10 min at 1000×g. The band containing purified endothelial cells (second band from the top of the gradient) is removed and washed two times with culture medium (e.g., 50% MEM/50% F-12 nutrient mix). The cells are frozen (−80° C.) in medium containing 20% DMSO and 10% horse serum for later use.

After isolation, approximately $5 \times 10^5$ cells/cm$^2$ are plated on culture dishes or 5–12 mm pore size polycarbonate filters that are coated with rat collagen and fibronectin. 10–12 days after seeding the cells, cell monolayers are inspected for confluency by microscopy.

Characterization of the morphological, histochemical and biochemical properties of these cells has shown that these cells possess many of the salient features of the blood-brain barrier. These features include: tight intercellular junctions, lack of membrane fenestrations, low levels of pinocytotic activity, and the presence of gamma-glutamyl transpeptidase, alkaline phosphatase, and Factor VIII antigen activities.

The cultured cells can be used in a wide variety of experiments where a model for polarized binding or transport is required. By plating the cells in multi-well plates, receptor and non-receptor binding of both large and small molecules can be conducted. In order to conduct transendothelial cell flux measurements, the cells are grown on porous polycarbonate membrane filters (e.g., from Nucleopore, Pleasanton, Calif.). Large pore size filters (5–12 mm) are used to avoid the possibility of the filter becoming the rate-limiting barrier to molecular flux. The use of these large-pore filters does not permit cell growth under the filter and allows visual inspection of the cell monolayer.

Once the cells reach confluency, they are placed in a side-by-side diffusion cell apparatus (e.g., from Crown Glass, Sommerville, N.J.). For flux measurements, the donor chamber of the diffusion cell is pulsed with a test substance, then at various times following the pulse, an aliquot is removed from the receiver chamber for analysis. Radioactive or fluorescently-labelled substances permit reliable quantitation of molecular flux. Monolayer integrity is simultaneously measured by the addition of a non-transportable test substance such as sucrose or inulin and replicates of at least 4 determinations are measured in order to ensure statistical significance.

EXAMPLE 14

Screening Assay for Candidate Compounds which Alter Endogenous Morphogen Levels

Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A more detailed description also may be found in U.S. Ser. No. 752,861, incorporated hereinabove by reference.

14.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for OP-1 production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+RNA for RNA analysis. To monitor de novo OP-1 synthesis, some cultures are labeled according to conventional procedures with an $^{35}$S-methionine/$^{35}$S-cysteine mixture for 6–24 hours and then evaluated to OP-1 synthesis by conventional immunoprecipitation methods.

14.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP1 may be detected using a polyclonal antibody specific for OP-1 in an ELISA, as follows.

1 mg/100 ml of affinity-purified polyclonal rabbit IgG specific for OP1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 ml aliquot of an appropriate dilution of each of the test samples of cell culture supernatant is added to each well in triplicate and incubated at 37° C. for 30 min. After incubation, 100 ml biotinylated rabbit anti-OP1 serum (stock solution is about 1 mg/ml and diluted 1:400 in BSB containing 1% BSA before use) is added to each well and incubated at 37° C. for 30 min. The wells are then washed four times with BSB containing 0.1% Tween 20–100 ml strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 ml substrate (ELISA Amplification System Kit, Life Technologies, Inc., Bethesda, Md.) is added to each well incubated at room temperature for 15 min. Then, 50 ml amplifier (from the same amplification system kit) is added and incubated for another 15 min at room temperature. The reaction is stopped by the addition of 50 ml 0.3 M sulfuric acid. The OD at 490 nm of the solution in each well is recorded. To quantitate OP1 in culture media, a OP1 standard curve is performed in parallel with the test samples.

Polyclonal antibody may be prepared as follows. Each rabbit is given a primary immunization of 100 μg/500 ml *E. coli* produced OP-1 monomer (amino acids 328–431 in SEQ ID NO:5) in 0.1% SDS mixed with 500 μl *E. coli* produced OP-1 monomer (amino acids 328–431 in SEQ ID NO:5) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP1 is detected in the serum using an ELISA assay. Then, the rabbit is boosted monthly with 100 mg of antigen and bled (15 ml per bleed) at days seven and ten after boosting.

Monoclonal antibody specific for a given morphogen may be prepared as follows. A mouse is given two injections of *E. coli* produced OP1 monomer. The first injection contains 100 mg of OP1 in complete Freund's adjuvant and is given subcutaneously. The second injection contains 50 mg of OP-1 in incomplete adjuvant and is given intraperitoneally. The mouse then receives a total of 230 mg of OP-1 (amino acids 307–431 in SEQ ID NO:5) in four intraperitoneal injections at various times over an eight month period. One week prior to fusion, both mice are boosted intraperitoneally with 100 mg of OP-1 (307–431) and 30 mg of the N-terminal peptide (Ser$_{293}$-Asn$_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP1-specific antibodies using OP-1 (307–431) as antigen. The cell fusion and monoclonal screening then are according to standard procedures well described in standard texts widely available in the art.

EXAMPLE 15

Morphogen-Induced Dendritic Growth in Spinal Motor Neurons In Vitro

In order to evaluate the effects of various neurotrophic proteins on neurite outgrowth, dissociated motor neurons from the spinal cord were exposed OP-1, BDNF, LIF, or GDNF in vitro.

Suspensions of motor neurons dissociated from the spinal cord of rat fetuses (E14 day) were prepared and plated essentially according to the method of Higgins, et al., *CULTURING NERVE CELLS*, Banker and Goslin, eds., MIT Press, pp. 177–205 (1991), incorporated by reference herein. Neurons were plated at low density (about 15 cells/mm$^2$) onto poly-D-lysine coated coverslips and maintained in a serum-free medium, Higgins, et al., *CULTURING NERVE CELLS* (1991). Cytosine-b-D-furanoside (1 µM) was added to the medium of all cultures for 48 hrs on the second day. This exposure was sufficient to render the cultures virtually free of nonneuronal cells for 30 days. Exposure to vehicle, OP-1, BDNF, LIF, or GDNF was initiated after the elimination of nonneuronal cells.

Cellular morphology was routinely assessed by intracellular injection of fluorescent dyes (4% Lucifer Yellow or 5% 5,6 dicarboxyfluorescein; Bruckenstein and Higgins, *Dev. Biol.* 128: 924–936 (1988). Only neurons whose cell bodies were at least 150 mm from their nearest neighbor were injected, because density-dependent changes in morphology occur when somata of motor neurons are separated by lesser distances. Highly purified recombinant human OP-1 was isolated from medium conditioned by transfected Chinese hamster ovary cells using S-Sepharose and phenyl-Sepharose chromatography followed by reverse phase high performance liquid chromatography as described previously. See Sampath, et al., *J. Biol. Chem.* 267: 20352–20362 (1992).

Cultures were immunostained with antibodies previously shown to react selectively with either axons or dendrites. Lein and Higgins, *Dev. Biol.* 136: 330–345 (1989). Dendritic probes included mAb to MAP2, to nonphosphorylated forms of the M and H neurofilaments, and to the transferrin receptor. Axonal probes included monoclonal antibodies against to synaptophysin, tau, and phosphorylated forms of the H and the M and H neurofilament subunits. All antigens were localized by indirect immunofluorescence using previously described procedures. Lein and Higgins, *Dev. Biol.* 136: 330–345 (1989). Image 1 Software (Universal Imaging) was used for the morphometric analyses of dendritic growth in immunostained cultures.

Addition of OP1 enhanced dendritic growth of spinal motor neurons. The dendrites that formed in the presence of OP-1 were significantly longer, had a larger number of branchpoints, and had a larger diameter than control spinal motor neurons. The effects of OP-1 appeared to be specific to dendrites OP-1 did not significantly affect the total length of axons. However, axon length was significantly increased by LIF and GDNF. These observations are summarized in Table I.

TABLE I

COMPARISON OF THE EFFECTS OF VARIOUS GROWTH HORMONES ON DENDRITIC GROWTH OF SPINAL MOTOR NEURONS

| Condition | Total dendritic length | # of dendritic branchpoints | Least somal diameter | Total axonal length |
|---|---|---|---|---|
| Control | 65.09 ± 6.7 | 0.65 ± 0.17 | 8.81 ± 0.32 | 180.95 ± 14.5 |
| OP-1 | 133.38 ± 10.0* | 1.40 ± 0.22* | 10.10 ± 0.44* | 200.20 ± 11.9 |
| BDNF | 56.58 ± 8.6 | 0.45 ± 0.78 | 9.56 ± 0.32 | 158.10 ± 9.8 |
| LIF | 59.64 ± 8.3 | 0.58 ± 0.20 | 8.87 ± 0.29 | 272.00 ± 24.2* |
| GDNF | 52.06 ± 12.6 | 0.76 ± 0.39 | 8.66 ± 0.24 | 288.89 ± 23.5* |

All measurements are in micrometers. Data are expressed as the mean ± SEM.
N = 40.
*Significantly different from Control group.

EXAMPLE 16

Morphogen-Induced Dendritic Growth in Various Neurons In Vitro

In order to further evaluate the effects of morphogens on neurite outgrowth, various neuronal populations were exposed OP-1 in vitro.

16.1 Cortical Neurons

The effects of morphogens on neurite outgrowth were evaluated in cortical neurons. Pregnant Balb/c mice (E 18) were euthanised by decapitation following $CO_2$ anesthesia and the embryos removed under sterile conditions. After carefully removing the meninges, the frontal cerebral cortex was dissected in sterile Hank's balanced salt solution (HBSS) without $Ca^{+2}/Mg^{+2}$ (Biowhittaker) containing 0.6% glucose and 0.5% HEPES (Sigma). The cortex was minced to 1 mm thick pieces and dissociated into a single-cell suspension using the following protocol. Pieces of frontal cortex were placed in 4.5 ml of $Ca^{+2}/Mg^{+2}$-free HBSS in a 50 ml conical culture tube and incubated in a water bath for 5 minutes at 37° C. Then, 0.5 ml of 2.5% trypsin solution (Gibco) was added and the tissue was then incubated for 10 minutes on a shaking device at 37° C. The supernatant was then removed and placed into another tube containing 0.5 ml fetal bovine serum (FBS; Gibco). Five ml of 0.025% Deoxyribonuclease I (Dnase; Calbiochem Corp.) in $Ca^{+2}/Mg^{+2}$-free HBSS was then added to the pellet and the incubation was continued for another 5 min on a shaking device at 37° C. At the end of incubation, the trypsin was inactivated by adding 0.5 ml FBS. The supernatant collected earlier was combined with the tissue and the cells were then concentrated by centrifugation (1000 rpm, 5 min.) and the supernatant was decanted. Fresh medium (2 ml) was added to resuspend the pellet which was further dissociated into a single-cell suspension by trituration using a pipet-tip.

The cells were plated in Neurobasal Medium (GIBCO), and supplemented with B-27 Supplement (GIBCO), 1 mM glutamine and penicillin/streptomycin. For all experiments, the cortical neurons were plated at low density ($1 \times 10^4$ cells/0.5 ml) on poly-D-lysine (50–100 µg/ml; Sigma) coated coverslips inserted into 24-well culture plate (Falcon). Cells were grown for two days in vitro at 37° C. in an atmosphere of 5% $CO_2$. OP-1 (1, 10, 30, or 100 ng/ml) was added either three hours or 24 hours after plating the cortical neurons. BSA was added to all wells at a final concentration of 500 µg/ml prior to adding OP-1. Control cultures consisted of culture medium and medium with BSA 500 µg/ml.

Mouse neurites were immunostained with M6, a mouse neuron-specific monoclonal antibody. Cells were first incubated in 0.1 M phosphate buffered saline (PBS) containing 1% BSA for 30 min at 25° C. and then exposed to M6 in PBS (1:10) for 24 hrs at 4° C. Immunofluorescent labeling for M6 was carried out using biotinylated secondary antibodies anti-rat IgG (Sigma; 3 µg/ml, 1:200, 1 hr at 37° C.) followed by avidin-TRITC conjugate (Sigma; 6.5 µg/ml, 1:400, 1 hr at 37° C., in the dark).

Axons were identified with a rabbit polyclonal antiserum to the 200 kDa neurofilament protein (NF-H; Sigma; 1:100, 91 µg/ml). A monoclonal antibody to microtubule-associated protein 2 (MAP2; Boehringer-Mannheim; 1:100, 20 µg/ml) was used as a specific marker of dendrites. To visualize these intracellular antigens, cells were permeabilized with 0.5% triton X-100 (TX) in 0.1 M PBS containing 1% BSA and 4% goat serum (GS; Sigma) for 1 hr at 25° C. Primary antibodies were diluted in 0.1M PBS, 1% BSA, 4% GS with 0.5% TX and incubated for 1 hr at 37° C. After the primary incubation, the cells were washed three times in PBS containing 4% GS. Labeling was detected with fluorescein- or rhodamine-conjugated antibodies (1:400 in PBS, BSA, GS, and TX, 1 hr at 37° C., in the dark). Mouse antibodies were visualized with fluorescein-coupled goat anti-mouse Ig (Boehringer-Mannheim). Rabbit or rat antibodies were visualized using indirect immunofluorescence with rhodamine-conjugated goat anti-rat or anti-rabbit Ig. Cultures were additionally stained with a nuclear stain, 4', 6-Diamidino-2-phenylindole dihydrochloride hydrate (DAPI; Sigma; 0.1 µg/ml, 5 min at room temperature). Coverslips were washed once in sterile water and let dry for 10 minutes before mounting onto glass slides in aqueous mounting solution (Fluoromount; Southern Biotechnology). Slides were kept refrigerated in the dark until examined.

Immunoreactive cells were examined in six different microscopic fields selected at random on a minimum of five coverslips for each experiment. Three experiments for each condition were carried out. Only isolated neurons whose cell bodies or processes that were not in contact with other neurons were analyzed. A total of 100 neurons were examined for each experimental condition.

For measurements of neurite length, neurons were examined at a final image magnification of 400×. Fluorescent images of the neurons were recorded with a CCD video camera (Dage) and analyzed with a Macintosh PowerMac (9500/200) and image processing program (NIH Image 1.59). Neurite lengths were measured by tracing the total length of any neurite extending from a neuron cell body. Recorded lengths were calibrated at the same magnification using a ciroscope slide micrometer. The number of primary dendrites per cell, the length of major neurites or axons, the length of primary dendrites, the length and number of secondary dendrites, the total length of primary or secondary dendrites, and the total neurite and dendrite length per cell were calculated. Analysis of statistical significance of any observed differences between monolayers was performed using Student's t-test or ANOVA (SPSS/Mac, version 6.1, SPSS Inc., Chicago, Ill.).

OP-1 enhanced dendritic growth of cortical neurons. The length of primary dendrites and the number and length of secondary dendrites were significantly increased in the presence of OP-1. The increase in dendritic growth was dose-dependent. Maximal growth was observed in the presence of 30–100 µg/ml of OP-1. The effects of OP-1 appeared to be dendrite-specific; OP1 did not significantly affect the cell morphology, body size, and axon length of cortical neurons. These observations are summarized in Table II.

TABLE II

EFFECTS OF OP-1 ON DENDRITIC GROWTH OF CORTICAL NEURONS

| Condition | Cell Body Diameter | Axon Length | # Primary | # Secondary |
|---|---|---|---|---|
| BSA 3 hrs | 15.9 ± 0.5 | 153.2 ± 9.1 | 3.5 ± 0.2 | 0.4 ± 0.14 |
| OP-1, 1 µg, 3 hrs | 15.98 ± 0.5 | 151.1 ± 6.2 | 3.5 ± 0.2 | 0.55 ± 0.13 |
| OP-1, 10 µg, 3 hrs | 17.8 ± 0.49 | 139.3 ± 8.5 | 4.0 ± 0.14 | 0.6 ± 0.13 |
| OP-1, 30 µg, 3 hrs | 17.74 ± 0.5 | 134.5 ± 6.9 | 4.0 ± 0.15 | 0.96 ± 0.14 |
| OP-1, 100 µg, 3 hrs | 17.3 ± 0.4 | 138.8 ± 6.6 | 3.6 ± 0.2 | 1.3 ± 0.2 |
| BSA 24 hrs | 16.3 ± 0.45 | 144.8 ± 5.9 | 3.5 ± 0.17 | 0.48 ± 0.11 |
| OP-1, 1 µg, 24 hrs | 15.6 ± 0.5 | 142.6 ± 10.9 | 3.4 ± 0.2 | 0.4 ± 0.1 |
| OP-1, 10 µg, 24 hrs | 16.7 ± 0.4 | 144.2 ± 8.16 | 3.2 ± 0.14 | 0.6 ± 0.1 |
| OP-1, 30 µg, 24 hrs | 16.5 ± 0.4 | 139.4 ± 7.8 | 3.5 ± 0.2 | 0.86 ± 0.12 |
| OP-1, 100 µg, 24 hrs | 17.3 ± 0.4 | 156.5 ± 11.1 | 3.0 ± 0.19 | 0.86 ± 0.17 |

| Condition | Length Primary | Length Secondary | Total Primary | Total Secondary | Total Dendrite |
|---|---|---|---|---|---|
| BSA 3 hrs | 15.4 ± 0.6 | 3.4 ± 0.8 | 51.4 ± 4.5 | 3.6 ± 1.5 | 54.9 ± 5.1 |
| OP-1, 1 µg, 3 hrs | 14.2 ± 0.4 | 4.7 ± 0.7 | 49.1 ± 3.5 | 5.7 ± 1.5 | 54.8 ± 4.6 |
| OP-1, 10 µg, 3 hrs | 20.5 ± 0.6 | 4.6 ± 0.6 | 81.6 ± 3.5 | 5.8 ± 1.2 | 87.5 ± 4.3 |
| OP-1, 30 µg, 3 hrs | 22.9 ± 0.5 | 7.6 ± 0.7 | 89.9 ± 4.6 | 11.1 ± 1.9 | 99.6 ± 5.7 |
| OP-1, 100 µg, 3 hrs | 23.7 ± 0.6 | 9.9 ± 0.75 | 87.7 ± 5.3 | 16.2 ± 2.9 | 103.9 ± 7.6 |
| BSA 24 hrs | 16.7 ± 0.5 | 4.6 ± 0.6 | 55.9 ± 3.5 | 4.7 ± 1.1 | 60.6 ± 4.1 |
| OP-1, 1 µg, 24 hrs | 13.7 ± 0.5 | 3.7 ± 0.7 | 46.3 ± 3.6 | 4.1 ± 1.0 | 50.4 ± 4.0 |
| OP-1, 10 µg, 24 hrs | 16.3 ± 0.6 | 4.8 ± 0.7 | 50.8 ± 3.1 | 5.3 ± 7.7 | 56.1 ± 3.6 |
| OP-1, 30 µg, 24 hrs | 18.9 ± 0.5 | 7.4 ± 0.8 | 65.6 ± 4.5 | 9.6 ± 1.6 | 75.5 ± 5.1 |
| OP-1, 100 µg, 24 hrs | 22.1 ± 0.8 | 7.6 ± 1.0 | 64.0 ± 6.4 | 10.5 ± 2.2 | 74.8 ± 7.8 |

Three separate experiments were performed for each condition. At least 30 isolated cells, identified by MAP2 and NE-H immunolabeling and not touching other neurons were analyzed for each experiment after 2DIV using computer assisted image analysis. Data are expressed as means ± standard error.

16.2 Hippocampal Neurons

The effects of morphogens on neurite outgrowth were evaluated in hippocampal neuerons. Primary hippocampal cultures were prepared according to the method of Banker, et al. See Banker & Cowan *Brain Res.* 126: 397–425 (1977); Banker & Goslin, *CULTURING NERVE CELLS* (1991). A very low density of neurons was plated over a monolayer of glial cells plated on poly-D-lysine coated coverslips and maintained in a serum-free medium. Cellular morphology was assessed by immunostaining for MAP2. Dendritic length and branching was quantified using the Shoil concentric ring analysis. Under these control conditions, hippocampal neurons produce 4–6 minor processes. Over the first 24–48 hours, one of the processes grows rapidly and becomes an axon. The other processes extend very slowly and develop into mature dendrites after 6–10 days.

Figure 6:
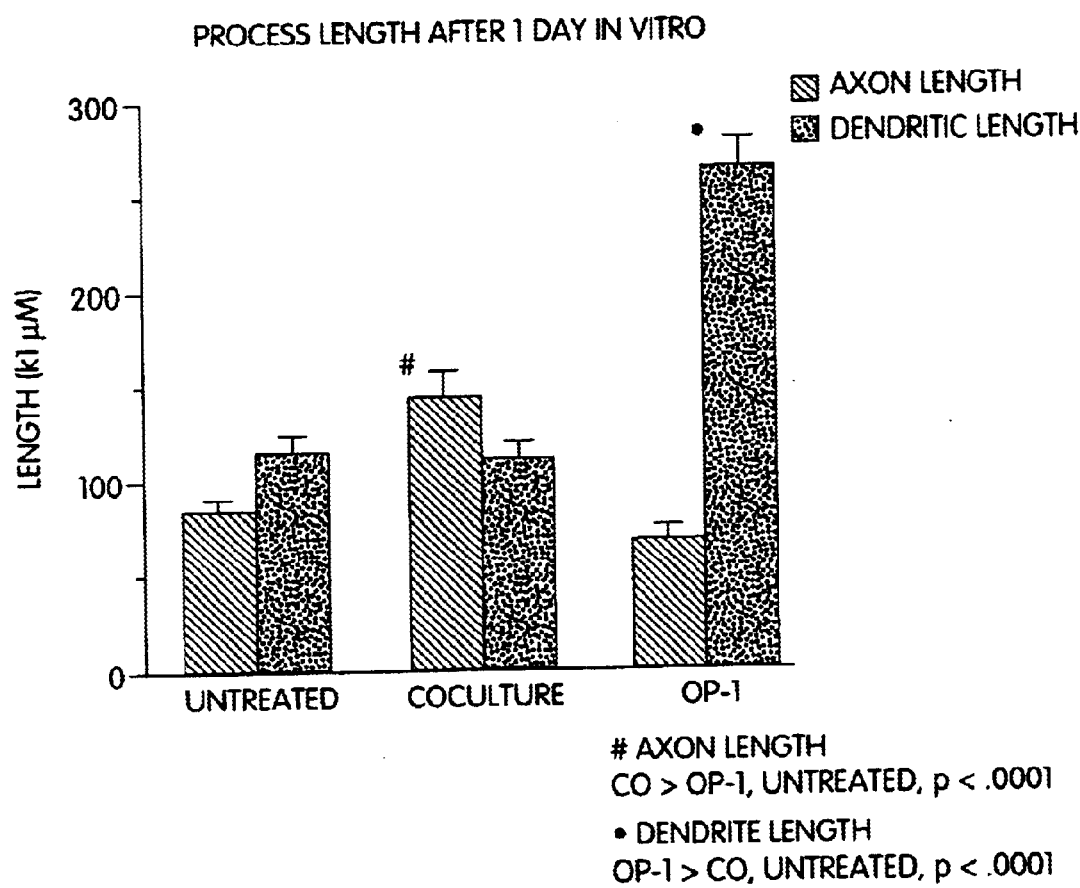
FIG. 6 is a bar graph comparing the effects of OP-1 and glial cells on axonal and dendritic length after one day in vitro.
Figure 7:
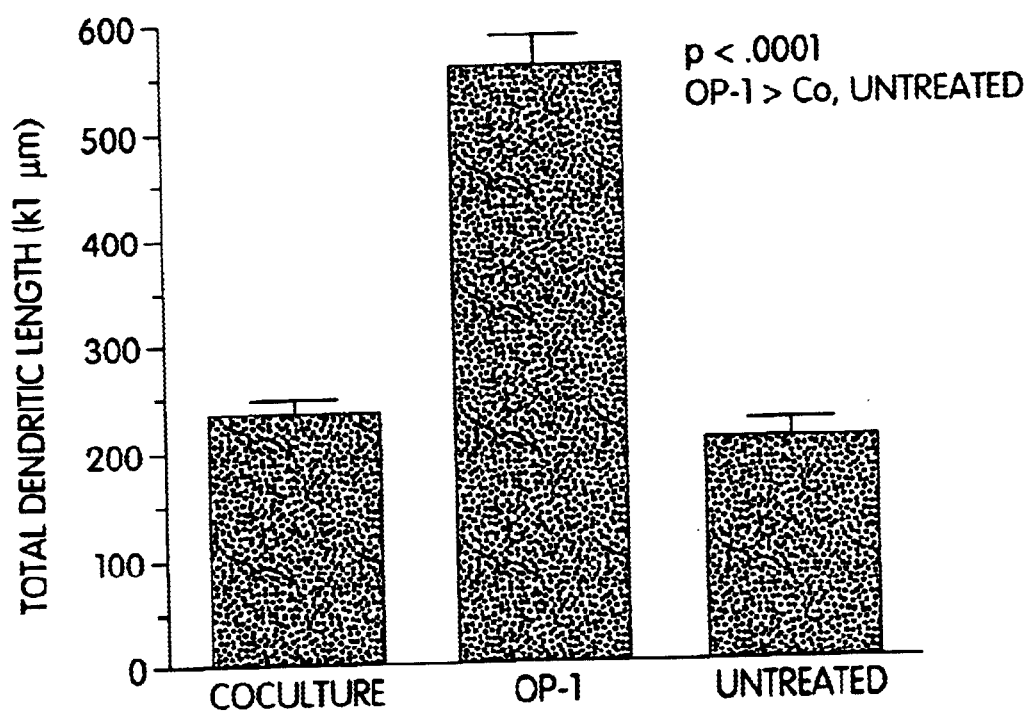
FIG. 7 is a bar graph comparing the effects of OP-1 and glial cells on axonal and dendritic length after three days in vitro.
Figure 8:
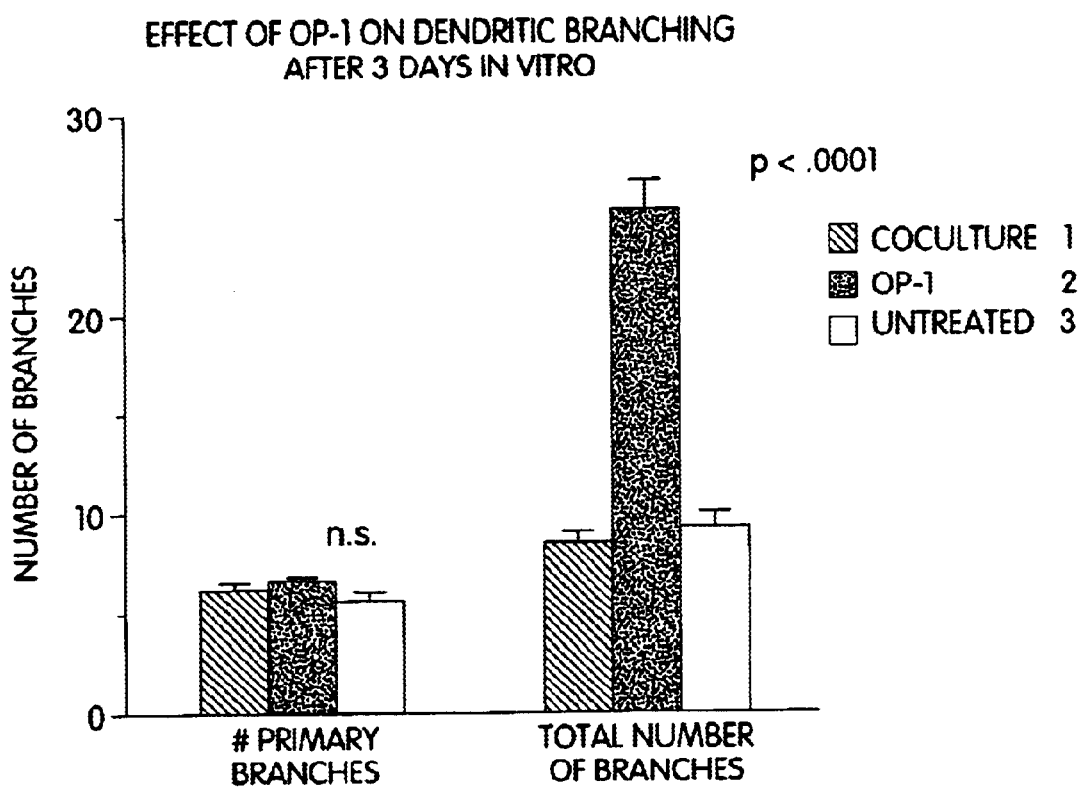
FIG. 8 is a bar graph comparing the effects of OP-1 and glial cells on dendritic branching after three days in vitro.

Because glial cells secrete trophic factors into the medium that are critical for the development of hippocampal neurons, this culture method was modified to assess the effects of OP-1. Hippocampal neurons were plated in a serum-free medium without glial cells. In the absence of glial cells, OP-1 markedly enhanced the rate and extent of dendritic development of hippocampal neurons cultured in serum-free medium. OP-1-treated neurons had significantly increased number of Shoil ring intersections (39.6 vs. 16.02), dendritic length (FIGS. 6 and 7) and number of terminal branches (13.05 vs. 6.64; FIG. 8). There were no significant differences in the number of primary dendrites. The effects of OP-1 appeared to be dendrite-specific in this cell type. As illustrated in FIG. 6; OP-1 did not significantly affect the total length of axons.

16.3 Sympathetic Neurons

(i) Effects of OP-1 on Dendritic Growth

In order to assess the effects of morphogens on sympathetic neurons, suspensions of neurons dissociated from the superior cervical ganglia of Sprague-Dawley rat fetuses (19–21 day) or rat pups (1–3 day postnatal) were exposed to OP-1. The suspension were prepared according to the method of Higgins, et al., *CULTURING NERVE CELLS*, Banker and Goslin, eds., MIT Press, pp. 177–205 (1991), the teachings of which herein incorporated by reference. Equivalent results were obtained with pre- and postnatal animals. Neurons were plated at low density (about 15 cells/mm 2) onto poly-D-lysine coated coverslips and maintained in a serum-free medium (Higgins, et al., *CULTURING NERVE CELLS* (1991)) containing NGF (100 ng/ml). Cytosine-b-D-furanoside (1 $\mu$M) was added to the medium of all cultures for 48 hrs on the second day. This exposure was sufficient to render the cultures virtually free of non-neuronal cells for 30 days. To label sympathetic neuroblasts, ganglia from 15-day embryos were grown in explant culture for 18 hrs in the presence of $^3$H-(methyl)-thymidine (0.3 mCi/ml, ICN) before being dissociated. Because NT3 (50 ng/ml) enhances the survival of immature sympathetic neurons, Birren, et al., *Develop.* 119: 597–610 (1993), it was added to the NGF-containing medium during the period of explant culture and the next 4 days in vitro. As in cultures of sympathetic neurons, exposure to NGF, OP-1, or both, was initiated after the elimination of nonneuronal cells.

Cellular morphology was routinely assessed by intracellular injection of fluorescent dyes (4% Lucifer Yellow or 5% 5,6 dicarboxyfluorescein; Bruckenstein and Higgins, *Dev. Biol.* 128: 924–936 (1988)). Only neurons whose cell bodies were at least 150 mm from their nearest neighbor were injected, because density-dependent changes in morphology occur when somata of sympathetic neurons are separated by lesser distances. Highly purified recombinant human OP-1 was isolated from medium conditioned by transfected Chinese hamster ovary cells using S-Sepharose and phenyl-Sepharose chromatography followed by reverse phase high performance liquid chromatography as described previously. See Sampath, et al., *J. Biol. Chem.* 267: 20352–20362 (1992).

Under control conditions, sympathetic neurons typically extended a single process during the first 24–48 hrs in vitro. This process has the cytoskeletal and ultrastructural characteristics of an axon. The axon continued to elongate during the next few weeks and generate an elaborate plexus. The basic morphology of the cells, however, remained essentially unchanged, with 80% of the neurons still being unipolar after one month in vitro. Most of the remainder had either two axons (13% of the cells) or an axon and a short dendrite (7%). Thus, the mean number of processes at this time was 1.13±0.06 axons/cells and 0.07±0.04 dendrites/cell.

Figure 9A:
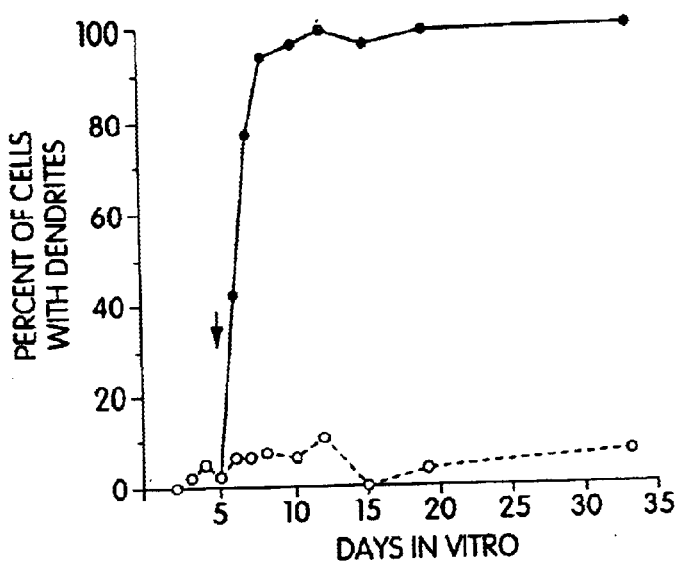
FIG. 9 (Panels A–C) are line graphs depicting a time course of the response of cultured sympathetic neurons to OP-1. Intracellular dye injections (N>30 for each point) were performed at various times to determine: the percentage of cells with dendrites (Panel A); the mean number of dendrites/cell (Panel B); and the number of axons/cell (Panel C). The bars shown in Panel B represent the SEM; where bars are not shown, the SEM was smaller than the size of the symbol. Open symbols, control; filled symbols, cells supplemented with 100 ng/ml OP-1 during the time course study.
Figure 9B:
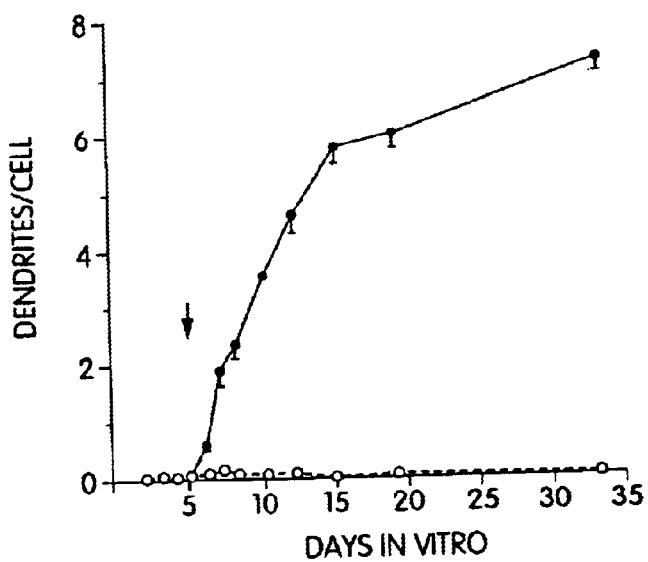
Figure 9C:
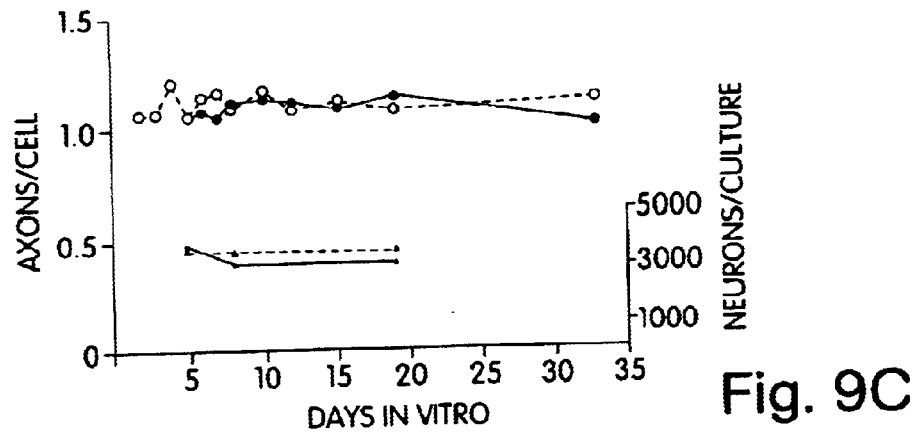

Exposure to OP-1 caused sympathetic neurons to form additional processes. This response was relatively slow, with only 42% of the cells forming a second process within 24 hrs. However, virtually all cells (94%) had begun to respond to maximally effective concentrations of OP1 within three days. The processes that formed in the presence of OP-1 had the appearance of dendrites. These processes were broad-based (up to 5 $\mu$m diameter), exhibited a distinct taper, and branched in a "Y"-shaped pattern, with daughter processes being distinctly smaller than the parent process. Dendrites were much thicker than sympathetic axons and, unlike axons, they ended locally, usually extending less than 300 mm from the soma. The mean number of dendrites/cell continued to increase during a four week exposure to OP-1, with most of the change occurring during the first 10 days of treatment. After four weeks, OP-1-treated neurons had a mean of 7.3±0.3 dendrites/cell, representing a 100-fold increase over control cells. During this time, the size of the dendritic arbor also increased, with cells progressing from simple cells to a more complicated morphology. These observations are summarized in panels A, B and C of FIG. 9.

The effects of OP-1 appeared to be dendrite-specific in this cell type. The effects of OP-1 on initial axon growth during the first 48 hrs in culture were examined. OP-1 did not affect the rate at which axons were initially extended, or the number of axons extended per cell. Cell number also remained constant during the exposure to OP-1, indicating that the morphogen was not acting by enhancing the survival of a subpopulation of neurons, as shown in panel C of FIG. 9. The effects of OP-1 were also examined in the delayed introduction paradigm, and no increase in axon number was observed.

(ii) Effects of Various Concentrations of OP-1 on Dendritic Growth

In order to assess whether the effects of morphogens on dendritic growth were concentration-dependent, suspensions of neurons dissociated from the superior cervical ganglia were exposed to various concentrations of OP-1.

Figure 10:
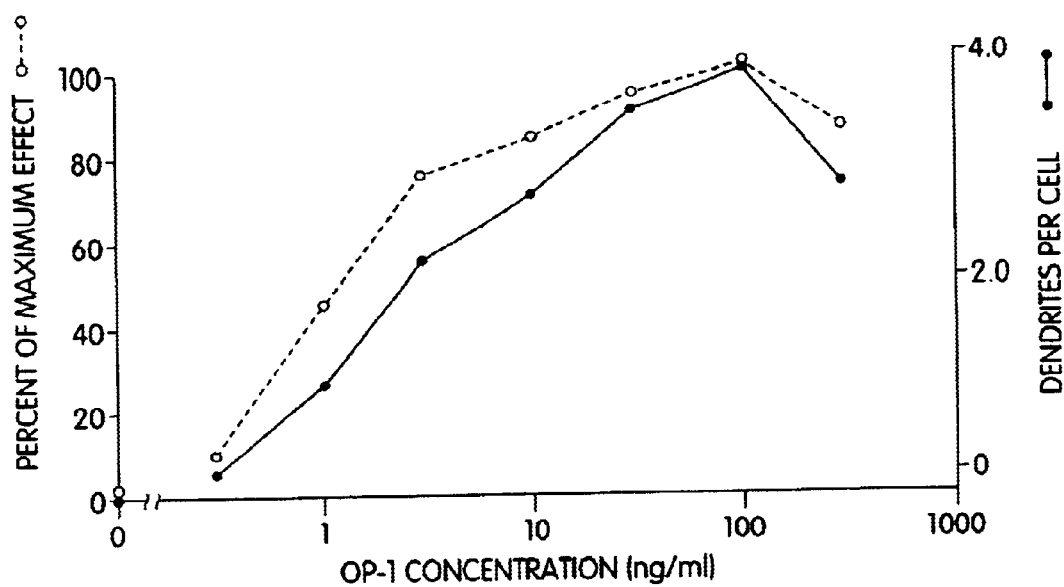
FIG. 10 is a line graph depicting the effects of varying concentrations of OP-1 on dendritic growth. Sympathetic neurons were exposed to OP-1 in culture for three days and then immunostained with a dendrite-specific mAb (SMI 32). Percentage of cells with dendrites, open circles; mean number of dendrites per cell, filled circles.

The effects of OP1 were concentration-dependent (FIG. 10). Significant changes in dendritic growth could be detected with concentrations as low as 300 pg/ml, and half-maximal effects were observed at about 2 ng/ml. Maximal dendritic growth was obtained with medial concentrations between 30 and 100 ng/ml. Although typically added to the medium on day 5, earlier initiation of dendritic growth (by the third day of culture) could be obtained by adding OP1 to the medium at the time of plating. No dendritic growth was detected in cultures in which the OP1 (1 μg/ml) had been allowed to absorb to coverslips before plating cells.

It appeared that several parameters of dendritic growth, including the percentage of cells with dendrites, the mean number of dendrites/cell, dendritic length (not shown), changed over the same concentration range. In addition, three other changes were observed in cellular morphology in this morphogen concentration range. As had been observed while dendritic growth is occurring in vivo, the somata became larger. In addition, the nuclei became less eccentric, and the axons formed small fascicles.

(iii) Effects of Various Morphogens on Dendritic Growth

Using the methods described above, other morphogens were tested for their capacity to induce dendritic growth of sympathetic neurons and their effects on the expression of cytoskeletal proteins. Sympathetic neurons were dissociated from the superior cervical ganglia of Holtzman (Harlan Sprague-Dawley) rat fetuses (E21) or pups (1 day postnatal) and plated onto poly-D-lysine-coated coverslips according to the method of Higgins, et al., *CULTURING NERVE CELLS*, Banker and Goslin, eds., MIT Press, pp. 177–205 (1991). The cells were maintained in a serum-free medium that contains nerve growth factor (100 ng/ml), and nonneuronal cells were eliminated by exposure to cytosine-β-D-arabinofuranoside (1 μM) for 48–72 h beginning on the second day after plating. The morphology of the neurons was routinely assessed by intracellular injection of the fluorescent dye Lucifer yellow (4%) and by immunostaining with dendrite-specific antibodies. These included monoclonal antibody SMI 32 (Sternberger Monoclonals, Inc.) which recognizes nonphosphorylated epitopes on the H and M neurofilament subunits and AP20 (Sigma) and SMI 52 (Sternberger Monoclonals, Inc.) which both react with microtubule-associated protein-2 (MAP2). Highly purified recombinant human proteins (BMP-2, BMP-3 and CDMP-2) and Drosophila 60A were prepared as described previously for OP-1.

For Western blot analysis of cytoskeletal proteins, sympathetic neurons were plated onto poly-D-lysine coated 35 mm dishes and treated with 50 ng/ml of BMP-2, OP-1, 60A or CDMP-2 for five days. Cells were then scraped off dishes in 50 mM Tris buffer (pH 7.4) containing 0.1% SDS, 2% 2-mecaptoenthanol and 1 mM EDTA and homogenized by passing through a 23 gauge needle at 4° C. Cell extracts were centrifuged at 12000xg for 15 minutes and the protein concentrations of the supernatants were determined using the Bradford dye reagent (Bio-Rad). Equal amounts of proteins were resolved by SDS-PAGE, electrophoretically transferred onto a nitrocellulose membrane, and probed with antibodies to MAP2 or an antibody SMI 31 (Sternberger Monocionals, Inc.) to the phosphorylated forms of the H and M neurofilament subunits. Detection was accomplished using Chemiluminescent Substrate (Pierce Chemical Co.) after sequential treatment with biotinylated goat antimouse IgG (HyClone Laboratories, Inc.) and with horseradish peroxidase-conjugated streptavidin (Amersham).

Figure 11:
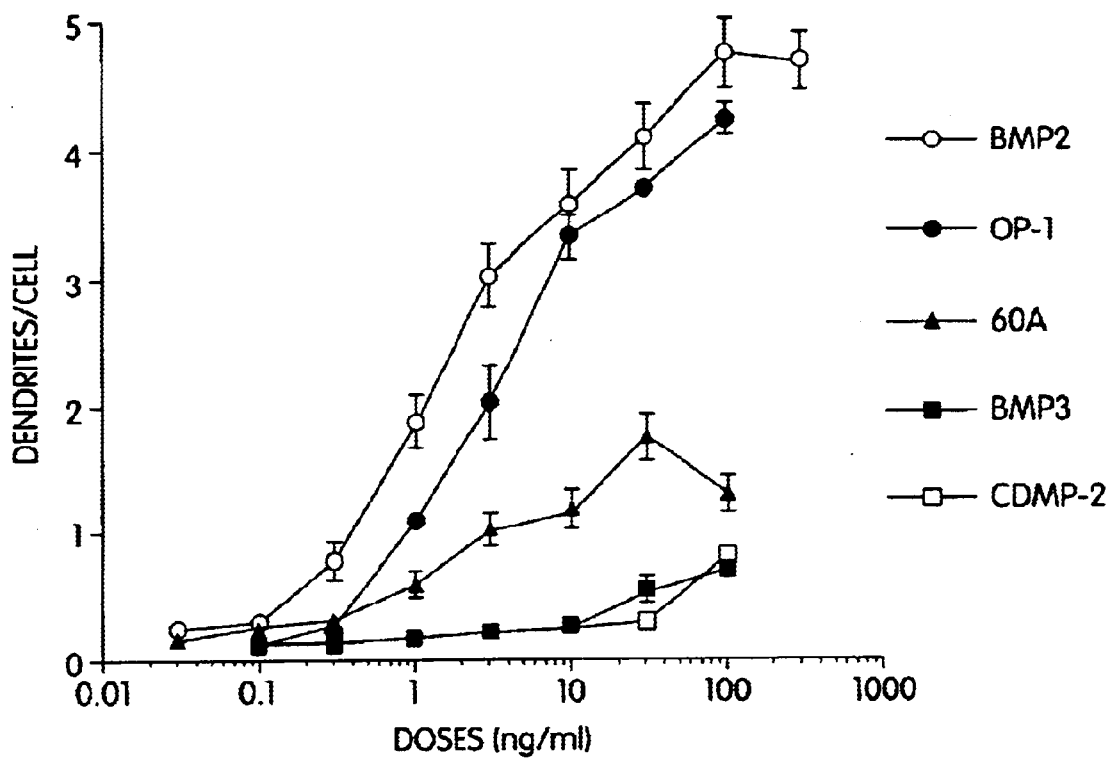
FIG. 11 is a line graph depicting the effects of varying concentrations of different morphogens on dendritic growth. Sympathetic neurons were exposed to various concentrations of BMP-2, OP-1, 60A, BMP-3 or CDMP-2 beginning on the fifth day in vitro and then immunostained on day 10 with a dendrite-specific antibody (SMI 32). Data are presented as the mean±SEM. N=30.

As illustrated in FIG. 11, all the morphogens tested (i.e., OP-1, BMP-2, BMP-3, CDMP-2, and 60A) induced significant dendritic growth in sympathetic neurons. However, significant variations in efficacy were observed. Treatment with maximally effective concentrations (50 ng/ml) of BMP-2 or OP-1 for five days caused virtually all of the neurons to form dendrites (Table III). These processes exhibited a distinct taper, branched at "Y" shaped angles, and extended approximately 100 μm from the cell bodies after five days of treatment. Examination of concentration effect relationships (FIG. 11) revealed that the $EC_{50}$ for BMP-2 (1.7 ng/ml) was similar to that for OP-1 (1.8 ng/ml) and that maximally effective concentrations of these two growth factors had equivalent effects on the cells, as assessed by both the number of dendrites per cell and the length of the longest dendrite (Table III). Moreover, the effects of OP-1 and BMP-2 were not additive (data not shown) suggesting that the two ligands may share aspects of a common signaling pathway. The Drosophila 60A protein also stimulated dendritic growth and the $EC_{50}$ (2.7 ng/ml) for this activity was similar to that for OP-1 and BMP-2. However, 60A was less efficacious, and at maximally effective concentrations caused cells to form fewer dendrites (1.2/cell) than either OP-1 or BMP-2 (4.6 or 4.9/cell, respectively). BMP-3 and CDMP-2 only produced a statistically significant increase in dendritic growth at the highest concentration tested (100 ng/ml). The different efficacies for promoting dendrite growth may indicate relatively stringent structural requirements for this biological activity. OP-1, BMP-2 and 60A, which share a high sequence homology (89–90%) in the conserved seven-cysteine skeleton sequence, had much higher efficacies than BMP-3 and CDMP-2, which share 78% and 82% homology, respectively, with the reference sequence of OP-1. See FIG. 1.

TABLE III

COMPARISON OF THE EFFECTS OF VARIOUS MORPHOGENS ON DENDRITIC GROWTH OF SYMPATHETIC NEURONS

| Growth Factor | Dendrites per Cell | % Cells with Dendrites | Length of the Longest Dendrite (pm) | $EC_{50}$ (ng/ml) |
|---|---|---|---|---|
| Control | 0.20 ± 0.14 | 13.3 | 6.0 ± 4.3 | |
| OP-1 | 4.62 ± 0.49* | 100.0 | 112.3 ± 5.6 | 1.84 |
| BMP-2 | 4.93 ± 0.46* | 100.0 | 107.1 ± 5.6 | 1.66 |
| 60A | 1.20 ± 0.26* | 73.3 | 50.7 ± 9.0 | 2.70 |
| BMP-3 | 0.44 ± 0.22 | 25.0 | 16.3 ± 7.6 | 26.05 |
| CDMP-2 | 0.25 ± 0.14 | 18.8 | 12.5 ± 6.7 | 98.38 |

Sympathetic neurons were exposed to 50 ng/ml of each of the growth factors for five days and then immunostained with a dendrite specific antibody (SMI 32). Cellular morphology was analyzed by fluorescence microscopy using Metamorph software Universal Imaging). Data are presented as the mean ± SEM; N = 20–30.
*p < 0.01 vs control (Student's t-test).

The effects of various morphogens on the expression of cytoskeletal proteins were also assessed using methods described above. After nonneuronal cells had been eliminated, sympathetic neurons were treated with control medium or with 50 ng/ml of OP-1, BMP-2, 60A or CDMP-2, for five days. Cultures were then solubilized and subjected to Western blot analysis for MAP2 (primarily located in dendrites) and for phosphorylated forms of the H and M neurofilament subunits (primarily located in axons). The efficacy of the various morphogens in increasing MAP2 expression correlated with their ability to induce dendritic growth. Cultures exposed to BMP-2, OP-1 or 60A exhibited significant increases (3.0±0.4, 2.3±0.4, and 1.8±0.3 fold, respectively) in the expression of high molecular weight forms of MAP2 when compared to control cultures. The level of expression of MAP2 was not significantly increased in cultures exposed to CDMP-2. None of the morphogens tested affected the expression of the phosphorylated forms of the H and M neurofilament subunits. These results show that morphogens enhance the expression of a microtubule-associated protein which is found in dendrites and which is required for the growth of these processes. These observations suggest that regulation of MAP2 expression may be one of the mechanisms by which morphogens regulate the morphological development of sympathetic neurons.

(iv) Comparison of OP-1 to Other Growth Factors

In order to evaluate whether the effects on dendritic outgrowth are specific to morphogens, the effects of other growth factors on dendritic growth were compared to those of OP-1.

Mature human recombinant OP-1 was isolated from medium conditioned by transfected Chinese hamster ovary cells using S-Sepharose and phenyl-Sepharose chromatography followed by reverse phase high performance liquid chromatography as described above. Ciliary neurotrophic factor (CNTF) was purified from rat sciatic nerve Manthorpe, et al., *Brain Res.* 367: 282–286 (1986), the teachings of which are herein incorporated by reference) and activin A was generously provided by Ralph Schwall (Genentech). Other growth factors were obtained from commercial sources: GIBCOBRL (IL-1β, IL-3, IL-4, IL-6, IL-7; LIF, EGF, GM-CSF, RANTES, MCAF, TGF-α, TGF-β1 and 3, rat gamma interferon); Collaborative Research (HGF, PDGF); Boehringer (IL-2); and Promega (IL-8); R&D Systems (BDNF, NT3, NT4, bFGF).

As summarized in Table IV, dendritic growth was not observed in the presence of TGF-β1, TGF-β3, activin A or inhibin, all of which are members of the TGF-β family but are not members of the structurally and functionally distinct morphogen sub-family. In addition, negative results were obtained with most neurotrophins and nine other growth factors known to affect neuronal survival or differentiation (Table IV). In other experiments, negative results were also obtained with: TGF-β2, interleukins 1β, 2, 3, 4, 6, 7, and 8, PDGF, HGF, GM-CSF, MCAF, RANTES, TGF-α and gamma interferon. Thus, it would appear that the dendrite-promoting effect of morphogens is a highly specific response that is observed with a very limited subset of growth factors.

TABLE IV

COMPARISON OF THE EFFECTS OF OP-1 AND OTHER GROWTH FACTORS ON DENDRITIC GROWTH

| GROWTH FACTOR | MEAN NUMBER OF DENDRITES/CELL |
| --- | --- |
| NONE | 0.8 ± 0.04 |
| OP-1 | 3.08 ± 0.20 |
| TGF-β1 | 0.17 ± 0.09 |
| TGF-β3 | 0.00 ± 0.00 |
| INHIBIN | 0.20 ± 0.10 |
| ACTIVIN A | 0.08 ± 0.05 |
| BDNF | 0.11 ± 0.05 |
| NT3 | 0.11 ± 0.07 |
| NT4 | 0.32 ± 0.11 |
| CNTF | 0.10 ± 0.05 |
| LIF | 0.13 ± 0.07 |
| EUF | 0.07 ± 0.07 |
| bFGF | 0.03 ± 0.03 |

Beginning on day 5, cultures of sympathetic neurons were exposed to varying concentrations of growth factors. Seven to eight days later, the mean number of dendrites/cell was assessed by intracellular dye injection. Only the results obtained with the highest concentration tested (100 ng/ml) are shown in this table, but lower concentrations yielded similar results. N > 30 cells for each condition (v) Role of Morphogens in Glial-Induced Dendritic Growth Sympathetic neurons extend only a single axon when grown in the absence of serum or nonneuronal cells. In contrast, co-culturing sympathetic neurons with glial cells causes these neurons to form dendrites. In order to assess the potential role of morphogens in glial-induced dendritic growth, neuron and glial cells were co-cultured in the presence of a monoclonal antibody (mAb) raised against hOP-1.

Dendritic growth in sympathetic neurons grown with astrocytes or Schwann cells was inhibited by 40–60% in the presence of a hOP-1 mAb. SDS-PAGE analyses by hOP-1 mAb of proteins immunoprecipitated from neuron-glia co-cultures revealed several bands, the molecular weights of which corresponded to the cellular and secreted forms of hOP-1. Immunocytochemical analyses of co-cultures indicate that both neurons and glia express cytoplasmic and surface staining for OP1 and BMP-6. Similar patterns of immunoreactivity were observed in glia grown in the absence of neurons. However, neurons cultured in the absence of glia expressed cytoplasmic but not surface staining for OP-1 or BMP-6. These data are consistent with a role for morphogens in glia-induced dendritic growth.

EXAMPLE 17

Morphogen-Induced Synaptic Formation

Figure 12:
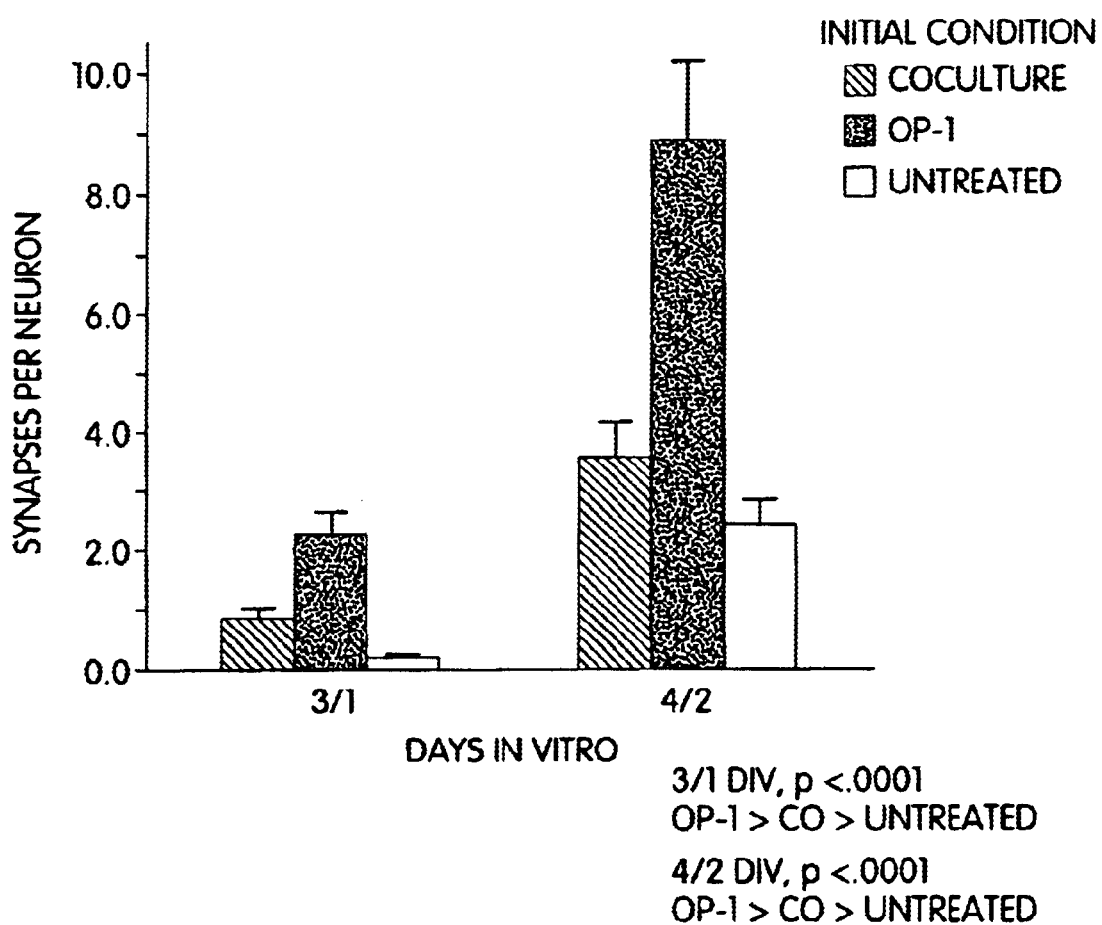
FIG. 12 is a bar graph comparing the effects of OP-1 and glial cells on synapse formation after three and four days in vitro.

As described in Examples 15 and 16, OP-1 induces dendritic growth in various populations of cultured neurons. To determine if these dendrites are receptive to innervation, OP-1-treated cultured hippocampal neurons were immunostained with antibodies to MAP2 and synapsin. Sites of presynaptic contact were defined by puncta of synapsin immunoreactivity. Given the poor growth of axons in cultured hippocampal neurons maintained in a serum-free medium, a heterochronic culture technique was used to assess the ability of the OP-1-extended dendrites to receive axonal contacts. Cultured neurons were grown in the presence of OP1 for three days. New neurons were plated on top of these more mature neurons and fixed one day later. Previous work has shown that axonal contacts will form within 24 hours of plating if more mature dendrites are present within the culture. Fletcher, et al., *J. Neurosci* 14: 6695–6706 (1994). Using this heterochronic culture technique, synapsin positive aggregates were found surrounding OP-1-induced dendrites. As illustrated in FIG. 12, OP-1-reated cultured hippocampal neurons had a significantly higher number of synapses per neuron than untreated neurons or neurons co-cultured with glial cells. These observations suggest that the OP1 induced dendritic outgrowth produces dendrites that are receptive to innervation.

EXAMPLE 18

Morphogen-Induced Dendritic Growth and Synaptogenesis In Vivo

In order to assess the effects of morphogen on dendritic growth in vivo, rats are injected intraperitoneally once per day with OP1 at dose of 2 mg/kg. The control group consists of rats injected intraperitoneally with the vehicle (20 mM arginine (pH 9.0), 150 mM NaCl with 0.1% Tween 80). After seven days, rats are anesthetized with ether and the superior cervical ganglia, hippocampus, and hypoglossal nucleus are removed. Subsequently, rats are perfused with paraformaldehyde and the kidney and retina are removed.

Superior cervical ganglia are desheathed and pinned in a chamber superfused with an oxygenated physiological saline. For intracellular staining, neurons are impaled with triangular glass electrodes filled with a 4% solution of horseradish peroxidase (HRP). HRP is introduced into the cell by iontophoresis and the reaction product is visualized by the pyrocathecol-phenylenediamine method. Hanker, et al., *Histochem. J.* 9: 789–792 (1977); for details see Purves and Hume, *J. Neurosci.* 1: 441–452 (1981); Forehand and Purves, *J. Neurosci.* 4: 1–12 (1984). Five to ten cells/ganglion are injected. After allowing two hours for dye diffusion, the ganglia are fixed in 4% formaldehyde overnight. After dehydration, stained neurons are viewed at 300× in whole-mount preparations and traced with the aid of a camera lucida.

To confirm the light microscopic identification of processes and to assess the state of differentiation of the dendrites formed in the presence of OP-1, superior cervical ganglia are immunostained with antibodies previously shown to react selectively with either axons or dendrites. Lein and Higgins, *Dev. Biol.* 136: 330–345 (1989). Monoclonal antibodies (mAb) to MAP2 (e.g., AP14), to nonphosphorylated forms of the M and H neurofilaments (SMI 32, Stembery-Meyer Immunocytochemicals), and to the transferrin receptor (MRC OX-26, Serotech) are used as dendritic markers and mAb to synaptophysin (SY-38, Boehringer Mannheim), tau (e.g., Tau 1), and phosphorylated forms of the H (NE14, Boehringer Mannheim) and the M and H (SMI 31, Stembery-Meyer Immunocytochemicals) neurofilament subunits are used as axonal markers. All antigens are localized by indirect immunofluorescence using previously described procedures. Lein and Higgins, *Dev. Biol.* 136: 330–345 (1989). Image 1 Software (Universal Imaging) is used for the morphometric analyses of dendritic growth in immunostained cultures. In addition, in order to determine the effects of OP1 on synaptogenesis in superior cervical ganglia in vivo, neurons are immunostained with antibodies to synapsin. Sites of presynaptic contact are defined by puncta of synapsin immunoreactivity.

Hippocampal or hypoglossal tissue is impregnated with GolgiCox solution. Following dehydration, the tissue is embedded in celloidin and sectioned at 160 $\mu$m on a microtome. Sections are then developed in 5% sodium sulphite and mounted on a glass slide with permount. Kidney and retinal tissue is removed from animals that have been perfused with formaldehyde. The fixed tissue is embedded in paraffin and sectioned at 160 $\mu$m on a microtome. Sections are then developed in 5% sodium sulphite and mounted on a glass slide with permount. Sections of hippocampal, hypoglossal, kidney, and retinal tissue are immunostained with antibodies previously shown to react selectively with axons, dendrites, or synapsin. Antigens are localized by indirect immunofluorescence, as described above.

Dendritic and axonal processes are distinguished using established criteria. Purves and Hume, *J. Neurosci.* 1: 441–452 (1981). Dendrites have numerous short processes arising from the main shaft and branched into secondary and tertiary segments relatively close to the cell soma. The axon is readily identified as a smooth, thick process that usually could be followed for at least several hundred microns and frequently can be seen exiting the ganglion via a postganglionic nerve. The arbor of each neuron is assessed by four measures of dendritic complexity. The number of primary dendrites is determined by viewing the cells at 480× in multiple focal planes. A primary dendrite is defined as any process extending from the soma a distance greater than one cell diameter. Total dendritic lengths are measured from the camera lucida tracings with the aid of a digitizing tablet and a general purpose program for neural imaging. Voyvodic, *Soc. Neurosci. Abstr.* 12: 390 (1986). The radius of a circle incorporating the entire arbor is measured as an indicator of the process length. Finally, the extent of branching is determined by counting the number of branches crossing a 50% circle. Scholl, *J. Comp. Neurol.* 244: 245–253 (1953). Sites of presynaptic contact are defined by puncta of synapsin immunoreactivity.

Animals treated with OP-1 are expected to have significantly enhanced dendritic growth when compared to control animals, reflected in increased length, diameter, and number of processes. Further, animals treated with OP-1 are expected to have significantly increased number of synaptic contact when compared to control animals.

EXAMPLE 19

Intra-ocular Transplants

Intra-ocular grafting is a well established model which offers an isolated environment in which CNS synaptic contact can be selectively activated and pharmacologically characterized using drug superfusion techniques in vivo. See, for example, Olson, et al., *ADVANCES IN CELLULAR NEUROBIOLOGY,* (Academic Press, 1983) Grafts of identified CNS areas are placed into the anterior eye chamber of syngeneic and allogeneic host rats. The development and overall structural organization of the graft is relatively organotypic in nature and the mature transplant usually provides an in vivo replica of the grated area. Hoffer, et al., *Brain Res.* 79: 165–184 (1974). After maturation of the transplant, host animals can be anesthetized and pre and postsynaptic activity can be examined using in vivo electrochemical and electrophysiological techniques. Eriksdotter-Nilsson et al., *Brain Res.* 478: 269–280 (1989); Eriksdotter-Nilsson, et al., *Exp. Brain Res.* 74: 89–98 (1989); Hoffer, et al., *Brain Res.* 79: 165–184 (1974); Johansson, et al., *Exp. Neurol.* 134: 25–34 (1995). After sacrifice of the host animal, grafts and underlying irides can be processed for histochemical evaluations of neural and glial elements, and for localization of various transmitter-specific structures and receptors. Bjorklund, et al., *Dev. Brain Res.* 6: 130–140 (1983); Bergman, et al., *Hippocampus* 2: 339–348 (1992); Henschen, et al., *Prog. Brain Res.* 78: 187–191 (1988); Henschen, et al., *Neuroscience* 26: 193–213 (1988); and Henschen, et al., *Brain Res.* 36: 237–247 (1988). Using sequential grafting of fetal brain tissue pieces to the anterior chamber of the eye, it is possible to study the conditions under which mature brain and spinal cord tissue (grafts which have resided in oculo for one or more months and which no longer show morphological signs of growth or development) will accept ingrowth of nerve fibers. Olson, et al., *Brain Res. Bull.* 9: 519–537 (1982). Thus, using the in oculo technique, isolated replicas of defined pathways suitable for structural and functional studies of CNS connectivity can be obtained.

In particular, it has been previously shown that grafted spinal cord will survive and grow in oculo in a manner suggesting that is possesses a considerable intrinsic determination of its normal development. Henschen, et al., *Exp. Brain Res.* 60: 38–47(1985). Further, it has been previously demonstrated that models of the descending coeruleo-spinal noradrenergic and bulbospinal serotonergic pathways to spinal cord can be generated when these CNS areas are co-grafted in oculo. Henschen, et al., *Brain Res. Bull.* 15: 335–342 (1985); Henschen, et al., *Brain Res. Bull.* 17: 801–808 (1986); Henschen, et al., *Dev. Brain Res.* 36: 237–247 (1987); Henschen, et al., *Exp. Brain Res.* 75: 317–326 (1989). In a similar vein, corticospinal and sensory and motor pathways can be constructed in oculo, using co-grafts of cerebral cortex (Palmer, et al., *Exp. Brain Res.*

87: 96–107 (1991); dorsal root ganglia (Trok, et al., 1997), and muscle (Trok, et al., *Brain Res.* 659: 138–146 (1994), with subsequent histological and electrophysiological analysis. Thus, in oculo grafts provide a unique isolated system of a much more "in vivo" than "in vitro" nature, to study spinal cord connectivity and response to injury.

In oculo transplants of specific CNS areas have been employed to evaluate of various putative neurotrophic effects: NGF in hippocampus (Eriksdotter-Nilsson et al., *Brain Res.* 478: 269–280 (1989) and Eriksdotter-Nilsson, et al., *Exp. Brain Res.* 74: 89–98 (1989)), FGF in cortical areas (Giacobini, et al., *Exp. Brain Res.* 86: 73–81 (1991)), IGF-1 in olfactory bulb (Giacobini, et al., 1995)), GDNF in midbrain dopaminergic nucleus and spinal cord (Johansson, et al., *Exp. Neurol.* 134: 25–34 (1995); Trok, et al., *Neuroscience* 71: 231–241 (1996); and Trok, et al., (1996)), and BDNF, NT-3, NT-4, and CNTF in spinal cord (Trok, et al., 1997).

20.1 Effects of OP-1 on Intra-ocular Spinal Cord Transplants

In oculo transplants were employed to evaluate the effects of morphogens on motor neurons. Fisher 344 rats were implanted with syngeneic E18 spinal cord grafts, essentially as previously described by Henschen, et al., *Prog. Brain Res.* 78: 187–191 (1988). OP-1 (0.5 µg) or vehicle was injected into the anterior chamber at weekly intervals. Each rat had an OP-1-treated graft in one eye and a control graft in the contralateral eye. Survival and growth of the graft was followed noninvasively by observation through the cornea over a four week period. After sacrifice of the host animals, grafts were evaluated by histological and immunocytochemical techniques. Olson, L., et al., *ADVANCES IN CELLULAR NEUROBIOLOGY*, pp. 407–442 (Academic Press, 1983); Granholm, et al., *Exp. Neurol.* 118: 7–17 (1992).

Figure 13:
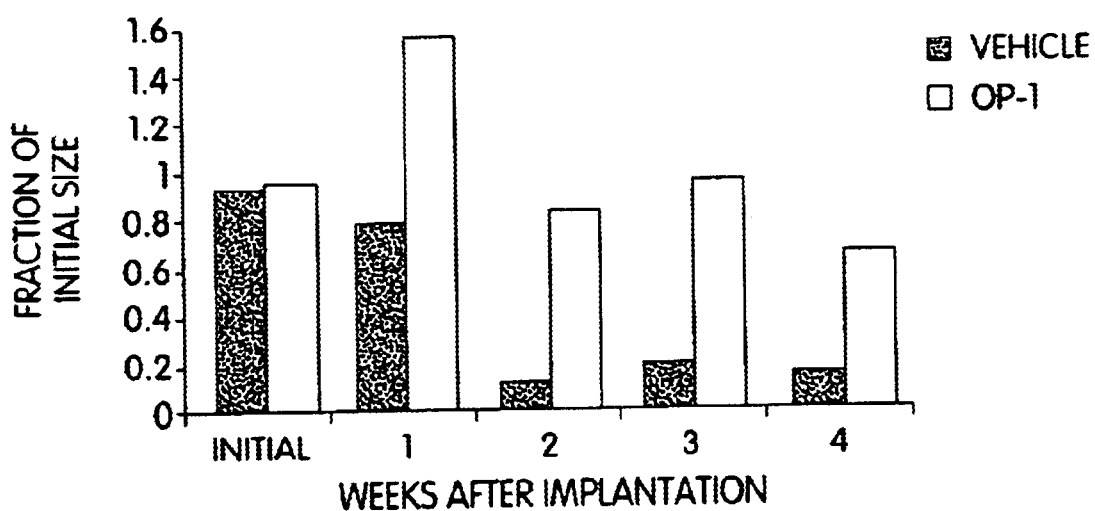
FIG. 13 is a bar graph depicting the effects of OP-1 treatment on the size of spinal cord neurons transplanted intra-ocularly in vivo over a period of four weeks.

As shown in FIG. 13, OP-1-treated grafts maintained a significantly larger size over the four week observation period, compared to control grafts. Transplants treated with weekly injections of vehicle had minimal survival but manifested a marked reduction in size, similar to what has been previously described for E 18 donors. Henschen, et al., *Prog. Brain Res.* 78: 187–191 (1988); Henschen, et al., *Neuroscience* 26: 193–213 (1988). In contrast, grafts treated with weekly injections of 0.5 µg of OP-1 maintained a much greater size and, at the end of four weeks, had a size equal to, or only slightly less than, the initial size at grafting.

Figure 14:
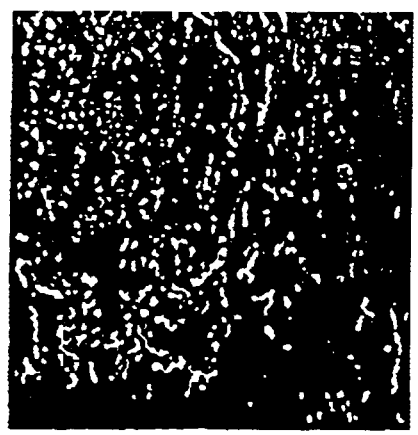
FIG. 14 is a photograph of the neurofilament staining of intra-ocular cultures. Spinal cord transplant cultures were stained four weeks post-grafting. Cultures were treated with weekly injections of vehicle or OP-1.
Figure 14:
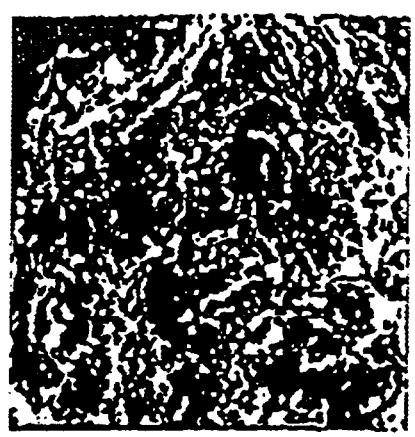
Figure 15:
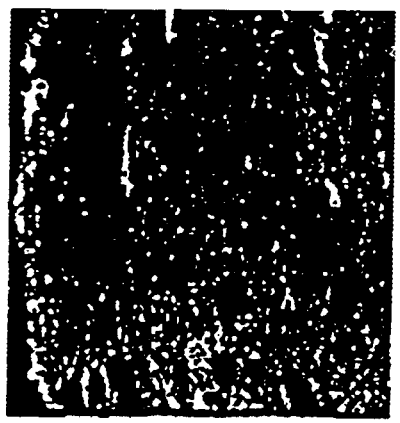
FIG. 15 is a photograph of the choline acetyltransferase staining of intra-ocular cultures. Spinal cord transplant cultures were stained four weeks post-grafting. Cultures were treated with weekly injections of vehicle or OP-1.
Figure 15:

This positive effect of OP-1 was confirmed using immunocytochemical techniques. Overall neuron density was evaluated using MAP2 (i.e., neurofilament immunoreactivity). As seen in FIG. 14, the number of neurofilament-positive neuronal structures was significantly higher in OP-1-treated grafts compared to vehicle-treated transplants. In order to assess more specifically the effects of OP1 on motor neurons, immunocytochemical studies were carried out using choline acetyltransferase (CHAT) immunocytochemistry. The number of cholinergic cell bodies and fibers was also significantly higher in OP-1-treated grafts than in vehicle-treated transplants. See FIG. 15.

EXAMPLE 20

Traumatic Injury Model

The fluid percussion brain injury model was used to assess the ability of morphogens to restore central nervous system functions following significant traumatic brain injury.

I. Fluid Percussion Brain Injury Procedure

The animals used in this study were male Sprague-Dawley rats weighing 250–300 grams (Charles River). The basic surgical preparation for the fluid-percussion brain injury has been previously described. Dietrich, et al., *Acta Neuropathol.* 87: 250–258 (1994) incorporated by reference herein. Briefly, rats were anesthetized with 3% halothane, 30% oxygen, and a balance of nitrous oxide. Tracheal intubation was performed and rats were placed in a stereotaxic frame. A 4.8-mm craniotomy was then made overlying the right parietal cortex, 3.8 mm posterior to bregma and 2.5 mm lateral to the midline. An injury tube was placed over the exposed dura and bonded by adhesive. Dental acrylic was then poured around the injury tube and the injury tube was then plugged with a gelfoam sponge. The scalp was sutured closed and the animal returned to its home case and allowed to recover overnight.

On the next day, fluid-percussion brain injury was produced essentially as described by Dixon, et al., *J. Neurosurg.* 67: 110–119 (1987) and Clifton, et al., *J. Cereb. Blood Flow Metab.* 11: 114–121 (1991). The fluid percussion device consisted of a saline-filled Plexiglas cylinder that is fitted with a transducer housing and injury screw adapted for the rat's skull. The metal screw was firmly connected to the plastic injury tube of the intubated anesthetized rat (70% nitrous oxide, 1.5% halothane, and 30% oxygen), and the injury was induced by the descent of a pendulum that strikes the piston. Rats underwent mild-to-moderate head injury, ranging from 1.6 to 1.9 atm. Brain temperature was indirectly monitored with a thermistor probe inserted into the right temporalis muscle and maintained at 37–37.5° C. Rectal temperature was also measured and maintained at 37° C. prior to and throughout the monitoring period.

II. Administration of Morphogen

Animals in the treatment group received OP1 intracisternally at a dose of 10 µg/injection. Control animals received vehicle solutions lacking OP-1 but with all other components at equivalent final concentrations. Both OP-1 and vehicle-treated animals received two injections, one day and four days following the fluid percussion injury.

To administer the injection, the animals were anesthetized with halothane in 70% $NO_2$/30% $O_2$ and placed in a stereotaxic frame. The procedure for intracisternal injection of OP1 containing solutions or vehicle-only solutions was identical. Using aseptic technique, OP-1 (1 or 10 µg/injection) or an equivalent volume of vehicle were introduced by percutaneous injection (10 µl/injection) into the cisterna magna using a Hamilton syringe fitted with a 26 gauge needle (Yamada, et al., (1991) *J. Cereb. Blood Flow Metab.* 11: 472–478). Before each injection, 1–2 µl of cerebrospinal fluid (CSF) was drawn back through the Hamilton syringe to verify needle placement in the subarachnoid space. Preliminary studies demonstrated that a dye, 1% Evans blue, delivered in this fashion diffused freely through the basal cisterns and over the cerebral cortex within one hour of injection. Animals were randomly assigned to either of the OP-1 treatment groups or to the vehicle treatment group. Animals received two intracisternal injections (2×10 µg/injection OP1 or 2× vehicle); the first injection was administered 24 hours after the brain injury and the second injection was administered 4 days after the brain injury.

III. Behavioral Testing

Three standard functional/behavioral tests were used to assess sensorimotor and reflex function after brain injury.

The tests have been fully described in the literature, including Bederson, et al., (1986) *Stroke* 17: 472–476; DeRyck, et al., (1992) *Brain Res.* 573: 44–60; Markgraf, et al., (1992) *Brain Res.* 575: 238–246; and Alexis, et al., (1995) *Stroke* 26: 2338–2346.

A. The Forelimb Placing Test

Forelimb placing to three separate stimuli (visual, tactile, and proprioceptive) was measured to assess sensorimotor integration. DeRyck, et al., *Brain Res.* 573:44–60 (1992). For the visual placing subtest, the animal is held upright by the researcher and brought close to a table top. Normal placing of the limb on the table is scored as "0," delayed placing (<2 sec) is scored as "1," and no or very delayed placing (>2 sec) is scored as "2." Separate scores are obtained first as the animal is brought forward and then again as the animal is brought sideways to the table (maximum score per limb=4; in each case higher numbers denote greater deficits). For the tactile placing subtest, the animal is held so that it cannot see or touch the table top with its whiskers. The dorsal forepaw is touched lightly to the table top as the animal is first brought forward and then brought sideways to the table. Placing each time is scored as above (maximum score per limb=4). For the proprioceptive placing subtest, the animal is brought forward only and greater pressure is applied to the dorsal forepaw; placing is scored as above (maximum score per limb=2). Finally, the ability of animals to place the forelimb in response to whisker stimulation by the tabletop was tested (maximum score per limb=2). Then subscores were added to give the total forelimb placing score per limb (range=0–12).

B. The Beam Balance Test

Beam balance is sensitive to motor cortical insults. This task was used to assess gross vestibulomotor function by requiring a rat to balance steadily on a narrow beam. Feeney, et al., *Science,* 217: 855–857 (1982); Goldstein, et al., *Behav. Neurosci.* 104: 318–325 (1990). The test involved three 60-second training trials 24 hours before surgery to acquire baseline data. The apparatus consisted of a ¾-inch-wide beam, 10 inches in length, suspended 1 ft. above a table top. The rat was positioned on the beam and had to maintain steady posture with all limbs on top of the beam for 60 seconds. The animals' performance was rated with the scale of Clifton, et al., *J. Cereb Blood Flow Metab.* 11: I114–121 (1991), which ranges from 1 to 6, with a score of 1 being normal and a score of 6 indicating that the animal was unable to support itself on the beam.

C. The Beam Walking Test

This was a test of sensorimotor integration specifically examining hindlimb function. The testing apparatus and rating procedures were adapted from Feeney, et al., *Science,* 217: 855–857 (1982). A 1-inch-wide beam, 4 ft. in length, was suspended 3 ft. above the floor in a dimly lit room. At the far end of the beam was a darkened goal box with a narrow entryway. At equal distances along the beam, four 3-inch metal screws were positioned, angling away from the beam's center. A white noise generator and bright light source at the start of the beam motivated the animal to traverse the beam and enter the goal box. Once inside the goal box, the stimuli were terminated. The rat's latency to reach the goal box (in seconds) and hindlimb performance as it traversed the beam (based on a 1 to 7 rating scale) were recorded. A score of 7 indicates normal beam walking with less than 2 foot slips, and a score of 1 indicates that the rat was unable to traverse the beam in less than 80 seconds. Each rat was trained for three days before surgery to acquire the task and to achieve normal performance (a score of 7) on three consecutive trials. Three baseline trials were collected 24 hours before surgery, and three testing trials were recorded daily thereafter. Mean values of latency and score for each day were computed.

IV. Results

Figure 16:
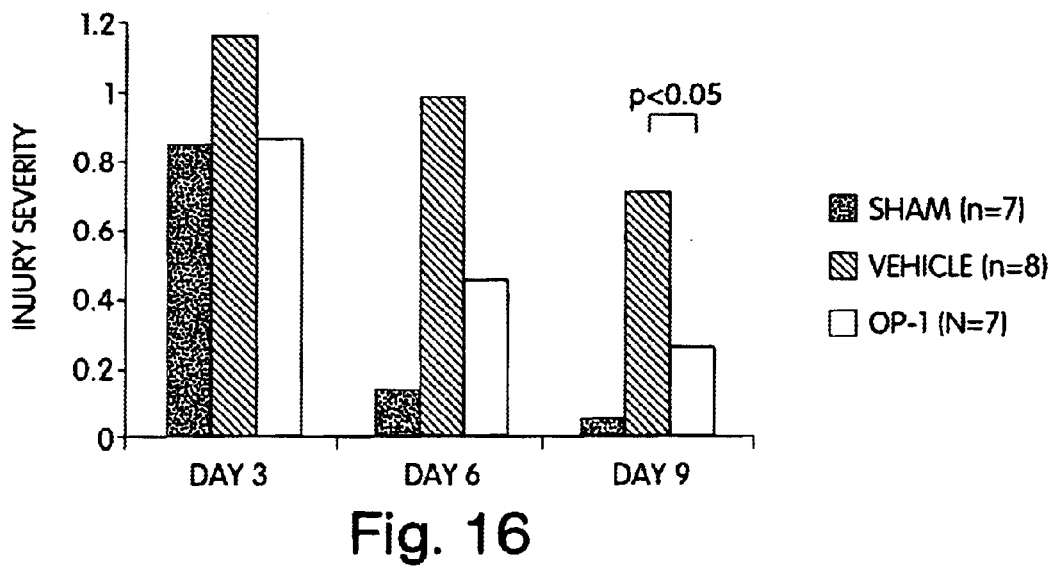
FIG. 16 is a bar graph depicting injury severity scores in the forelimb placing task of sham animals (N=7; black bars), vehicle-treated animals with traumatic brain injury (N=8; grey bars), and OP-1-treated animals with traumatic brain injury (10 $\mu$g/intracisternal injection; total OP-1 delivered in 2 injections=20 $\mu$g/animal; N=7; white bars).
Figure 17:
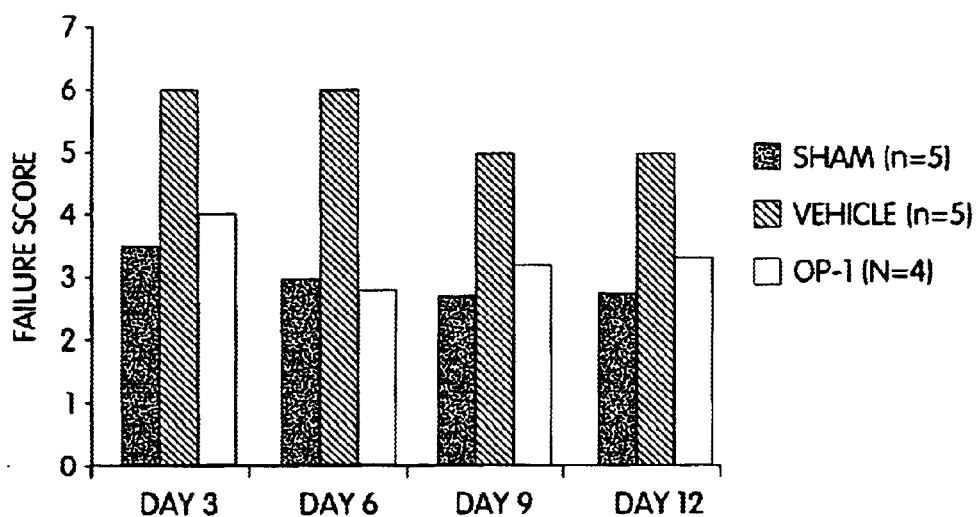
FIG. 17 is a bar graph depicting failure scores in the beam walk task of sham animals (N=5; black bars), vehicle-treated animals with traumatic brain injury (N=5; grey bars), and OP1-treated animals with traumatic brain injury (10 $\mu$g/intracisternal injection; total OP-1 delivered in 2 injections=20 $\mu$g/animal; N=4; white bars).

As illustrated in FIGS. 16–17, OP-1 enhanced the recovery from traumatic brain injury in all three behavioral measures. In the forelimb placing tests, OP-1-treated animals showed a gradual decrease in injury severity scores which attained statistical significance by day 9. See FIG. 16. In the beam balance and beam walking tests, OP-1-treated animals had performance scores that were essentially identical to sham-control animals. See FIGS. 17 and 18. These observations suggests that morphogens are capable of restoring impaired or lost sensory-motor functions following a traumatic brain injury, including visual, tactile, and proprioceptive placement, gross vestibulomotor function, and sensorimotor integration.

Similar routine modifications can be made in other accepted models of traumatic central nervous system injury, to confirm efficacy of morphogen treatment to restore impaired or lost sensory-motor functions.

What is claimed is:

1. A method of treating a mammal with symptoms of amyotrophic lateral sclerosis (ALS), comprising administering to said mammal a morphogen, wherein the morphogen:
   (1) comprises a dimeric protein having an amino acid sequence with:
      (a) at least 70% homology with the C-terminal seven-cysteine skeleton of human OP-1, residues 330–431 of SEQ ID NO: 2; or,
      (b) greater than 60% amino acid sequence identity with said C-terminal seven-cysteine skeleton of human OP-1; and
   (2) stimulates production of an N-CAM or L1 isoform by an NG108-15 cell in vitro; whereby motor function is improved in said mammal.

2. A method of treating a mammal with symptoms of spinal cord injury, comprising administering to said mammal a morphogen, wherein the morphogen:
   (1) comprises a dimeric protein having an amino acid sequence with:
      (a) at least 70% homology with the C-terminal seven-cysteine skeleton of human OP-1, residues 330–431 of SEQ ID NO; 2; or,
      (b) greater than 60% amino acid sequence identity with said C-terminal seven-cysteine skeleton of human OP-1; and
   (2) stimulates production of an N-CAM or L1 isoform by an NG108–15 cell in vitro; whereby motor function is improved in said mammal.

3. The method of claim 2, wherein said spinal cord injury results from a mechanical trauma.

4. The method of claim 2, wherein said spinal cord injury results from a tumor.

5. The method of claim 2, wherein said spinal cord injury results from a chemical trauma.

6. A method of improving motor function in a mammal with symptoms of amyotrophic lateral sclerosis, comprising administering to the mammal a morphogen, wherein the morphogen:
   (1) comprises a dimeric protein having an amino acid sequence with:
      (a) at least 70% homology with the C-terminal seven-cysteine skeleton of human OP-1, residues 330–431 of SEQ ID NO: 2; or,
      (b) greater than 60% amino acid sequence identity with said C-terminal seven-cysteine skeleton of human OP-1; and
   (2) stimulates production of an N-CAM or L1 isoform by an NG108-15 cell in vitro; whereby motor function is improved in the mammal.

7. A method of improving motor function in a mammal with symptoms of spinal cord injury, comprising administering to the mammal a morphogen, wherein the morphogen:
   (1) comprises a dimeric protein having an amino acid sequence with:
      (a) at least 70% homology with the C-terminal seven-cysteine skeleton of human OP-1, residues 330–431 of SEQ ID NO: 2; or,
      (b) greater than 60% amino acid sequence identity with said C-terminal seven-cysteine skeleton of human OP-1; and
   (2) stimulates production of an N-CAM or L1 isoform by an NG108-15 cell in vitro; whereby motor function is improved in the mammal.

8. A method of treating a mammal with symptoms of amyotrophic lateral sclerosis, comprising administering to said minimal a morphogen, selected from: human OP-1, mouse OP-1, human OP-2, mouse OP-2, 60A, GDF-1, BMP2A, DMP2B, DPP, Vg1, Vgr-1, BMP3, BMP5, or BMP6, whereby motor function is improved in said mammal.

9. A method of treating a mammal with symptoms of spinal cord injury, comprising administering to said mammal a morphogen selected from: human OP-1, mouse OP-1, human OP-2, mouse OP-2, 60A, GDF-1, BMP2A, BMP2B, DPP, Vg1, Vgr-1, BMP3, BMP5, or BMP6, whereby motor function is improved in said mammal.

10. A method of improving motor function in a mammal with symptoms of amyotrophic lateral sclerosis, comprising administering to the mammal a morphogen selected from: human OP-1, mouse OP-1, human OP-2, mouse OP-2, 60A, GDF-1, BMP2A, BMP2B, DPP, Vg1, Vgr-1, BMP3, BMP5, or BMP6, whereby the motor function is improved in said mammal.

11. A method of improving motor function in a mammal with symptoms of spinal cord injury, comprising administering to the mammal a morphogen selected from: human OP-1, mouse OP-1, human OP-2, mouse OP-2, 60A, GDF-1, BMP2A, BMP2B, DPP, Vg1, Vgr-1, BMP3, BMP5, or BMP6, whereby the motor function is improved in said mammal.

12. The method of any one of claims 1, 2, 6, 7, 8, 9, 10, or 11, wherein said morphogen is complexed with at least one pro-domain polypeptide of the pro-domains of: OP-1, OP-2, 60A, GDF-1, BMP-2A, BMP-2B, DPP, Vg1, Vgr-1, BMP-3, BMP5, or BMP6.

13. The method of claim 12, wherein said morphogen is complexed with a pair of said pro-domain polypeptides.

14. A method of repairing damaged neural pathway of the peripheral nervous system (PNS) of a mammal, comprising administering to said mammal a morphogen, wherein the morphogen:

(1) comprises a dimeric protein having an amino acid sequence with:
  (a) at least 70% homology with the C-terminal seven-cysteine skeleton of human OP-1, residues 330–431 of SEQ ID NO: 2; or,
  (b) greater than 60% amino acid sequence identity with said C-terminal seven-cysteine skeleton of human OP-1; and,
(2) stimulates production of an N-CAM or L1 isoform by an NG108-15 cell in vitro; whereby the damaged neural pathway of the PNS in said mammal are repaired.

15. A method of improving motor function in a mammal with symptoms of neural pathway damage in the peripheral nervous system (PNS), comprising administering to said mammal a morphogen, wherein the morphogen:

(1) comprises a dimeric protein having an amino acid sequence with:
  (a) at least 70% homology with the C-terminal seven-cysteine skeleton of human OP-1, residues 330–431 of SEQ ID NO: 2; or,
  (b) greater than 60% amino acid sequence identity with said C-terminal seven-cysteine skeleton of human OP-1; and,
(2) stimulates production of an N-CAM or L1 isoform by an NG108-15 cell in vitro; whereby motor function is improved in said mammal.

16. A method of claim 1, 2, 6, 7, 14, or 15, wherein the morphogen is OP-1.

* * * * *

UNITED STATES PATENT AND TRADEMARK OFFICE
CERTIFICATE OF CORRECTION

PATENT NO. : 6,723,698 B2
DATED : April 20, 2004
INVENTOR(S) : Cohen et al.

It is certified that error appears in the above-identified patent and that said Letters Patent is hereby corrected as shown below:

Drawings,
Add Figure 18

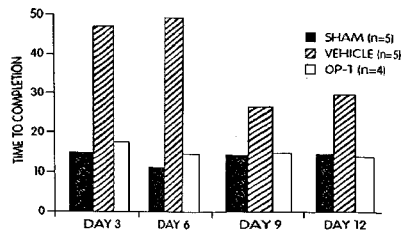

Fig. 18

Column 70,
Line 33, change "minimal" to -- mammal --.
Line 35, change "DMP2B" to -- BMP2B --

Signed and Sealed this

Twenty-fourth Day of August, 2004

JON W. DUDAS
*Director of the United States Patent and Trademark Office*